US011185228B2

(12) United States Patent
Kozuka et al.

(10) Patent No.: US 11,185,228 B2
(45) Date of Patent: *Nov. 30, 2021

(54) CONTROL METHOD OF INFORMATION TERMINAL AND COMPUTER-READABLE RECORDING MEDIUM

(71) Applicant: PANASONIC CORPORATION, Osaka (JP)

(72) Inventors: Kazuki Kozuka, Osaka (JP); Kazutoyo Takata, Osaka (JP); Kenji Kondo, Kyoto (JP); Hirohiko Kimura, Fukui (JP); Toyohiko Sakai, Fukui (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/746,155

(22) Filed: Jan. 17, 2020

(65) Prior Publication Data

US 2020/0146551 A1 May 14, 2020

Related U.S. Application Data

(63) Continuation of application No. 16/380,686, filed on Apr. 10, 2019, now Pat. No. 10,568,512, which is a (Continued)

(51) Int. Cl.
*A61B 5/00* (2006.01)
*G16H 50/70* (2018.01)
(Continued)

(52) U.S. Cl.
CPC ............ *A61B 5/0022* (2013.01); *A61B 5/743* (2013.01); *A61B 5/7425* (2013.01);
(Continued)

(58) Field of Classification Search
CPC ................................................... A61B 5/0022
(Continued)

(56) References Cited

U.S. PATENT DOCUMENTS

2004/0190873 A1* 9/2004 Kito ................... H04N 1/00326
386/225
2006/0224993 A1* 10/2006 Wong ..................... G06F 16/54
715/800

(Continued)

FOREIGN PATENT DOCUMENTS

JP 2007-287018 11/2007
JP 2008-077163 4/2008
(Continued)

OTHER PUBLICATIONS

Akira Oosawa and four others, "Development of "SYNAPSE Case Match", Content-based Image Retrieval System for Supporting Image Diagnosis", Fujifilm Research & Development, FUJIFILM Corporation, Mar. 27, 2013, No. 58, pp. 11-14. (Year: 2013).*

(Continued)

*Primary Examiner* — Joshua B Blanchette
(74) *Attorney, Agent, or Firm* — Greenblum & Bernstein, P.L.C.

(57) ABSTRACT

A control method of an information terminal causes a display to display a display screen which includes a first display region and a second display region. The first display region displays an object medical image. The second display region displays M number of similar medical images and includes ND number of individual regions for displaying the M number of the similar medical images. When an instruction from one or more instruction buttons is detected, a display size of each corresponding region of interest that is included in the second number of the similar medical images is changed while maintaining a size of each of the individual regions in the second display region, and each of the similar (Continued)

medical images is magnified at a magnification ratio of a reference thumbnail.

2 Claims, 72 Drawing Sheets

Related U.S. Application Data continuation of application No. 14/800,025, filed on Jul. 15, 2015, now Pat. No. 10,327,640, which is a continuation of application No. PCT/JP2014/002057, filed on Apr. 9, 2014.

(51) Int. Cl.

| | | |
|---|---|---|
| *G16H 15/00* | (2018.01) | |
| *G16H 30/40* | (2018.01) | |
| *G16H 30/20* | (2018.01) | |
| *A61B 5/055* | (2006.01) | |
| *A61B 5/08* | (2006.01) | |
| *G06F 3/0485* | (2013.01) | |
| *G06F 3/0484* | (2013.01) | |
| *G06F 3/0482* | (2013.01) | |
| *G06F 16/58* | (2019.01) | |
| *A61B 6/03* | (2006.01) | |
| *A61B 6/00* | (2006.01) | |

(52) U.S. Cl.
CPC ........ *G06F 3/0482* (2013.01); *G06F 3/04842* (2013.01); *G06F 3/04855* (2013.01); *G06F 16/5866* (2019.01); *G16H 15/00* (2018.01); *G16H 30/20* (2018.01); *G16H 30/40* (2018.01); *G16H 50/70* (2018.01); *A61B 5/055* (2013.01); *A61B 5/08* (2013.01); *A61B 6/032* (2013.01); *A61B 6/463* (2013.01); *G09G 2340/0407* (2013.01)

(58) Field of Classification Search
USPC ........................................................ 705/2, 3
See application file for complete search history.

(56) References Cited

U.S. PATENT DOCUMENTS

| | | | | |
|---|---|---|---|---|
| 2007/0242069 | A1* | 10/2007 | Matsue | ................ G16H 50/20 345/428 |
| 2008/0123916 | A1* | 5/2008 | Adams | ................ G06F 3/0481 382/128 |
| 2008/0243395 | A1 | 10/2008 | Oosawa et al. | |
| 2009/0080734 | A1 | 3/2009 | Moriya et al. | |
| 2009/0225102 | A1* | 9/2009 | Okubo | .................... G06F 16/58 345/661 |
| 2011/0105879 | A1* | 5/2011 | Masumoto | ............ G16H 30/20 600/407 |
| 2011/0110576 | A1* | 5/2011 | Kreeger | ............. G06F 3/04815 382/132 |
| 2011/0283242 | A1* | 11/2011 | Chew | .................... G06F 16/904 715/863 |

FOREIGN PATENT DOCUMENTS

| | | | | |
|---|---|---|---|---|
| JP | 2008077163 | A | * | 4/2008 |
| JP | 2008-257292 | | | 10/2008 |
| JP | 2014-004252 | | | 1/2014 |
| JP | 2014004252 | A | * | 1/2014 |

OTHER PUBLICATIONS

Preeti Aggarwal, "Semantic and Content-Based Medical Image Retrieval for Lung Cancer Diagnosis with the Inclusion of Expert Knowledge and Proven Pathology," Proceedings of the 2013 IEEE Second International Conference on Image Information Processing, pp. 346-351. (Year: 2013).*
U.S. Appl. No. 14/800,084 to Kenji Kondo et al., filed Jul. 15, 2015.
International Search Report (ISR) in International Patent Application No. PCT/JP2014/002057, dated May 20, 2014.
Akira Oosawa et al., "Development of "SYNAPSE Case Match", Content-based Image Retrieval System for Supporting Image Diagnosis", Fujifilm Research & Development, Fujifilm Corporation, No. 58, pp. 11-14 (Mar. 27, 2013).
Nemoto et al., "Improvement of Tumor Detection Performance in Mammograms by Feature Selection from a Large Numbers of Features and Proposal of Fast Feature Selection Method", IEICE Transactions on Information and Systems D-II, vol. J88-D-II, No. 2, pp. 416-426 (Feb. 2005), together with an English language Abstract.

* cited by examiner

FIG. 16

| DISEASE NAME LIST | 730 | |
|---|---|---|
| MYCOSIS | 14 | 731 |
| ASPERGILLOSIS | 8 | 732 |
| CRYPTOCOCCOSIS | 6 | 733 |
| NEOPLASTIC | 13 | 734 |
| LUNG CANCER | 10 | 735 |
| METASTATIC LUNG CANCER | 3 | 736 |
| NONNEOPLASTIC | 6 | 737 |
| LUNG ABSCESS | 4 | 738 |
| SARCOIDOSIS | 1 | 739 |
| SEPTIC EMBOLI | 1 | 740 |
| MYCOBACTERIOSIS | 6 | 741 |
| NONTUBERCULOUS MYCOBACTERIA | 4 | 742 |
| TUBERCULOSIS | 2 | 743 |
| TUBERCULOSIS | 2 | 744 |
| BRONCHIECTASIS | 1 | 745 |
| ... | 1 | |

FIG. 19

LESION DISTRIBUTION  /750

- ☐ DIFFUSE /751
- ▨ SEGMENTAL /752
- ☐ BRONCHIAL /753
- ☐ BILATERAL /754
- ☐ MULTIPLE /755
- ☐ SUBPLEURAL /756
- ☐ HEMATOGENOUS /757

FIG. 20

LESION DISTRIBUTION ⟋750

☐ DIFFUSE ⟋751    ☐ MULTIPLE ⟋755
▨ SEGMENTAL ⟋752  ☐ SUBPLEURAL ⟋756
☐ BRONCHIAL ⟋753  ☐ HEMATOGENOUS ⟋757
☑ BILATERAL ⟋754

FIG. 22

LESION DISTRIBUTION ⟋750

☐ DIFFUSE ⟋751   ☐ MULTIPLE ⟋755

▨ SEGMENTAL ⟋752   ☐ SUBPLEURAL ⟋756

☑ BRONCHIAL ⟋753   ☐ HEMATOGENOUS ⟋757

☐ BILATERAL ⟋754

FIG. 24

LESION DISTRIBUTION  /750

☐ DIFFUSE /751    ☐ MULTIPLE /755
▨ SEGMENTAL /752  ☑ SUBPLEURAL /756
☐ BRONCHIAL /753  ☐ HEMATOGENOUS /757
☐ BILATERAL /754

| 1100 | PATIENT ID | 123456 |
|---|---|---|
| 1200 | NAME | TARO PANA |
| 1300 | AGE | 28 |
| 1400 | GENDER | MALE |
| 1500 | MEDICAL HISTORY | NONE |
| 1600 | FAMILY MEDICAL HISTORY | NONE |
| 1700 | CHIEF COMPLAINT | COUGHING |
| 1800 | EXAMINATION INFORMATION | (SEE Fig. 27) |
| 1900 | DEFINITIVE DIAGNOSIS | MYCOPLASMA PNEUMONIA |

| 1810 | EXAMINATION ID | 13227895 |
|---|---|---|
| 1820 | EXAMINATION DATE/TIME | 10:00, 5 FEB. 20XX |
| 1830 | EXAMINATION TYPE | BLOOD TEST |
| 1840 | EXAMINATION RESULT | YYYY1 |

| EXAMINATION ID | 13227903 |
|---|---|
| EXAMINATION DATE/TIME | 11:00, 5 FEB. 20XX |
| EXAMINATION TYPE | PLAIN RADIOGRAPHY (CHEST) |
| EXAMINATION RESULT | YYYY2 |

| EXAMINATION ID | 13227989 |
|---|---|
| EXAMINATION DATE/TIME | 9:00, 9 FEB. 20XX |
| EXAMINATION TYPE | CT (CHEST) |
| EXAMINATION RESULT | YYYY3 |

| EXAMINATION ID | 132227989 |
|---|---|
| FINDINGS | MULTIPLE NODULES 0.5 cm TO 1 cm IN SIZE HAVE BEEN FOUND IN RIGHT LUNG FIELD… |
| DIAGNOSIS | INFLAMMATORY NODULES OR TUBERCULOSIS IS SUSPECTED. |

| | |
|---|---|
| SIMILAR CASE ID (4100) | SIM5232 |
| SLICE ID (4200) | CT149391025 |
| REGION OF INTEREST INFORMATION (4300) | $x_l, y_t, x_r, y_b$ |
| IMAGE FEATURE DATA (4400) | $f1, f2, f3, ..., fN$ |
| THUMBNAIL IMAGE DATA (4500) | $(I_{0,0}, I_{0,1}, ..., I_{w-1, h-1})$ |
| LESION DISTRIBUTION INFORMATION (4600) | |
| DEFINITIVE DIAGNOSIS (BROADLY CATEGORIZED DISEASE NAME) (4700) | NEOPLASTIC |
| DEFINITIVE DIAGNOSIS (FINELY CATEGORIZED DISEASE NAME) (4800) | LUNG CANCER |

4000

| | |
|---|---|
| DIFFUSE (4610) | 1 |
| SEGMENTAL (4620) | 0 |
| BRONCHIAL (4630) | 0 |
| BILATERAL (4640) | 1 |
| MULTIPLE (4650) | 1 |
| SUBPLEURAL (4660) | 0 |
| HEMATOGENOUS (4670) | 1 |

FIG. 33

| PATIENT ID | PATIENT NAME | EXAMINATION DATE/TIME | EXAMINATION ID | EXAMINATION TYPE |
|---|---|---|---|---|
| 443982 | ICHIRO YAMADA | 20XX/12/1 | 23982874 | MR (HEAD) |
| 123456 | TARO PANA | 20XX/5/8 | 13227989 | CT (CHEST) |
| 345455 | ... | ... | ... | ... |
| 235982 | ... | ... | ... | ... |

~800

| SERIES ID | DEFINITION | IMAGE |
|---|---|---|
|  |  |  |
|  |  |  |
|  |  |  |

~810

FIG. 34
| PATIENT ID | PATIENT NAME | EXAMINATION DATE/TIME | EXAMINATION ID | EXAMINATION TYPE |
|---|---|---|---|---|
| 443982 | ICHIRO YAMADA | 20XX/12/1 | 23982874 | MR (HEAD) |
| 123456 | TARO PANA | 20XX/5/8 | 13227989 | CT (CHEST) |
| 345455 | ... | ... | ... | ... |
| 235982 | ... | ... | ... | ... |
~800
| SERIES ID | DEFINITION | IMAGE |
|---|---|---|
| CT152729 | LUNG WINDOW SETTING<br><br>SLICE THICKNESS : 5 mm |  |
| CT152730 | LUNG WINDOW SETTING<br><br>SLICE THICKNESS : 1 mm |  |
| CT152731 | MEDIASTINAL WINDOW SETTING<br><br>SLICE THICKNESS : 5 mm |  |
~810

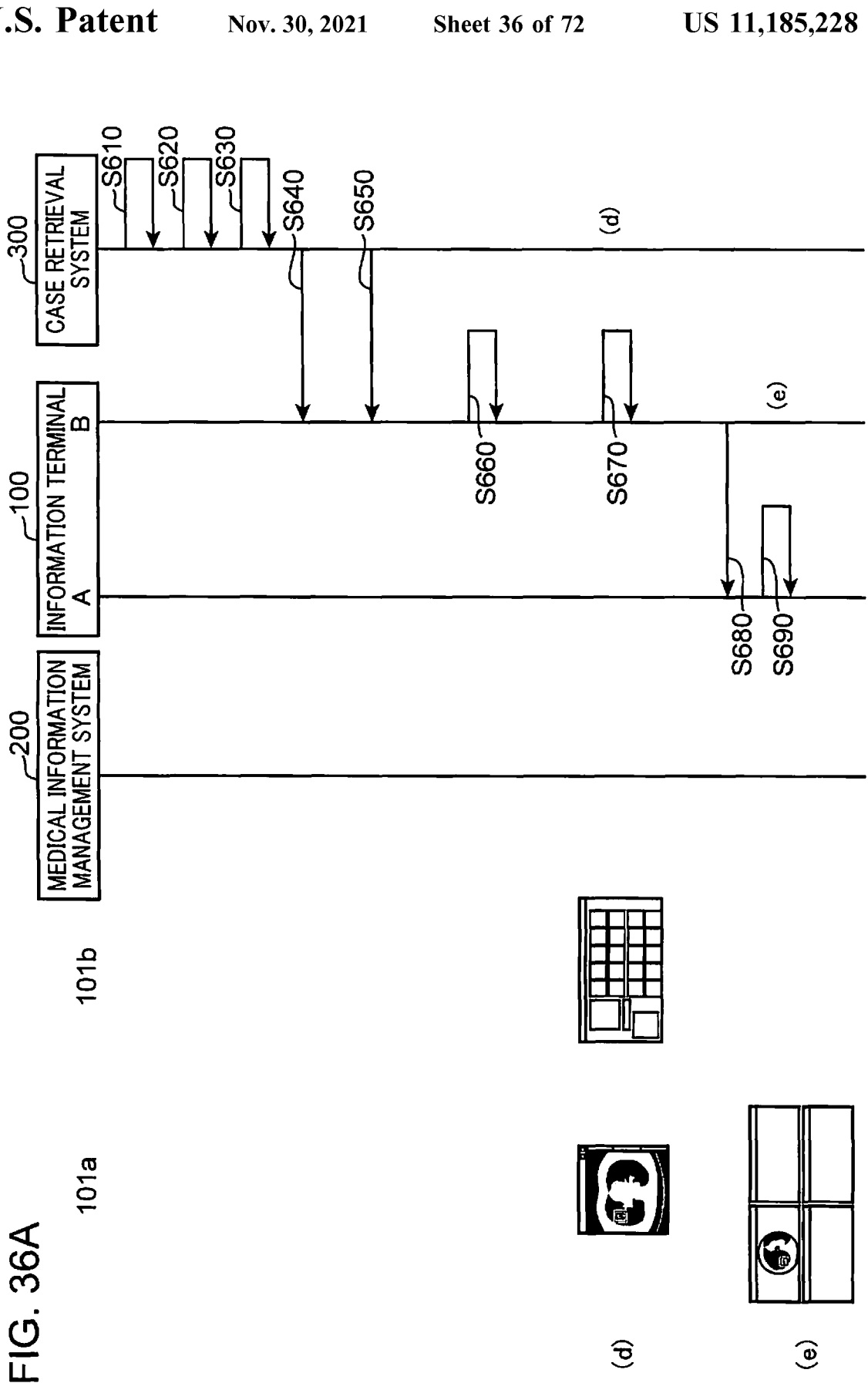

| NUMBER OF ROWS | 2 |
|---|---|
| NUMBER OF COLUMNS | 2 |

~4411

| POSITION | SLICE ID |
|---|---|
| 1ST-ROW, 1ST-COLUMN | CT12353515 |
| 1ST-ROW, 2ND-COLUMN | — |
| 2ND-ROW, 1ST-COLUMN | — |
| 2ND-ROW, 2ND-COLUMN | — |

| USER ID | TERMINAL ID | NUMBER OF COLUMNS | NUMBER OF ROWS | POSITION OF DIAGNOSIS OBJECT CASE |
|---|---|---|---|---|
| U01 | T02 | 2 | 2 | (1,1) |
|  | T04 | 3 | 2 | (2,1) |
| U02 | T02 | 3 | 3 | (2,2) |
| ... | ... | ... | ... | ... |

| USER ID | NUMBER OF COLUMNS | NUMBER OF ROWS | POSITION OF DIAGNOSIS OBJECT CASE |
|---|---|---|---|
| U01 | 2 | 2 | (1,1) |
| U02 | 3 | 2 | (2,1) |
| U03 | 3 | 3 | (2,2) |
| ... | ... | ... | ... |

FIG. 39

| DISEASE NAME ID | BROADLY CATEGORIZED DISEASE NAME | FINELY CATEGORIZED DISEASE NAME | NUMBER OF CASES | SIMILAR CASE ID |
|---|---|---|---|---|
| DIS528 | NEOPLASTIC | LUNG CANCER | 10 | SIM258, SIM551, SIM1209, SIM2341, ... |
| DIS922 | MYCOSIS | ASPERGILLOSIS | 8 | ... |
| ... | MYCOSIS | CRYPTOCOCCOSIS | 6 | ... |
| ... | NONNEOPLASTIC | LUNG ABSCESS | 4 | ... |
| ... | MYCOBACTERIOSIS | NONTUBERCULOUS MYCOBACTERIA | 4 | ... |
| ... | ... | ... | ... | ... |

FIG. 40

| DISEASE NAME LIST | 730 |
|---|---|
| LUNG CANCER | 10 |
| ASPERGILLOSIS | 8 |
| CRYPTOCOCCOSIS | 6 |
| LUNG ABSCESS | 4 |
| NONTUBERCULOUS MYCOBACTERIA | 4 |
| METASTATIC LUNG CANCER | 3 |
| TUBERCULOSIS | 2 |
| INFLAMMATORY NODULE | 1 |
| SEPTIC EMBOLI | 1 |
| BRONCHIECTASIS | 1 |
| UNKNOWN | 1 |

FIG. 41

| DISEASE NAME LIST | 730 |
|---|---|
| MYCOSIS | 14 |
| NEOPLASTIC | 13 |
| NONNEOPLASTIC | 6 |
| MYCOBACTERIOSIS | 6 |
| OTHER | 2 |

FIG. 42

| DISEASE NAME LIST | 730 |
|---|---|
| MYCOSIS | 14 |
|   ASPERGILLOSIS | 8 |
|   CRYPTOCOCCOSIS | 6 |
| NEOPLASTIC | 13 |
|   LUNG CANCER | 10 |
|   METASTATIC LUNG CANCER | 3 |
| NONNEOPLASTIC | 6 |
|   LUNG ABSCESS | 4 |
|   SARCOIDOSIS | 1 |
|   SEPTIC EMBOLI | 1 |
| MYCOBACTERIOSIS | 6 |
|   NONTUBERCULOUS MYCOBACTERIA | 4 |
|   TUBERCULOSIS | 2 |
| OTHER | 2 |
|   BRONCHIECTASIS | 1 |
|   ... | 1 |

DISEASE NAME LIST  730

| MYCOSIS | 14 |
| NEOPLASTIC | 13 |
| NONNEOPLASTIC | 6 |
| MYCOBACTERIOSIS | 6 |
| OTHER | 2 |

⇐ DOUBLE CLICK

DISEASE NAME LIST  730

| MYCOSIS | 14 |
| NEOPLASTIC | 13 |
| NONNEOPLASTIC | 6 |
| LUNG ABSCESS | 4 |
| INFLAMMATORY NODULE | 1 |
| SEPTIC EMBOLI | 1 |
| MYCOBACTERIOSIS | 6 |
| OTHER | 2 |

⇐ EXPANDS INTO FINELY CATEGORIZED DISEASE NAMES

FIG. 44A

| DISTRIBUTION NAME | NUMBER OF CASES | SIMILAR CASE ID |
|---|---|---|
| DIFFUSE | 3 | SIM2521, SIM4123, SIM5225 |
| SEGMENTAL | 0 | NONE |
| BRONCHIAL | 2 | SIM0006, SIM1892, SIM4399 |
| BILATERAL | 12 | ... |
| MULTIPLE | 22 | ... |
| SUBPLEURAL | 0 | NONE |
| HEMATOGENOUS | 5 | ... |

FIG. 44B

LESION DISTRIBUTION ⟋750

☐ DIFFUSE ⟋751  ☐ MULTIPLE ⟋755
▨ SEGMENTAL ⟋752  ▨ SUBPLEURAL ⟋756
☐ BRONCHIAL ⟋753  ☐ HEMATOGENOUS ⟋757
☐ BILATERAL ⟋754

FIG. 63

| | 5000 | |
|---|---|---|
| 5100 | SIMILAR CASE ID | SIM32356 |
| 5200 | MAGNIFIED THUMBNAIL IMAGE DATA (FIRST INSTRUCTION BUTTON) | $I1_{0,0}, I1_{0,1}, I1_{0,0}, \ldots, I1_{w-1,h-1}$ |
| 5300 | MAGNIFIED THUMBNAIL IMAGE DATA (SECOND INSTRUCTION BUTTON) | $I2_{0,0}, I2_{0,1}, I2_{0,0}, \ldots, I2_{w-1,h-1}$ |
| 5400 | MAGNIFIED THUMBNAIL IMAGE DATA (THIRD INSTRUCTION BUTTON) | $I3_{0,0}, I3_{0,1}, I3_{0,0}, \ldots, I3_{w-1,h-1}$ |

CONTROL METHOD OF INFORMATION TERMINAL AND COMPUTER-READABLE RECORDING MEDIUM

CROSS REFERENCE TO RELATED APPLICATIONS

This is a continuation of U.S. patent application Ser. No. 16/380,686, filed Apr. 10, 2019, which is a continuation of U.S. patent application Ser. No. 14/800,025, filed Jul. 15, 2015 and now U.S. Pat. No. 10,327,640 issued Jun. 25, 2019, which is a continuation of International Pat. Appl. No. PCT/JP2014/002057, filed Apr. 9, 2014. The entire disclosure of each of the above-identified applications, including the specification, drawings, and claims, is incorporated herein by reference in its entirety.

TECHNICAL FIELD

The present disclosure relates to a control method of an information terminal for retrieving a similar medical image which is similar to a medical image of a diagnostic interpretation object and a computer-readable recording medium.

BACKGROUND ART

In recent years, we have seen the development and implementation of medical imaging apparatuses that perform CT (Computed Tomography), MRI (Magnetic Resonance Imaging), and the like. CT, MRI, and the like enable acquisition of digitalized high-resolution medical images in large amounts. In addition, medical images after being diagnostically interpreted by a radiologist are sequentially accumulated in PACS (Picture Archiving and Communication Systems) together with a diagnostic interpretation report. Meanwhile, as disclosed in Patent Literature 1 for example, techniques have started to be developed for retrieving past medical images which are similar to a medical image of a diagnostic interpretation object from past cases accumulated in PACS to be used as a reference when newly performing a diagnostic interpretation.

However, further improvements are required.

CITATION LIST

Patent Literature

Patent Literature 1: Japanese Unexamined Patent Publication No. 2008-257292
Patent Literature 2: Japanese Unexamined Patent Publication No. 2014-4252

CITATION LIST

Non Patent Literature

Non Patent Literature 1: Akira Oosawa and four others, "Development of "SYNAPSE Case Match", Content-based Image Retrieval System for Supporting Image Diagnosis", Fujifilm Research & Development, FUJIFILM Corporation, Mar. 27, 2013, No. 58, pp. 11-14.

SUMMARY OF INVENTION

In one general aspect, the techniques disclosed here feature a control method of an information terminal which includes a display and is connected to a case retrieval system, the case retrieval system referring to a medical image database, in which medical images are registered, to retrieve a medical image, the display displaying an object medical image which is a medical image of a diagnostic interpretation object selected from diagnostic interpretation object candidates, disease name information not being set in additional information of the object medical image, the control method causing a computer of the information terminal to:

sense first specification information indicating a region of interest in the object medical image;

receive NC number (where NC is an integer not less than 2) of similar medical images each having a prescribed degree of similarity with a feature quantity of the region of interest indicated by the first specification information from the case retrieval system in accordance with the region of interest, disease name information being set in additional information of the NC number of similar medical images, each of the received NC number of similar medical images including a corresponding region of interest that corresponds to the region of interest and including second specification information indicating the corresponding region of interest in each of the similar medical images;

display on the display a display screen which includes a first display region and a second display region, the first display region displaying the object medical image, the second display region displaying M number (where M is an integer not less than 1 and not more than NC) of similar medical images among the NC number of similar medical images, the second display region including ND number (where ND is an integer not less than M and not more than NC) of individual regions for displaying the M number of similar medical images; and when sensing one instruction for magnifying any one similar medical image among the M number of similar medical images, magnify the corresponding region of interest in each of the M number of or fewer similar medical images so as to match a position corresponding to a center of each of the individual regions in the second display region, and magnify each of the similar medical images in accordance with a size of the corresponding region of interest indicated by the second specification information, while maintaining a size of each of the individual regions at a same size.

According to the aspect described above, further improvements can be achieved. These general and specific aspects may be implemented using a system, a method, and a computer program, and any combination of systems, methods, and computer programs.

BRIEF DESCRIPTION OF DRAWINGS

FIG. 16 is an enlarged view of a disease name list display region.

FIG. 19 is an enlarged view of a distribution list display region.

FIG. 20 is a diagram showing a distribution list display region in which a check mark is input to a check box corresponding to bilateral.

FIG. 22 is a diagram showing a distribution list display region in which a check mark is input to a check box of bronchial.

FIG. 24 is a diagram showing a distribution list display region in which a check mark is input to a check box corresponding to subpleural.

FIG. 26 is a diagram showing a data configuration of patient information.

FIG. 27 is a diagram showing a data configuration of examination information that is registered in the patient information shown in FIG. 26.

FIG. 29 is a diagram showing a data configuration of a diagnostic report.

FIG. 30 is a diagram showing a data configuration of similar case data.

FIG. 33 is a screen diagram of an examination list.

FIG. 34 is a screen diagram of an examination list after an examination is selected.

FIG. 36A is a sequence diagram showing a process in which, after a case retrieval system receives a request for similar case retrieval, the case retrieval system sends back a similar case retrieval result to an information terminal.

FIG. 36B is a diagram showing a data configuration of display box management information.

FIG. 36D is a diagram showing an example of layout management information.

FIG. 36E is a diagram showing an example of layout management information.

FIG. 39 is a diagram showing a data configuration of a disease name list that is generated in S1300 in FIG. 37.

FIG. 40 is a diagram showing a first display example of a disease name list display region.

FIG. 41 is a diagram showing a second display example of a disease name list display region.

FIG. 42 is a diagram showing a third display example of a disease name list display region.

FIG. 44A is a diagram showing a data configuration of a distribution list that is generated in S1400 in FIG. 37.

FIG. 44B is a diagram showing a distribution list display region that is generated using the distribution list shown in FIG. 44A.

FIG. 63 is a diagram showing a data configuration of magnified thumbnail data.

Figure 1:
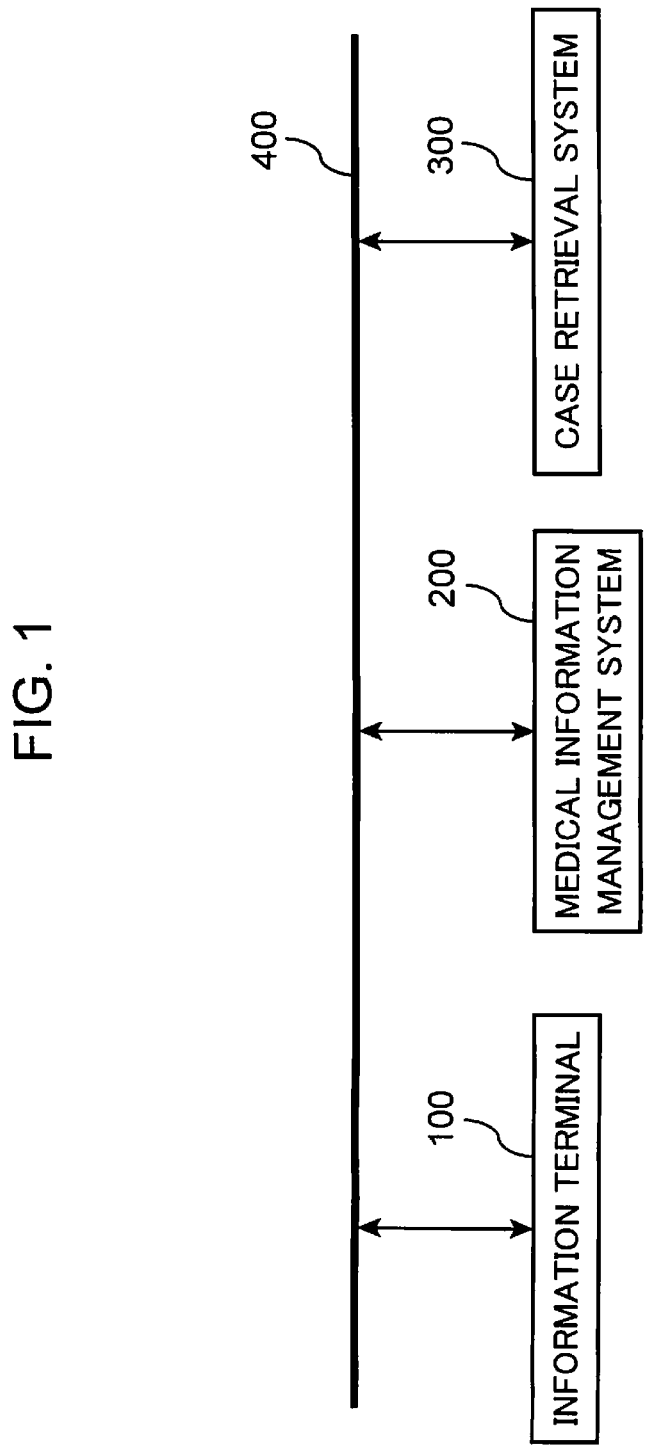
FIG. 1 is an overall configuration diagram of a hospital information system to which an information terminal according to a present embodiment is applied.

DETAILED DESCRIPTION (Circumstances Leading to the Invention of an Aspect of the Present Disclosure)

First, viewpoints of an aspect according to the present disclosure will be described.

Patent Literature 1 discloses an image diagnosis supporting apparatus that presents a case image useful for determining a disorder during image diagnosis based on a diagnosis object image, or statistical information related to the disorder, or the like. A screen of a retrieval result by the image diagnosis supporting apparatus displays a diagnosis object image and information on a representative case for each disorder. Specifically, the screen of the retrieval result displays i) images of representative cases of top three disorders A, D, and G ii) a degree of similarity with a diagnosis object image, the number of registered cases, and the number of representative cases for each disorder, iii) the number of retrievals (total number of retrieved disorders), and iv) a "next page" software button and the like for referring to information on other disorders that cannot be displayed on one screen (paragraphs (0062) and (0063) and FIG. 6(E)).

Patent Literature 1 contains no descriptions regarding magnifying an image of a representative case on a screen of a retrieval result. Therefore, given that Patent Literature 1 does not even disclose simple magnification of images of representative cases, Patent Literature 1 fails to disclose innovative measures such as, on a screen of a retrieval result which is restricted in terms of the number of images that can be displayed, magnifying respective images of representative cases with a focus on lesion sites contained in the images of the representative cases.

Patent Literature 2 discloses a medical image displaying apparatus that achieves improved efficiency of comparative diagnostic interpretation with respect to medical images of a same patient. In this case, comparative diagnostic interpretation refers to i) comparative diagnostic interpretation using image data obtained by different image diagnostic apparatuses or obtained under different photographic conditions with respect to a same patient or to ii) comparative diagnostic interpretation using past and latest image data obtained by a same image diagnostic apparatus with respect to a same patient. In other words, the comparative diagnostic interpretation disclosed in Patent Literature 2 is comparative diagnostic interpretation using image data of a same patient.

A display screen of the medical image displaying apparatus displays three types of software buttons for magnifying or reducing a thumbnail image that is displayed in a thumbnail display area: "standard", "by magnification ratio", and "by size" (paragraph (0040) and FIG. 6). When "by magnification ratio" or "by size" is selected, the thumbnail image is magnified and displayed so as to include a lesion range or a lesion position. Accordingly, confirmation of a lesion by thumbnail images displayed as a list can be made easier in comparison to a case where the "standard" button is selected. In addition, when "by size" is selected, a thumbnail size of a thumbnail image becomes equal to a size when "standard" is selected in order to preserve list display characteristics (paragraphs (0041) to (0043) and FIG. 7). Moreover, in Patent Literature 2, thumbnail images are displayed in chronological order (for example, refer to FIG. 6 in Patent Literature 2).

According to Patent Literature 2, when "by magnification ratio" or "by size" is selected, all of the thumbnail images that include a lesion range or a lesion position are magnified. In other words, in addition to thumbnail images that are displayed in the thumbnail display area, thumbnail images that cannot be displayed in the thumbnail display area are also magnified (for example, refer to FIGS. 6 and 7 in Patent Literature 2).

This is because Patent Literature 2 is premised on comparing images of a same patient with the passage of time (comparative diagnostic interpretation). Since comparative diagnostic interpretation is primarily performed for the purpose of follow-up observation, medical images are photographed over a period of six months or even a year. Therefore, it is unlikely that the number of medical images is significantly large and, even if all of the thumbnail images are to be magnified, processing load on the system is not significant.

In addition, the thumbnail images are all images of the same patient. Therefore, unlike a case where images of a diagnostic interpretation object are compared with images of another patient, there is no need to perform work for evaluating whether the respective thumbnail images are similar to one another. In other words, the thumbnail images according to Patent Literature 2 are used to chronologically evaluate changes in a lesion of the same patient. Therefore, when magnifying and displaying thumbnail images, work such as magnifying some thumbnail images and not magnifying other thumbnail images based on similarity relationships with images of other patients is not created to begin with.

Non Patent Literature 1 discloses a similar case retrieval system in which, due to a function of retrieving a past similar case using a lesion image, appropriate information is instantaneously extracted and presented from clinical knowledge accumulated in PACS described above and the like in order to support image diagnosis of a physician. Specifically, the present system retrieves case images with features of lesions similar to an examination image and displays a plurality of case images in an order of similarity. Subsequently, one reference case image is selected among the plurality of displayed case images and is displayed side by side with the examination image ("2.2 Feature of Present System" on page 12 and FIG. 3).

The system disclosed in Non Patent Literature 1 provides no description of magnifying case images displayed in plurality in an order of similarity. Therefore, given that Non Patent Literature 1 does not even disclose simple magnification of case images, Non Patent Literature 1 fails to disclose innovative measures such as, on a screen of a retrieval result which is restricted in terms of the number of images that can be displayed, magnifying respective images of representative cases with a focus on lesion sites contained in the images of the representative cases.

When evaluating a lesion appearing in a medical image that is a diagnostic interpretation object for which a disease name has not yet been specified, it is conceivably effective to refer to similar medical images that are similar to the medical image that is the diagnostic interpretation object among other medical images for which disease names have already been specified. However, constructing such a system means that a significantly large number of medical images are to be registered in the medical image database. Even in such a case, a similar medical image to be used as a reference when diagnosing the medical image that is the diagnostic interpretation object is desirably presented to a physician in an effective manner.

Based on the considerations described above, the present inventors have arrived at respective aspects of the present disclosure as follows.

A first aspect of the present disclosure is a control method of an information terminal which includes a display and is connected to a case retrieval system, the case retrieval system referring to a medical image database, in which medical images are registered, to retrieve a medical image, the display displaying an object medical image which is a medical image of a diagnostic interpretation object selected from diagnostic interpretation object candidates, disease name information not being set in additional information of the object medical image, the control method causing a computer of the information terminal to:

sense first specification information indicating a region of interest in the object medical image;

receive NC number (where NC is an integer not less than 2) of similar medical images each having a prescribed degree of similarity with a feature quantity of the region of interest indicated by the first specification information from the case retrieval system in accordance with the region of interest, disease name information being set in additional information of the NC number of similar medical images, each of the received NC number of similar medical images including a corresponding region of interest that corresponds to the region of interest and including second specification information indicating the corresponding region of interest in each of the similar medical images;

display on the display a display screen which includes a first display region and a second display region, the first display region displaying the object medical image, the second display region displaying M number (where M is an integer not less than 1 and not more than NC) of similar medical images among the NC number of similar medical images, the second display region including ND number (where ND is an integer not less than M and not more than NC) of individual regions for displaying the M number of similar medical images; and when sensing one instruction for magnifying any one similar medical image among the M number of similar medical images, magnify the corresponding region of interest in each of the M number of or fewer similar medical images so as to match a position corresponding to a center of each of the individual regions in the second display region, and magnify each of the similar medical images in accordance with a size of the corresponding region of interest indicated by the second specification information, while maintaining a size of each of the individual regions at a same size.

According to the present aspect, NC number of similar medical images which have a prescribed degree of similarity with a region of interest in the object medical image that is the diagnostic interpretation object and whose disease names have already been specified are received from the case retrieval system, and M number of similar medical images among the NC number of similar medical images are displayed. Accordingly, similar medical images to be used as a reference when evaluating a disease name of a lesion appearing in the object medical image can be efficiently extracted from a significantly large number of medical images registered in the medical image database and presented to a physician.

In addition, an image having attracted the interest of a physician among displayed similar medical images can be magnified. In doing so, in the present aspect, when one instruction for magnifying any one similar medical image among the M number of similar medical images is sensed, the corresponding region of interest in each of the M number of or fewer similar medical images is magnified so as to match a position corresponding to a center of each of individual regions in the second display region while maintaining a size of each individual region at a same size.

Accordingly, individual magnification instructions for each of the displayed similar medical images are no longer required. As a result, operation efficiency can be improved. In addition, when magnifying the similar medical images, the size of each individual region of the similar medical images is maintained at a same size. Therefore, while magnifying the M number of or fewer similar medical images, the display screen which is restricted in terms of the number of images that can be displayed can be effectively utilized to magnify and display each of the M number of or fewer similar medical images. Furthermore, the corresponding region of interest in each of the similar medical images is magnified so as to match a position corresponding to a center of each of the individual regions. Therefore, each of the M number of or fewer similar medical images is magnified so as to be centered on a region having attracted the interest of a physician among the M number of or fewer similar medical images.

As described above, with one instruction, each of the M number of or fewer similar medical images is magnified so as to be centered on a region having attracted the interest of a physician while effectively utilizing the display screen which is restricted in terms of the number of images that can be displayed. As a result, for example, even when a significantly large number of medical images are registered in the medical image database, a similar medical image to be used as a reference when diagnosing the object medical image that is the diagnostic interpretation object is presented to a physician in an effective manner. Therefore, diagnostic accuracy can be improved.

In addition, each of the received NC number of similar medical images may include second specification information indicating the corresponding region of interest in each of the similar medical images, and
when magnifying the corresponding region of interest in each of the M number of or fewer similar medical images so as to match a position corresponding to a center of each of the individual regions, each of the similar medical images may be magnified in accordance with a size of the corresponding region of interest indicated by the second specification information.

Among the NC number of similar medical images, sizes of the corresponding regions of interest are not the same. This is due to factors such as differences in sizes of lesions included in the respective similar medical images and differences among physicians having assigned the corresponding regions of interest in the past.

Therefore, when magnifying the corresponding region of interest in each of the M number of or fewer similar medical images at a constant ratio that is common to the M number of or fewer similar medical images, the magnified corresponding region of interest is relatively small when the corresponding region of interest is relatively small, and the magnified corresponding region of interest is relatively large when the corresponding region of interest is relatively large. In other words, even when the M number of or fewer similar medical images are magnified, sizes of the magnified corresponding regions of interest vary.

According to the present aspect, for example, when magnifying the corresponding region of interest in each of the M number of or fewer similar medical images so as to match a position corresponding to a center of each of the individual regions, each of the similar medical images is magnified in accordance with a size of the corresponding region of interest which is indicated by the second specification information.

Accordingly, when magnifying the M number of or fewer similar medical images, the variation in the sizes of the magnified corresponding regions of interest can be converged to a certain range among the M number of or fewer similar medical images.

Therefore, with respect to the M number of or fewer similar medical images, a physician can observe the magnified corresponding regions of interest in approximately similar sizes. As a result, an occurrence of a situation where the corresponding region of interest in a part of the similar medical images is overlooked due to being magnified in a small size can be prevented and diagnostic accuracy can be improved.

In addition, the first aspect described above, for example, may further cause the computer of the information terminal to:
display the M number of similar medical images among the NC number of similar medical images in the second display region in a descending order of degrees of similarity with the object medical image; and
when the one instruction for magnifying any one similar medical image among the M number of similar medical images is sensed, with respect to each of the M number of or fewer similar medical images in the M number of ranges that are displayed in the second display region upon sensing the one instruction, magnify the corresponding region of interest in each of the M number of or fewer similar medical images so as to match a position corresponding to a center of each of the individual regions in the second display region while maintaining a size of each of the individual regions at a same size.

In this case, one instruction for magnifying any one similar medical image among the M number of or fewer similar medical images causes the M number of or fewer similar medical images to be magnified. Therefore, when a physician selects any one similar medical image among the M number of or fewer similar medical images in order to magnify and confirm details of the selected similar medical image, the other similar medical images among the M number of similar medical images are also magnified. In other words, instead of requesting the physician to perform a special operation for magnifying the M number of similar medical images, a natural flow of an operation by the physician for selecting any one similar medical image among the M number of similar medical images in order to magnify and confirm details of the selected similar medical image also causes the other similar medical images among the M number of similar medical images to be magnified. As a result, the M number of or fewer similar medical images are magnified in an efficient manner. Therefore, an operation burden on the physician can be reduced and, accordingly, the physician can devote more attention to making professional judgments and an improvement in diagnostic accuracy can be achieved.

In addition, in the present aspect, when one instruction for magnifying any one similar medical image among the M number of similar medical images is sensed, the M number of or fewer similar medical images are magnified in the M number of ranges that are displayed in the second display region upon sensing the one instruction.

In other words, even in a case where similar medical images which have a prescribed degree of similarity with a region of interest in the medical image that is the diagnostic interpretation object among a significantly large number of medical images that are registered in the medical image database are received from the case retrieval system, the number of the received NC number of similar medical images, such as 200 images or 300 images, is large. In this case, even when images are to be magnified by one instruction, it is not efficient to magnify all of the received NC number of similar medical images. Therefore, images are more desirably magnified by the one magnification instruction by limiting images to be magnified to those in a certain range among the received NC number of similar medical images.

For the purpose of displaying similar medical images which have a prescribed degree of similarity with a region of interest in the object medical image that is a medical image being the diagnostic interpretation object in a descending order of the degrees of similarity with the object medical image and evaluating a disease name of a lesion that appears in the object medical image, when sensing the one magnification instruction, the magnification is desirably limited to images having a certain similarity relationship with the one similar medical image. On the other hand, it is not efficient to calculate which of the images have a certain similarity relationship with the one similar medical image each time one instruction for magnifying any one similar medical image among the M number of similar medical images is sensed.

In consideration thereof, in the present aspect, when one instruction for magnifying any one similar medical image among the M number of similar medical images is sensed, the M number of ranges that are displayed in the second display region upon sensing the one instruction are assumed to approximate images having a certain similarity relationship with the one similar medical image. In addition, in the present aspect, each of the M number of or fewer similar medical images is magnified in the M number of ranges that are displayed in the second display region upon sensing the one instruction.

Specifically, in the present aspect, instead of magnifying all of the received NC number of similar medical images, magnification is performed by limiting images to be magnified to those in a certain range among the received NC number of similar medical images or, in other words, limiting images to be magnified to those that can be assumed to have a certain similarity relationship with the one similar medical image.

As described above, in the present aspect, similar medical images which have a prescribed degree of similarity with a region of interest in the medical image that is the diagnostic interpretation object are displayed in a descending order of the degrees of similarity with the medical image that is the diagnostic interpretation object. In addition, when magnifying an image having attracted the interest of a physician among displayed similar medical images, magnification is performed by limiting images to be magnified to those in a certain similarity relationship with the one similar medical image. Therefore, even when a significantly large number of similar medical images are received, the similar medical images are magnified in a range that conforms to the purpose of evaluating a disease name of a lesion that appears in the medical image that is the diagnostic interpretation object. As a result, a physician can be effectively provided with information required to perform the evaluation while significantly reducing processing load on the system and accuracy of medical judgment can be improved.

In addition, in the first aspect described above, for example, the display screen may include a scroll bar, when a movement of the scroll bar is sensed, the similar medical images displayed in the second display region may be scrolled, and the number of the similar medical images to be magnified may be increased in accordance with the similar medical images being scrolled.

According to the present aspect, the number of the magnified similar medical images is increased as the similar medical images are scrolled. In other words, a range in which images are magnified by the one magnification instruction is initially kept small and subsequently varied.

Accordingly, images that are once magnified need not be subsequently reduced and, for example, the ND number of ranges that are newly displayed in the second display region is continued on the assumption that the ND number of ranges approximate images in a certain similarity relationship with the one similar medical image.

Therefore, even when the similar medical images are scrolled, magnification of the similar medical images is continued in a range that conforms to the purpose of evaluating a disease name of a lesion that appears in the medical image that is the diagnostic interpretation object. As a result, a physician can be continuously provided with information required to perform the evaluation while significantly reducing processing load on the system and accuracy of medical judgment can be improved.

In addition, in the first aspect described above, for example, information indicating a total number NC of the NC number of received similar medical images may be displayed on the display screen.

A second aspect of the present disclosure is a control method of an information terminal which includes a display and is connected to a case retrieval system, the case retrieval system referring to a medical image database, in which medical images are registered, to retrieve a medical image is, the display displaying an object medical image which is a medical image of a diagnostic interpretation object selected from diagnostic interpretation object candidates, disease name information not being set in additional information of the object medical image, the control method causing a computer of the information terminal to:

sense first specification information indicating a region of interest in the object medical image;

receive NC number (where NC is an integer not less than 2) of similar medical images each having a prescribed degree of similarity with a feature quantity of the region of interest indicated by the first specification information from the case retrieval system in accordance with the region of interest, disease name information being set in additional information of the NC number of similar medical images, each of the received NC number of similar medical images including a corresponding region of interest that corresponds to the region of interest and including second specification information indicating the corresponding region of interest in each of the similar medical images;

display on the display a display screen which includes a first display region and a second display region, the first display region displaying the object medical image, the second display region displaying M number (where M is an integer not less than 1 and not more than NC) of similar medical images among the NC number of similar medical images, the second display region including ND number (where ND is an integer not less than M and not more than NC) of individual regions for displaying the M number of similar medical images, the display screen including one or more instruction buttons, which are common to the M number of similar medical images, for changing a display size of the M number of similar medical images, the one or more instruction buttons including a first instruction button, the first instruction button being for causing each corresponding region of interest included in the M number of similar medical images to be magnified and displayed at a predetermined magnification ratio, the magnification ratio being predetermined to bring a size of each magnified corresponding region of interest to be smaller than a size of each of the individual regions, the magnification ratio being different for each similar medical image; and when sensing one instruction using the first instruction button, change a display size of each corresponding region of interest included in the M number of similar medical images in accordance with a size of the corresponding region of interest indicated by the second specification information, while maintaining the size of each of the individual regions in the second display region at a same size.

In the present aspect, when one instruction using one or more instruction buttons common to the M number of similar medical images is sensed, a display size of each corresponding region of interest included in the M number of similar medical images is changed while a size of each individual region in the second display region is maintained at a same size. Accordingly, individual instructions for each of the displayed M number of similar medical images are no longer required. As a result, operation efficiency can be improved. In addition, when changing the display size of the M number of similar medical images, a size of each individual region of the M number of similar medical images is maintained at a same size. Therefore, when changing the display size of the M number of similar medical images, the display size of each of the M number of similar medical images can be changed by effectively utilizing the display screen which is restricted in terms of the number of images that can be displayed.

As described above, by one instruction that is common to the M number of similar medical images, the display size of each of the M number of similar medical images can be changed so as to be centered on a region having attracted the interest of a physician while effectively utilizing the display screen which is restricted in terms of the number of images that can be displayed. As a result, for example, even when a significantly large number of medical images are registered in the medical image database, a similar medical image to be used as a reference when diagnosing the object medical image is presented to a physician in an effective manner. Therefore, accuracy of medical judgment can be improved.

In addition, display sizes of the M number of similar medical images are to be changed by one instruction that is common to the M number of similar medical images. Therefore, when a physician performs one operation on an instruction button in order to confirm a finer detail while changing display sizes among the M number of similar medical images, all of the M number of similar medical images are to be magnified. In other words, instead of requesting the physician to perform an individual operation for changing the display size of the M number of similar medical images, a natural flow of an operation by the physician which involves performing one operation on the instruction button for changing the display size to confirm a finer detail causes display sizes of all of the M number of similar medical images to be changed. As a result, the display sizes of the M number of similar medical images are efficiently changed. Therefore, an operation burden on the physician can be reduced and, accordingly, the physician can devote more attention to making professional judgments and an improvement in diagnostic accuracy can be achieved.

In addition, the one or more instruction buttons may include a first instruction button, the first instruction button being for causing each corresponding region of interest included in the M number of similar medical images to be magnified and displayed at a predetermined magnification ratio, the magnification ratio being predetermined to bring a size of each magnified corresponding region of interest to be smaller than a size of each of the individual regions, and when one instruction using the first instruction button is sensed, in accordance with the one instruction, a display size of each corresponding region of interest that is included in the M number of similar medical images may be changed, while maintaining the size of each of the individual regions that displays the M number of similar medical images at a same size.

According to the present aspect, the display screen includes, as the one or more instruction buttons, a first instruction button for magnifying and displaying each corresponding region of interest that is included in the M number of similar medical images at a predetermined magnification ratio, the magnification ratio being predetermined to bring a size of each magnified corresponding region of interest to be smaller than a size of each of the individual regions.

Accordingly, with one instruction, a physician can change a display size of each corresponding region of interest to a display size that is an intermediate display size between displaying the M number of similar medical images at an initial display size and displaying each corresponding region of interest that is included in the M number of similar medical images so as to conform to the size of each of the individual regions.

Among the NC number of similar medical images, sizes of the corresponding regions of interest are not the same. This is due to factors such as differences in sizes of lesions included in the respective similar medical images and differences among physicians having assigned the corresponding regions of interest in the past.

Therefore, when changing a display size of the corresponding region of interest that is included in each of the M number of similar medical images at a constant ratio that is common to the M number of similar medical images, the magnified corresponding region of interest is relatively small when the corresponding region of interest is relatively small, and the magnified corresponding region of interest is relatively large when the corresponding region of interest is relatively large. In other words, even when the M number of similar medical images are magnified, display sizes of the magnified corresponding regions of interest vary.

According to the present aspect, for example, the predetermined magnification ratio differs for each individual similar medical image, and when one instruction using the first instruction button is sensed, a display size of each of the corresponding regions of interest is changed in accordance with a size of the corresponding region of interest indicated in the second specification information.

Accordingly, when changing a display size of each of the corresponding regions of interest, the variation in the changed display sizes of the corresponding regions of interest can be converged to a certain range among the M number of similar medical images.

Therefore, with respect to the M number of similar medical images, a physician can observe each of the object regions of interest with the changed display sizes in approximately similar sizes. As a result, an occurrence of a situation where the object region of interest in a part of the similar medical images is overlooked due to being changed to a smaller display size than display sizes of the object regions of interest of other similar medical images can be prevented and diagnostic accuracy can be improved.

In addition, the second aspect described above, for example, may further cause the computer of the information terminal to:

display the M number of similar medical images among the NC number of similar medical images in the second display region in a descending order of degrees of similarity with the object medical image; and when one instruction using the one or more common instruction buttons is sensed, with respect to each of the M number of similar medical images in the M number of ranges that are displayed in the second display region upon sensing the one instruction, change a display size of each corresponding region of interest included in the M number of similar medical images, while maintaining a size of each of the individual regions in the second display region at a same size.

In this case, when an instruction using one instruction button that is common to the M number of similar medical images is sensed, a display size of each of the M number of similar medical images is changed in the M number of ranges that are displayed in the second display region upon sensing the one instruction. In other words, even in a case where similar medical images which have a prescribed degree of similarity with a region of interest in the object medical image among a significantly large number of medical images that are registered in the medical image database are received from the case retrieval system, the number of the received NC number of similar medical images, such as NC=200 images or NC=300 images, is large. In this case, even when display sizes of the similar medical images are to be changed by one instruction, it is not efficient to change the display sizes of all of the received NC number of similar medical images. Therefore, display sizes of the similar medical images are more desirably changed by the one instruction by limiting such images to images in a certain range among the received NC number of similar medical images.

For the purpose of displaying similar medical images which have a prescribed degree of similarity with a region of interest in the object medical image that is a medical image being the diagnostic interpretation object in a descending order of the degrees of similarity with the object medical image and evaluating a disease name of a lesion that appears in the object medical image, when sensing the one instruction, the change in display sizes is desirably limited to images having a certain similarity relationship with the object medical image. On the other hand, it is not efficient to calculate which of the images have a certain similarity relationship with the object medical image each time the object medical image is changed or each time the similar medical image is changed.

In the present aspect, the similar medical images are displayed in a descending order of degrees of similarity with the object medical image. Therefore, when one instruction using the instruction button is sensed, based on relationships with the object medical image, it is assumed that the M number of similar medical images that are displayed upon sensing the one instruction approximate images having a certain similarity relationship with the object medical image. Accordingly, in the present aspect, display sizes of the M number of similar medical images are changed in the M number of ranges that are displayed in the second display region upon sensing the one instruction. In other words, in the present aspect, instead of changing the display sizes of all of the received NC number of similar medical images, display sizes are changed by limiting images whose display sizes are to be changed to those in a certain range among the received similar medical images or, in other words, limiting images whose display sizes are to be changed to those that can be assumed to have a certain similarity relationship with the medical image that is the diagnostic interpretation object.

As described above, in the present aspect, similar medical images which have a prescribed degree of similarity with a region of interest in the object medical image are displayed in a descending order of the degrees of similarity with the object medical image, and when changing a display size of an image having attracted the interest of a physician among the displayed M number of similar medical images, display sizes are changed by limiting images to those assumed to have a certain similarity relationship with the one similar medical image. Therefore, even when a significantly large number of similar medical images are received, display sizes of the similar medical images are changed in a range that conforms to the purpose of evaluating a disease name of a lesion that appears in the object medical image. As a result, a physician can be effectively provided with information required to perform the evaluation while significantly reducing processing load on the system and accuracy of medical judgment can be improved.

In addition, in the second aspect described above, for example, the display screen may include at least a second instruction button and a third instruction button as the one or more instruction buttons, the second instruction button being for causing the M number of similar medical images to be displayed in each of the individual regions at an initial display size, the third instruction button being for causing each corresponding region of interest included in the M number of similar medical images to be magnified and displayed so as to conform to a size of each of the individual regions, and when one instruction using either the second instruction button or the third instruction button is sensed, in accordance with the one instruction, a display size of each corresponding region of interest included in the M number of similar medical images may be uniformly changed, while maintaining a size of each of the individual regions for displaying the M number of similar medical images at a same size.

According to the present aspect, when displaying the M number of similar medical images at an initial display size in each of the individual regions, a physician may select one instruction that is the second instruction button. In addition, when magnifying and displaying each corresponding region of interest that is included in the M number of similar medical images so as to conform to a size of each of the individual regions, a physician may select one instruction that is the third instruction button. Accordingly, by one instruction that is the second instruction button or the third instruction button, a display size of each corresponding region of interest that is included in the M number of similar medical images changes uniformly while a size of each individual region that displays the M number of similar medical images are maintained at a same size.

Therefore, since a physician can both display the M number of similar medical images at an initial display size and display each corresponding region of interest that is included in the M number of similar medical images so as to conform to the size of each of the individual regions by one operation, the number of operations can be reduced significantly.

In addition, in the first or second aspect described above, for example, when a size of the corresponding region of interest indicated by the second specification information is a first size, the corresponding region of interest may be magnified larger as compared to a case where the size of the corresponding region of interest indicated by the second specification information is a second size that is larger than the first size.

According to the present aspect, when magnifying the similar medical images, a variation in the sizes of the magnified similar medical images can be converged to a certain range among the similar medical images. Specifically, when a size of the corresponding region of interest is a first size, the corresponding region of interest is magnified at a higher ratio as compared to a case where the size of the corresponding region of interest is a second size that is larger than the first size. Accordingly, a size of the magnified corresponding region of interest can be set to a similar size independently of the size of the corresponding region of interest.

Therefore, with respect to the similar medical images, a physician can observe the magnified corresponding regions of interest in approximately similar sizes. As a result, an occurrence of a situation where the corresponding region of interest in a part of the similar medical images is overlooked due to being magnified in a small size can be prevented and diagnostic accuracy can be improved.

A third aspect of the present disclosure is a control method of an information terminal which includes a display and is connected to a case retrieval system, the case retrieval system referring to a medical image database, in which medical images are registered, to retrieve a medical image, the display displaying an object medical image which is a medical image of a diagnostic interpretation object selected from diagnostic interpretation object candidates, disease name information not being set in additional information of the object medical image, the control method causing a computer of the information terminal to:

sense first specification information indicating a region of interest in the object medical image, receive NC number (where NC is an integer not less than 2) of similar medical images each having a prescribed degree of similarity with a feature quantity of a region of interest indicated by the first specification information from the case retrieval system in accordance with the region of interest, disease name information being set in additional information of the NC number of similar medical images, each of the received NC number of similar medical images including a corresponding region of interest that corresponds to the region of interest and including second specification information indicating the corresponding region of interest in each of the similar medical images;

display on the display a display screen including a first display region and a second display region, the first display region displaying the object medical image, the second display region displaying M number (where M is an integer not less than 1 and not more than NC) of similar medical images among the NC number of similar medical images, the second display region including ND number (where ND is an integer not less than M and not more than NC) of individual regions for displaying the M number of similar medical images; and when sensing one instruction for magnifying any one similar medical image among the M number of similar medical images, magnify the corresponding region of interest in each of the M number of or fewer similar medical images so as to match a position corresponding to a center of each of the individual regions in the second display region, and magnify each of the similar medical images at a magnification ratio, while maintaining a size of each of the individual regions at a same size, the magnification ratio being determined to bring a ratio of a size of the corresponding region of interest indicated by the second specification information to a size of each of the individual regions of the similar medical images to become a predetermined ratio.

A fourth aspect of the present disclosure is a control method of an information terminal which includes a display and is connected to a case retrieval system, the case retrieval system referring to a medical image database, in which medical images are registered, to retrieve a medical image, the display displaying an object medical image which is a medical image of one diagnostic interpretation object selected from diagnostic interpretation object candidates, disease name information not being set in additional information of the object medical image, the control method causing a computer of the information terminal to:

sense first specification information indicating a region of interest in the object medical image;

receive NC number (where NC is an integer not less than 2) of similar medical images each having a prescribed degree of similarity with a feature quantity of the region of interest indicated by the first specification information from the case retrieval system in accordance with the region of interest, disease name information being set in additional information of the NC number of similar medical images, each of the received NC number of similar medical images including a corresponding region of interest that corresponds to the region of interest and including second specification information indicating the corresponding region of interest in each of the similar medical images;

display on the display a display screen which includes a first display region and a second display region, the first display region displaying the object medical image, the second display region displaying M number (where M is an integer not less than 1 and not more than NC) of similar medical images among the NC number of similar medical images, the second display region including ND number (where ND is an integer not less than M and not more than NC) of individual regions for displaying the M number of similar medical images, the display screen including one or more instruction buttons, which are common to the M number of similar medical images, for changing a display size of the M number of similar medical images; and when sensing one instruction using the one or more instruction buttons, change a display size of each corresponding region of interest that is included in the M number of similar medical images while maintaining a size of each of the individual regions in the second display region at a same size, and magnify each of the similar medical images at a magnification ratio, the magnification ratio being determined to bring a ratio of a size of the corresponding region of interest indicated by the second specification information to a size of each of the individual regions of the similar medical images to become a predetermined ratio.

Among the NC number of similar medical images, sizes of the corresponding regions of interest are not the same. This is due to factors such as differences in sizes of lesions included in the respective similar medical images and differences among physicians having assigned the corresponding regions of interest in the past.

Therefore, when magnifying the corresponding region of interest that is included in each of the similar medical images at a constant ratio, the magnified corresponding region of interest is relatively small when the corresponding region of interest is relatively small, and the magnified corresponding region of interest is relatively large when the corresponding region of interest is relatively large. In other words, even when the similar medical images are magnified, sizes of the magnified corresponding regions of interest vary.

According to the present aspect, for example, when the corresponding region of interest in each of the similar medical images is magnified so as to match a position corresponding to a center of each of the individual regions, each of the similar medical images is magnified at a magnification ratio, the magnification ratio being determined to bring a ratio of a size of the corresponding region of interest indicated by the second specification information to a size of each of the individual regions of the similar medical images to become a predetermined ratio.

Accordingly, when magnifying the similar medical images, sizes of the magnified corresponding regions of interest may be made approximately uniform based on a relationship with the size of each of the individual regions.

Therefore, with respect to the similar medical images, a physician can observe the magnified corresponding regions of interest in approximately similar sizes. As a result, an occurrence of a situation where the corresponding region of interest in a part of the similar medical images is overlooked due to being magnified in a small size can be prevented and diagnostic accuracy can be improved.

In addition, in the first to fourth aspect described above, for example, the control method may cause the computer of the information terminal to:

transmit information indicating the feature quantity of the region of interest to the case retrieval system; and receive the similar medical image having the prescribed degree of similarity with the feature quantity of the region of interest from the case retrieval system.

In addition, in the first to fourth aspect described above, for example, the control method may cause the computer of the information terminal to:

transmit the object medical image and specification information indicating the region of interest to the case retrieval system; and receive, from the case retrieval system, the similar medical image having the prescribed degree of similarity with the feature quantity of the region of interest obtained from the object medical image and the specification information.

In addition, in the first to fourth aspect described above, for example, the object medical image may be a medical image of a lung, the similar medical image may be a medical image of a lung, the second display region may include first distribution information for selecting a similar medical image in which a size of the corresponding region of interest belongs to a prescribed first range, the first range indicating that the size of the corresponding region of interest is wider than a prescribed range in a region of the lung, second distribution information for selecting a similar medical image in which the size of the corresponding region of interest belongs to a prescribed second range, the second range being lower than the first range and indicating that the size of the corresponding region of interest is a part of a region of the lung, and third distribution information for selecting a similar medical image in which the corresponding region of interest includes a pleura, and when selection of any one of the first to third distribution information is sensed, a similar medical image corresponding to the selected distribution information may be selected and displayed in the second display region.

According to the present aspect, ND number of similar medical images that are displayed in the second display region can be further sorted based on a distribution type of the corresponding region of interest. Accordingly, for example, a similar medical image representing a symptom that is similar to the region of interest included in the object medical image can be efficiently selected from a large number of displayed similar medical images.

In addition, in the first to fourth aspect described above, for example, when selection of the first distribution information is sensed, a similar medical image corresponding to the first distribution information may be displayed in a corresponding individual region at an initial display size, when selection of the second distribution information is sensed, a similar medical image corresponding to the second distribution information may be magnified and displayed in a corresponding individual region so as to be centered on the corresponding region of interest in the similar medical image corresponding to the second distribution information, and when selection of the third distribution information is sensed, a similar medical image corresponding to the third distribution information may be magnified and displayed in a corresponding individual region in a state where the pleura is included so as to be centered on the corresponding region of interest in the similar medical image corresponding to the third distribution information.

According to the present aspect, when sorting similar medical images based on a distribution type of the corresponding region of interest, the similar medical images are not only sorted but also displayed in accordance with the distribution type. Accordingly, after sorting similar medical images based on a distribution type of the corresponding region of interest, the operator is not required to separately perform a process for magnifying a similar medical image in accordance with the distribution type, centering the similar medical image on the corresponding region of interest, or the like. Therefore, even when a large number of similar medical images are sorted based on a distribution type of the corresponding region of interest, the hassle of repetitively performing a similar operation on each of the large number of sorted similar medical images can be significantly reduced. As a result, interruptions of the thought or concentration of a physician that is best focused on making a medical judgment by the hassle of performing operations can be significantly reduced and the thought or concentration of the physician can be directed towards making a medical judgment as it should be. Thus, accuracy of medical judgment can be improved.

In addition, in the first to fourth aspect described above, for example, the first distribution information may be information indicating a distribution belonging to a bilateral, a multiple, a diffuse, or a hematogenous category, the second distribution information may be information indicating a distribution belonging to a segmental or a bronchial category, and the third distribution information may be information indicating a distribution belonging to a subpleural category.

According to the present aspect, in a case of a distribution belonging to a bilateral, a multiple, a diffuse, or a hematogenous category, a similar medical image is displayed in an initial display size. In a case of a distribution belonging to a segmental or a bronchial category, a similar medical image is magnified and displayed. In a case of a distribution belonging to a subpleural category, a similar medical image is magnified and displayed in a state where the pleura is included.

In a case of a distribution belonging to a bilateral, a multiple, a diffuse, or a hematogenous category, it is likely that a lesion site has spread throughout a lung or that a lesion site has occurred in a wide area of a lung. Therefore, there is a need from a medical perspective to display a similar medical image in an initial display size or, in other words, without magnification.

On the other hand, in a case of a distribution belonging to a segmental or a bronchial category, such likelihood is low. Therefore, by magnifying and displaying a similar medical image when a distribution belonging to a segmental or a bronchial category is selected, a step of magnifying and displaying an image can be omitted and the concentration of a physician can be prevented from being interrupted. In addition, in a case of a distribution belonging to a subpleural category, a positional relationship between the pleura and the lesion site is an important indicator for diagnosis. Therefore, there is a need from a medical perspective to magnify to display a similar medical image in a state where the pleura is included.

First Embodiment

Hereinafter, an embodiment of the present disclosure will be described with reference to the drawings. Moreover, in the respective drawings, like symbols are used for like components.

FIG. 1 is an overall configuration diagram of a hospital information system to which an information terminal according to a present embodiment is applied. As shown in FIG. 1, the hospital information system includes an information terminal 100, a medical information management system 200, and a case retrieval system 300.

The information terminal 100, the medical information management system 200, and the case retrieval system 300 are connected so as to be capable of communicating with each other via a network 400.

The medical information management system 200 and the case retrieval system 300 need not necessarily be arranged inside a hospital and may be software that runs at a data center or on a private cloud server, a public cloud server or the like outside of the hospital. When the medical information management system 200 and the case retrieval system 300 are installed inside a hospital, a local area network may be adopted as the network 400. As the local area network, an IEEE 802.3 series wired LAN, an IEEE 802.11 series wireless LAN, or a network that combines the two can be adopted. When the medical information management system 200 and the case retrieval system 300 are realized using servers outside a hospital, the Internet may be adopted as the network 400.

As the information terminal 100, an information terminal such as a personal computer or a tablet terminal is adopted. As the medical information management system 200, PACS (Picture Archiving and Communication Systems), an electronic medical chart system, or the like is adopted.

Figure 2:
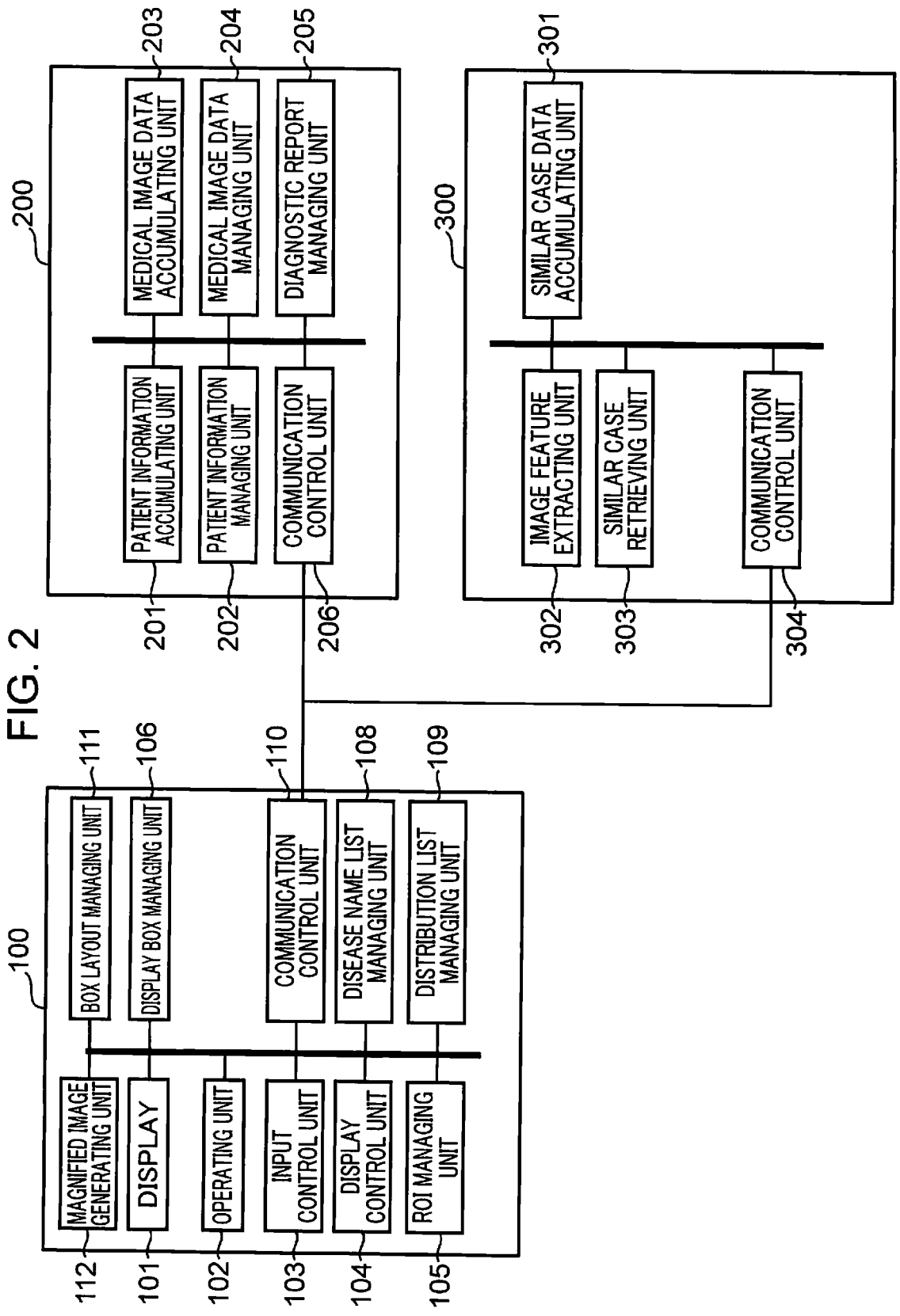
FIG. 2 is a block diagram showing configurations of an information terminal, a medical information management system, and a case retrieval system.

FIG. 2 is a block diagram showing configurations of the information terminal 100, the medical information management system 200, and the case retrieval system 300. As shown in FIG. 2, the information terminal 100 includes a display 101, an operating unit 102, an input control unit 103, a display control unit 104, an ROI managing unit 105, a display box managing unit 106, a disease name list managing unit 108, a distribution list managing unit 109, a communication control unit 110, a box layout managing unit 111, and a magnified image generating unit 112.

The display 101 is constituted by a liquid crystal monitor for example, displays a medical image and a medical chart image to be diagnosis objects and, at the same time, displays a report input image for entering a diagnosis result and the like. While at least one display 101 is required, normally, two to three displays 101 are used to perform image diagnosis. In the present embodiment, two displays 101 are used. One of the displays 101 will be referred to as a display 101a and the other display 101 will be referred to as a display 101b (refer to FIG. 3).

Figure 3:
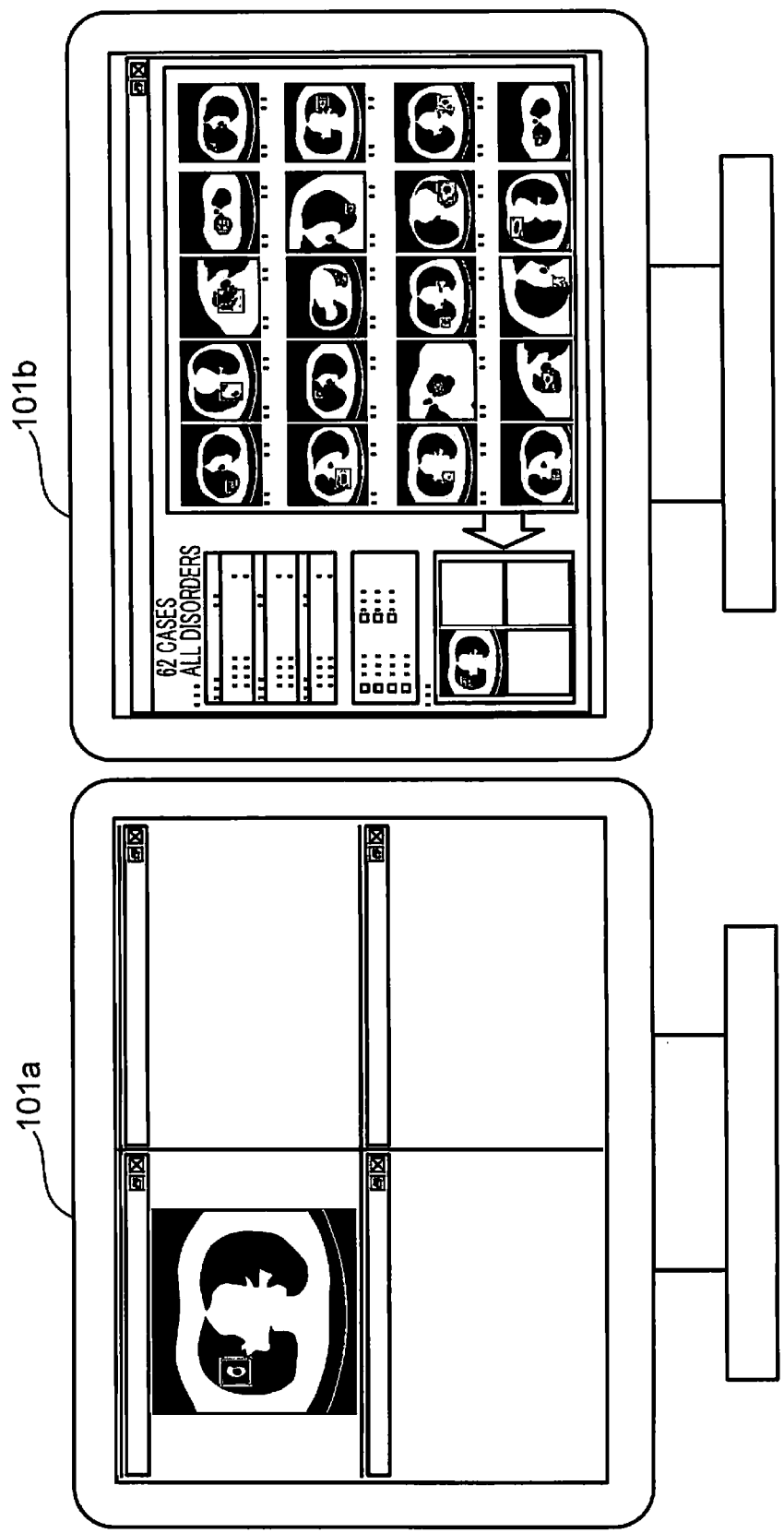
FIG. 3 is an external view of two displays.

FIG. 3 is an external view of the two displays 101a and 101b. In FIG. 3, four medical image viewers are displayed in a two-row, two-column arrangement on the display 101a and a screen of the case retrieval system 300 is displayed on the display 101b. Moreover, when only one display 101 is provided, the first display screen and the second display screen are displayed by dividing regions on the display screen of the one display 101.

The operating unit 102 includes, for example, a keyboard and a mouse and accepts various operations input by a user to the information terminal 100. For example, the operating unit 102 accepts operations by the user on a medical image and a medical chart image displayed on the display 101, operations for inputting a diagnosis result to a report input screen, and the like.

Upon sensing an operation by the user on the operating unit 102, the input control unit 103 interprets a content of the operation and notifies the operation content to other components. For example, the input control unit 103 senses a position of a mouse pointer on the display 101 from coordinate data output by a mouse as the operating unit 102 and causes the mouse pointer to be displayed on the display 101. In addition, if a GUI part (for example, a GUI button) generated by the display control unit 104 is displayed at a display position of the mouse pointer upon sensing that the mouse has been clicked, the input control unit 103 determines that the GUI has been selected by the user and notifies other components that the GUI has been selected by the user.

The display control unit 104 generates a GUI (Graphical User Interface) of the information terminal 100 and causes the GUI to be displayed on the display 101.

When performing a similar case retrieval, the ROI managing unit 105 generates region of interest information indicating a region of interest that is set with respect to a retrieval query image (to be described later) and stores the region of interest information in a memory, and manages the region of interest information.

The display box managing unit 106 stores display box management information 4410 (FIG. 36B) to be described later in a memory and manages the display box management information 4410.

The disease name list managing unit 108 generates a disease name list (FIG. 39) of similar cases displayed in a case display region 710 (FIG. 6) and stores the disease name list in a memory, and manages the disease name list.

The distribution list managing unit 109 generates a distribution list (FIG. 44A) representing a lesion distribution of similar cases displayed in the case display region 710 and stores the distribution list in a memory, and manages the distribution list.

The communication control unit 110 includes, for example, a communication apparatus for connecting the information terminal 100 to the network 400 and controls communication between the information terminal 100 and the medical information management system 200 and communication between the information terminal 100 and the case retrieval system 300. In addition, the communication control unit 110 accepts transmission requests of various types of data from other blocks and transmits the data to the medical information management system 200 or the case retrieval system 300, and receives data transmitted from the medical information management system 200 or the case retrieval system 300 and hands over the data to a corresponding block.

The box layout managing unit 111 generates layout management information 4200 (FIG. 36E) to be described later and stores the layout management information 4200 in a memory, and manages the layout management information 4200.

The magnified image generating unit 112 generates a magnified image of a thumbnail image of a similar case. The magnified image generating unit 112 acquires an amount of operation by the user with respect to the operating unit 102 from the input control unit 103. The magnified image generating unit 112 receives, from the communication control unit 110, similar case data (including a degree of similarity and region of interest information) transmitted from the case retrieval system 300. The magnified image generating unit 112 calculates a different magnification ratio for each thumbnail image only with respect to the number of cases to be displayed in the case display region 710 among the number (NC number for example) of similar cases acquired by similar case retrieval and generates magnified images corresponding to the number of cases to be displayed.

As shown in FIG. 2, the medical information management system 200 includes a patient information accumulating unit 201, a patient information managing unit 202, a medical image data accumulating unit 203, a medical image data managing unit 204, a diagnostic report managing unit 205, and a communication control unit 206.

The patient information accumulating unit 201 accumulates patient information 1000 (FIG. 26) in which personal information of a patient such as gender and age, clinical information of the patient such as medical history, and examination information of the patient such as a blood test are registered.

With respect to the patient information 1000 (FIG. 26) accumulated in the patient information accumulating unit 201, the patient information managing unit 202 executes a process for registering data input by the user and updating the patient information 1000, a process for outputting the patient information 1000 to the display control unit 104, and the like, and manages the patient information 1000. The medical image data accumulating unit 203 accumulates medical image data that represents examination images of a patient.

The medical image data managing unit 204 accumulates medical image data in the medical image data accumulating unit 203 and manages the medical image data.

The diagnostic report managing unit 205 manages a diagnostic report 3000 (FIG. 29) that represents a diagnosis result by a physician with respect to respective examinations performed on a patient.

The communication control unit 206 includes, for example, a communication apparatus for connecting the medical information management system 200 to the network 400, accepts transmission requests of various types of data from other blocks and transmits the data to the information terminal 100 or the case retrieval system 300, and receives data transmitted from the information terminal 100 or the case retrieval system 300 and hands over the data to a corresponding block.

As shown in FIG. 2, the case retrieval system 300 includes a similar case data accumulating unit 301, an image feature extracting unit 302, a similar case retrieving unit 303, and a communication control unit 304.

The similar case data accumulating unit 301 accumulates, in advance, similar case data 4000 (FIG. 30) in which image features extracted from a large number of similar cases selected as object data of similar case retrieval among similar cases managed by the medical information management system 200, thumbnail images generated from the large number of similar cases, and the like are registered.

The image feature extracting unit 302 extracts an image feature in region of interest information of a retrieval query image transmitted from the communication control unit 110 of the information terminal 100.

In this case, the region of interest information is an example of the specification information indicating the region of interest.

The similar case retrieving unit 303 generates a similar case retrieval result by respectively comparing the image feature extracted by the image feature extracting unit 302 and image features of one or more similar cases accumulated in the similar case data accumulating unit 301.

The communication control unit 304 includes, for example, a communication apparatus for connecting the case retrieval system 300 to the network 400, accepts transmission requests of various types of data from other blocks and transmits the data to the information terminal 100 or the medical information management system 200, and receives data transmitted from the information terminal 100 or the medical information management system 200 and hands over the data to a corresponding block.

Figure 4:
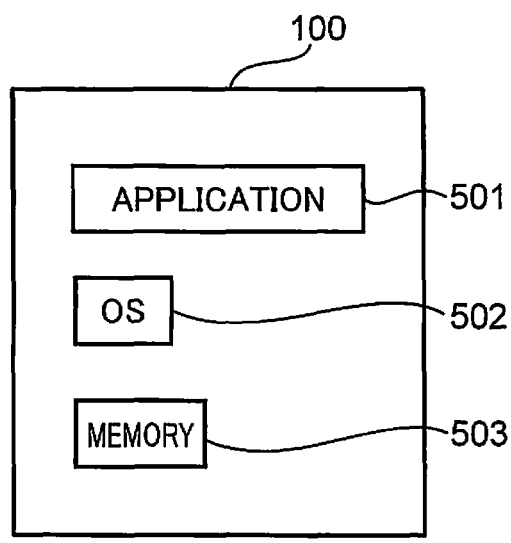
FIG. 4 is a diagram showing a configuration example of an implementation of an information terminal.

FIG. 4 is a diagram showing a configuration example of an implementation of the information terminal 100. As shown in FIG. 4, the information terminal 100 includes an application 501, an OS (Operating System) 502, a memory 503, and other hardware not shown.

The application 501 is application software for causing a personal computer or a tablet terminal to function as the information terminal 100 and is executed by a processor of the information terminal 100. The information terminal 100 may implement the application 501 by reading the application 501 from a computer-readable recording medium or may implement the application 501 by downloading the application 501 from a network.

In this case, the application 501 includes a medical information management application and a similar case retrieval application. The medical information management application is an application for causing the information terminal 100 to work in cooperation with the medical information management system 200 and the similar case retrieval application is an application for causing the information terminal 100 to work in cooperation with the case retrieval system 300. In addition, both applications transmit and receive data to and from each other and integrate services provided by the medical information management system 200 and the case retrieval system 300 in the information terminal 100.

The OS 502 is basic software of the information terminal 100 and is executed by a processor of the information terminal 100. The memory 503 is constituted by a storage apparatus such as a RAM or a ROM included in the information terminal 100 and stores a group of data included in the application 501.

As the processor of the information terminal 100 executes the application 501, functions of the input control unit 103, the display control unit 104, the ROI managing unit 105, the display box managing unit 106, the disease name list managing unit 108, the distribution list managing unit 109, the communication control unit 110, the box layout managing unit 111, and the magnified image generating unit 112, which are shown in FIG. 2, are realized.

However, in the present embodiment, the information terminal 100 may be only mounted with the application 501, mounted with the application 501 and the OS 502, mounted with the application 501, the OS 502, and the memory 503, or mounted with the application 501, the OS 502, the memory 503, and other hardware not illustrated. The information terminal 100 according to the present embodiment can be realized by any of the implementations.

Figure 5:
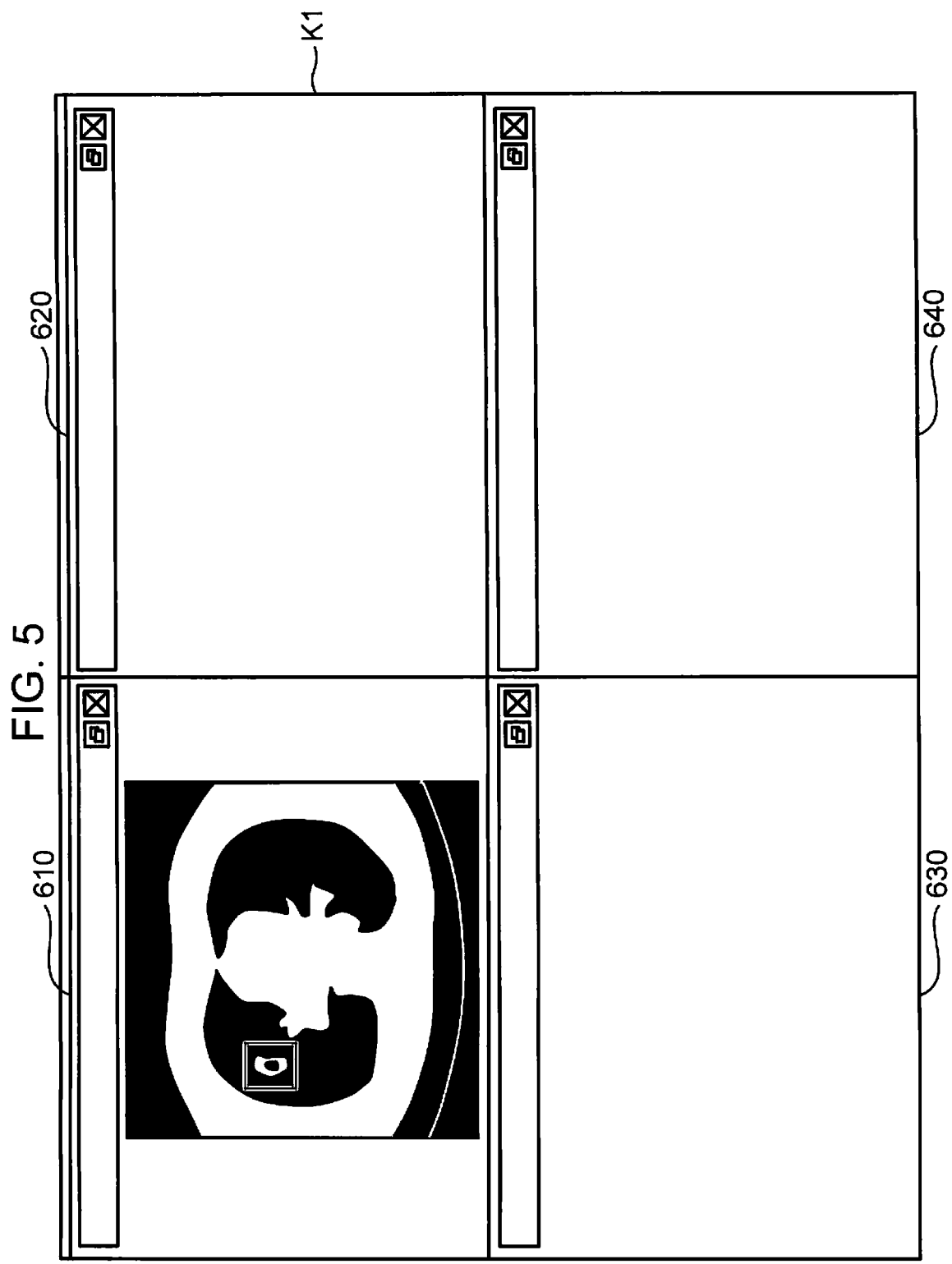
FIG. 5 is a diagram showing an example of a basic screen that is displayed on a display immediately after starting a similar case retrieval application on an information terminal.

FIG. 5 is a diagram showing an example of a basic screen K1 that is displayed on a display 101a immediately after starting the similar case retrieval application on the information terminal 100. The basic screen K1 shown in FIG. 5 is constituted by four medical image viewers 610 to 640. A medical image is normally recorded in a DICOM (Digital Imaging and Communication in Medicine) format and the medical image viewers 610 to 640 are viewers capable of handling DICOM. A medical image handled in the present embodiment is assumed to be a chest CT image that is constituted by a large number of tomographic images (hereinafter, referred to as slice images) in the DICOM format. However, this is simply an example and CT images of another site (for example, the head, the abdomen, a leg, and an arm) may be adopted instead.

In a chest CT image displayed on the medical image viewers 610 to 640, slice images are switched by an operation of a mouse or a keyboard. In this case, the slice images constituting a chest CT image are arranged in an order from, for example, the neck toward the abdomen.

For example, when a mouse pointer is positioned on the medical image viewer 610 and a rotation of a mouse wheel is sensed by the input control unit 103, the display control unit 104 switches a slice image that is displayed on the medical image viewer 610 in accordance with an amount of the sensed rotation. For example, when the mouse wheel is rotated by one click toward the rear of the mouse on the medical image viewer 610, the display control unit 104 switches a slice image being displayed to a slice image at a next slice position. On the other hand, for example, when the mouse wheel is rotated by one click toward the front of the mouse on the medical image viewer 610, the display control unit 104 switches a slice image being displayed to a slice image at an immediately previous slice position. Therefore, a user such as a physician switches slice images displayed on the medical image viewer 610 as appropriate by rotating the mouse wheel forward or backward to retrieve a desired slice image.

Moreover, as the medical image, an MRI (Magnetic Resonance Imaging) image or a plain radiographic image may be adopted instead of a chest CT image. In addition, while the number of medical image viewers is set to four in the example shown in FIG. 5, this is simply an example and another number such as six and eight may be adopted instead. While an increase in the number of medical image viewers increases the number of images that can be simultaneously compared, a display area per image decreases. Therefore, for the number of medical image viewers, a configuration that can be appropriately modified in accordance with a display size of the display 101a may be adopted. In this case, it is assumed that the number of medical image viewers can be changed at will by a user or an administrator.

Before the similar case retrieval application is started, a slice image of a chest CT image of a patient is displayed across an entire region of the display 101a. In addition, in this state, as the similar case retrieval application is started by a user such as diagnostic interpreter, the slice image that had been displayed across the entire region of the display 101a is displayed on the medical image viewer 610.

In other words, when the user starts the similar case retrieval application, a retrieval query image that had been displayed across the entire region of the display 101a is initially displayed on the medical image viewer 610. Moreover, the display control unit 104 may display a region of interest (ROI) that is an object of similar case retrieval so as to overlap with the retrieval query image. A retrieval query image is an example of the object medical image which is the medical image of the diagnostic interpretation object.

In FIG. 5, while no images are displayed on the other medical image viewers 620 to 640, when there are a plurality of examination images of a patient that are diagnosis objects and a plurality of examination images are displayed on the display 101a before the similar case retrieval application is started, the display control unit 104 may display the plurality of examination images without modification on the medical image viewers 620 to 640.

Figure 6:
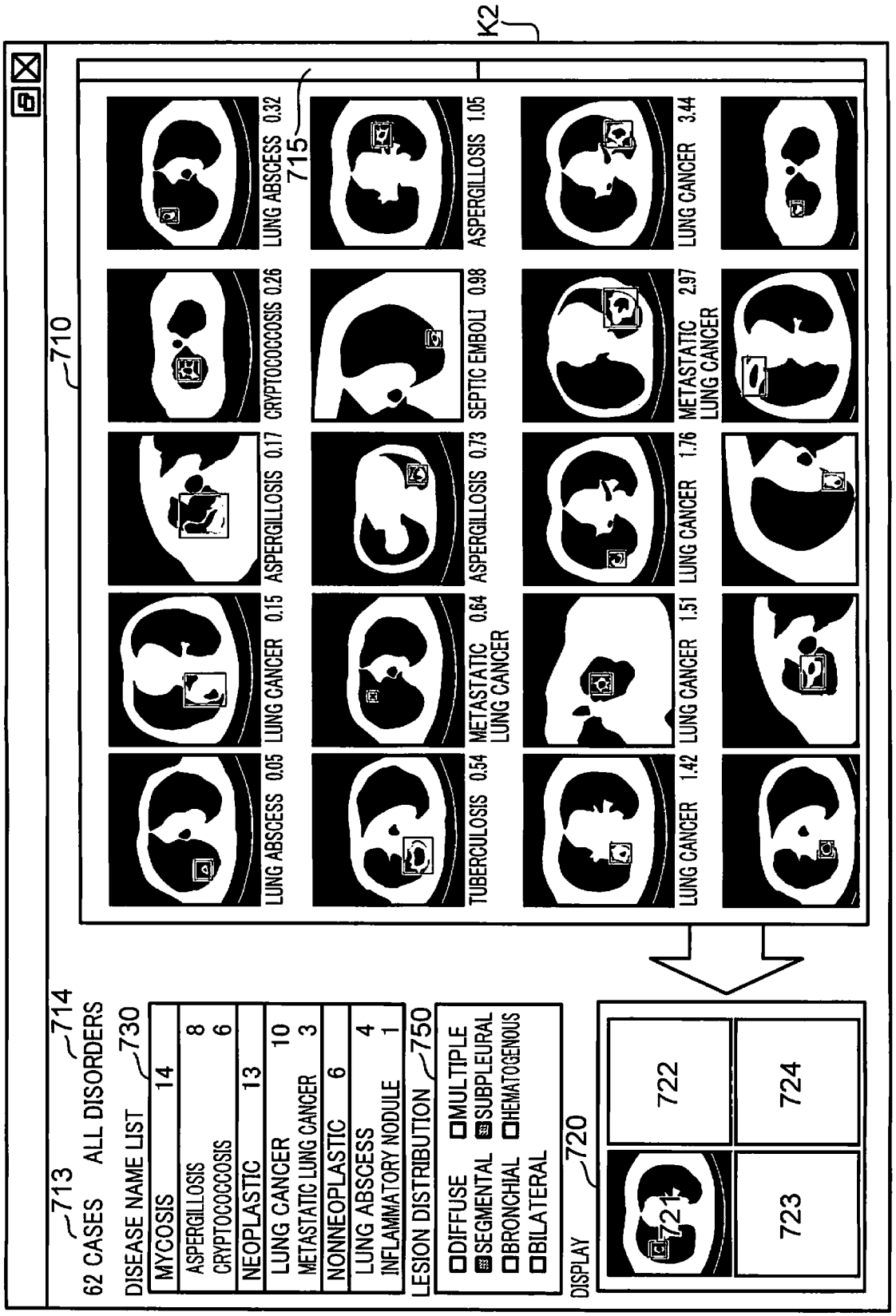
FIG. 6 is a diagram showing an example of a basic screen that is displayed on a display immediately after starting a similar case retrieval application on an information terminal.

FIG. 6 is a diagram showing an example of a basic screen K2 that is displayed on a display 101b immediately after starting the similar case retrieval application on the information terminal 100. The basic screen K2 shown in FIG. 6 includes a case display region 710, a layout region 720, a disease name list display region 730, and a distribution list display region 750. Moreover, the layout region 720 is an example of the first display region and the case display region 710 is an example of the second display region.

The case display region 710 is a region for displaying thumbnail images of similar cases that are similar to the retrieval query image in an order of degrees of similarity. In this case, the thumbnail image of the similar case is an example of the similar medical image.

Since a large number of similar cases are displayed in the case display region 710, performing a conversion of resolution or a pixel value in the case display region 710 results in an extended processing time. Therefore, thumbnail images are created in advance from original slice images and saved in the case retrieval system 300.

Hereinafter, additional explanation of a conversion of resolution or a pixel value will be provided. While the resolution of an original slice image is 512×512 pixels, since the resolution of a thumbnail image is much lower, resolution conversion must be performed. In consideration thereof, a thumbnail image is generated by performing a low resolution process and a gradation conversion process on an original slice image.

For example, a gradation conversion process is performed as follows. In a slice image acquired by CT, each pixel value (CT value) takes a value of 2000 grayscale ranging from −1000 to +1000 (in HU: Hounsfield Units) and cannot be displayed as-is on an ordinary 8-bit grayscale display. In addition, even if the image can be displayed, it is difficult for a person to distinguish a pulmonary emphysema region (CT value: −1000 HU), a normal lung field tissue (CT value: about −900 HU), a ground-glass region (CT value: −800 HU), a soft tissue (CT value: −100 to −50 HU), water (CT value: 0 HU), and bone (CT value: 1000 HU) among 2000 grayscale with the naked eye.

Therefore, normally, with a slice image, a window level and a window width are set with respect to each pixel value, the pixel value is reconstructed into an 8-bit pixel value, and the slice image is displayed on the display. In this case, a window level represents a CT value at a center of a window and a window width represents a vertical width of the center of the window.

For example, when a DICOM image is reconstructed in a lung window setting, the window level is set to −550 to −800 and the window width is set to 1000 to 1600. Therefore, a thumbnail image is also generated by reducing a pixel value to 8 bits from an original slice image with the process described above.

Moreover, the thumbnail image displayed in the case display region 710 is a thumbnail image representing a similar case whose distance from a feature vector of a diagnosis object case is equal to or less than a predetermined threshold. In this case, for example, a Euclidean distance is used as the distance. Alternatively, a different distance scale such as a city block distance may be adopted as the distance. The closer the distance between two comparison object images, the more similar. In addition, as the feature vector, a feature vector obtained not from a thumbnail image but from a DICOM image that is an original image is adopted.

Figure 7:
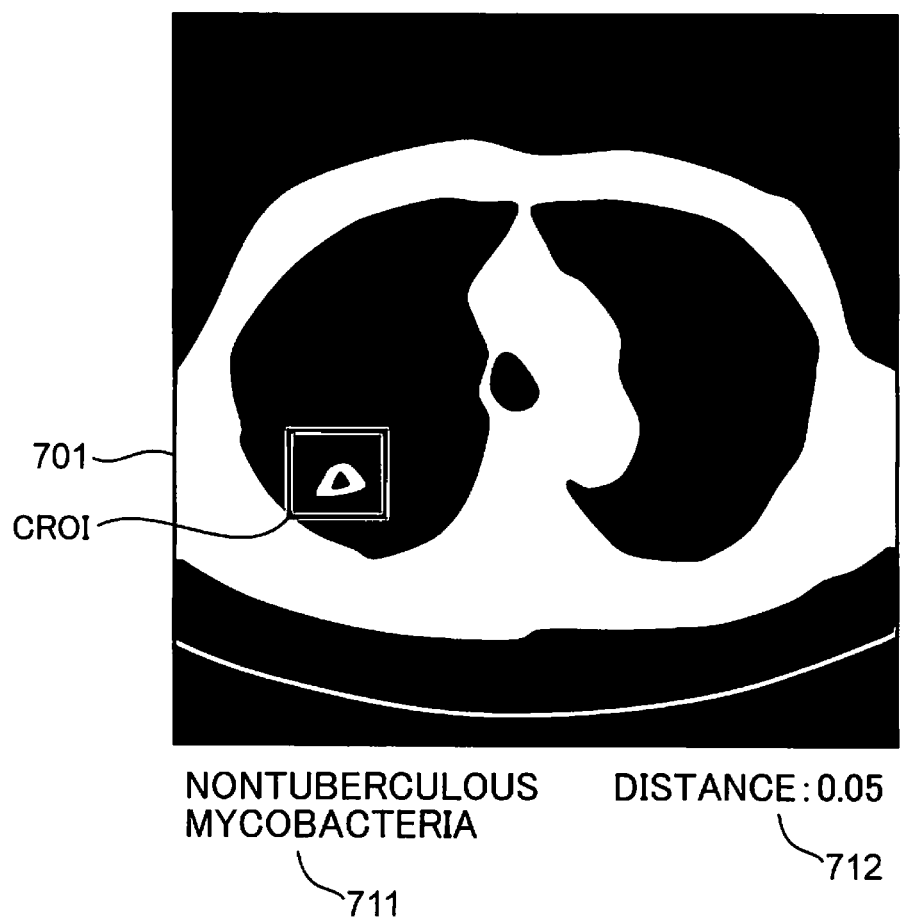
FIG. 7 is an extracted view showing a display region of one similar case that is displayed in a case display region.

FIG. 7 is an extracted view showing a display region 701 (an example of the individual region) of one similar case that is displayed in the case display region 710. A thumbnail image is displayed in the display region 701 of the similar case and a definitively diagnosed disease name display region 711 and a distance display region 712 are arranged below the thumbnail image. A definitively diagnosed disease name of a similar case that is an object is displayed in the definitively diagnosed disease name display region 711. A definitively diagnosed disease name refers to a disease name representing a finalized diagnosis of a similar case that is an object. The distance display region 712 displays a distance between a feature vector of a slice image of a similar case that is an object and a feature vector of a retrieval query image. In the example shown in FIG. 7, since "nontuberculous mycobacteria" is displayed in the definitively diagnosed disease name display region 711, the thumbnail image is a thumbnail image of a similar case that has been definitively diagnosed as "nontuberculous mycobacteria". In addition, since "0.05" is displayed in the distance display region 712, it is shown that a distance between the slice image of the similar case and the retrieval query image is "0.05".

As shown in FIG. 7, a thumbnail image that is displayed in the display region 701 of a similar case includes a corresponding region of interest CROI. The corresponding region of interest CROI is a region corresponding to a region of interest (in other words, a region similar to a region of interest) that is set in a retrieval query image (a medical image of a diagnostic interpretation object). It should be noted that, hereinafter, a corresponding region of interest will also be simply referred to as a "region of interest".

Returning now to FIG. 6, a number of retrieved results display region 713 is arranged in a top left part of the basic screen K2, for example. The number of retrieved results display region 713 displays the number of similar cases which are similar to the diagnosis object case as acquired from the case retrieval system 300 as a result of a retrieving process.

Moreover, when the number of similar cases is significantly large, the case display region 710 cannot display all similar cases at the same time. In consideration thereof, a scroll bar 715 that is elongated in a vertical direction is provided on the right side of the case display region 710, for example. The display control unit 104 displays a thumbnail image displayed in the case display region 710 by scrolling the thumbnail image in a vertical direction in accordance with an amount of movement of the scroll bar 715. Accordingly, the user can display a similar case previously in a non-displayed state in the case display region 710 and observe the similar case.

Moreover, the scroll bar 715 may be elongated in a horizontal direction. In this case, the display control unit 104 may display a thumbnail image displayed in the case display region 710 by scrolling the thumbnail image in a horizontal direction in accordance with an amount of movement of the scroll bar 715.

Moreover, while the information terminal 100 is configured to acquire a thumbnail image whose distance from a retrieval query image is equal to or less than a predetermined threshold from the case retrieval system 300, this is simply an example. For example, the information terminal 100 may always acquire a constant number of thumbnail images from the case retrieval system 300 in a descending order of degrees of similarity. Alternatively, the information terminal 100 may acquire thumbnail images from the case retrieval system 300 so as to always include a constant number of thumbnail images representing a given definitively diagnosed disease name.

Moreover, as a method of displaying thumbnail images in the case display region 710, a display method can be adopted which involves displaying a thumbnail image whose distance from a retrieval query image is shortest at a left end of an uppermost row, displaying thumbnail images so that distances sequentially increases rightward, and once reaching a right end of the same row, displaying a thumbnail image with a next longer distance at a left end of a second-from-top row, for example. In other words, a display method can be adopted which involves displaying thumbnail images in an ascending order of distances so as to meander from top left to bottom right in the case display region 710.

Obviously, the present embodiment may adopt other display methods. For example, a display method can be adopted which involves displaying a thumbnail image whose distance is shortest at an upper end of a leftmost column, displaying thumbnail images so that distances sequentially increases downward, and once reaching a lower end of the same column, displaying a thumbnail image with a next longer distance at an upper end of a second-from-left column. In addition, a configuration may be adopted in which the user can switch among the plurality of display methods.

Furthermore, while distance is adopted as a degree of similarity in the example described above, any indicator such as cosine similarity may be adopted as long as the indicator represents a degree of similarity between images. When cosine similarity is adopted, the degree of similarity between two images that are comparison objects increases as the value approaches 1.

Moreover, while details will be provided later, similar cases displayed in the case display region 710 can be narrowed down by a disease name displayed in the disease name list display region 730 or by a lesion distribution displayed in the distribution list display region 750. A currently set narrowing condition of similar cases is displayed in a display condition display region 714. Since the example shown in FIG. 6 shows a state immediately after similar case retrieval and the similar cases have not been narrowed down in any way, "all disorders" are displayed in the display condition display region 714.

The thumbnail image of a similar case that is displayed in the case display region 710 is configured to be able to be magnified by an operation by the user. Hereinafter, magnification and display of a thumbnail image of a similar case will be described.

Figure 8:
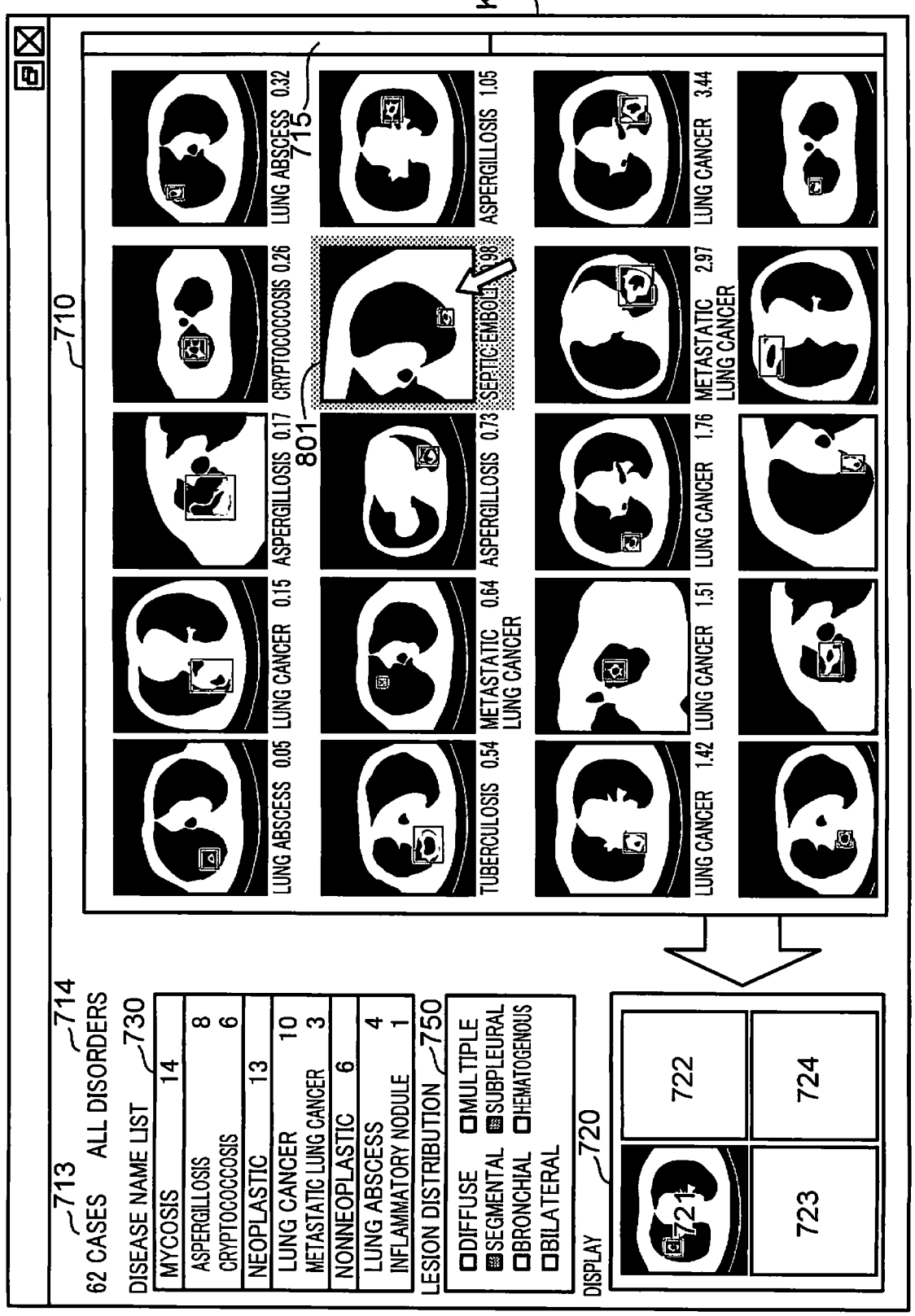
FIG. 8 is a diagram showing a basic screen when one thumbnail image is selected among thumbnail images displayed in a case display region.

FIG. 8 is a diagram showing the basic screen K2 when one thumbnail image among the thumbnail images displayed in the case display region 710 is selected. As shown in FIG. 8, in a state where the basic screen K2 immediately after a similar case retrieval is displayed, entire thumbnail images are displayed in each display region. The case display region 710 includes a prescribed number ND (ND=20 in the present embodiment) of display regions, each of which displays a thumbnail image.

The input control unit 103 of the information terminal 100 constantly monitors input made via the operating unit 102 that is a mouse or the like. In addition, the input control unit 103 senses that an operation for clicking the mouse is input by the user and that the operation causes one thumbnail image of a similar case displayed in the case display region 710 to be selected. As a result, the display control unit 104 changes a color of a background of the selected thumbnail image.

In the example shown in FIG. 8, in the case display region 710, a thumbnail image of a similar case displayed in the 2nd-row, 4th-column display region 801 has been selected. Therefore, the color of the background of the thumbnail image in the display region 801 has been changed. Specifically, a color of a frame-like region that encloses an outer periphery of the selected thumbnail image has been changed. Accordingly, the user can be notified that the thumbnail image has changed to a selected state.

In this case, as the color of the background, for example, a color that clearly differs from a color of a background of the case display region 710 is adopted. In the example shown in FIG. 8, for example, yellow is adopted. Moreover, while a mode in which the color of a frame-like region of a thumbnail image is changed has been shown in the example in FIG. 8, a mode in which the frame-like region blinks or a mode in which brightness of the frame-like region is increased may be adopted instead.

When the user performs a magnification operation by, for example, rotating a wheel of the mouse in a state where one of the thumbnail images is selected as shown in FIG. 8, the input control unit 103 senses an amount of rotation of the wheel of the mouse and notifies the magnified image generating unit 112 of the sensed amount of rotation. As a result, for example, the magnified image generating unit 112 decides a magnification ratio based on the sensed amount of rotation and magnifies the thumbnail image at the decided magnification ratio. The display control unit 104 displays the thumbnail image magnified by the magnified image generating unit 112 in the case display region 710.

Figure 9:
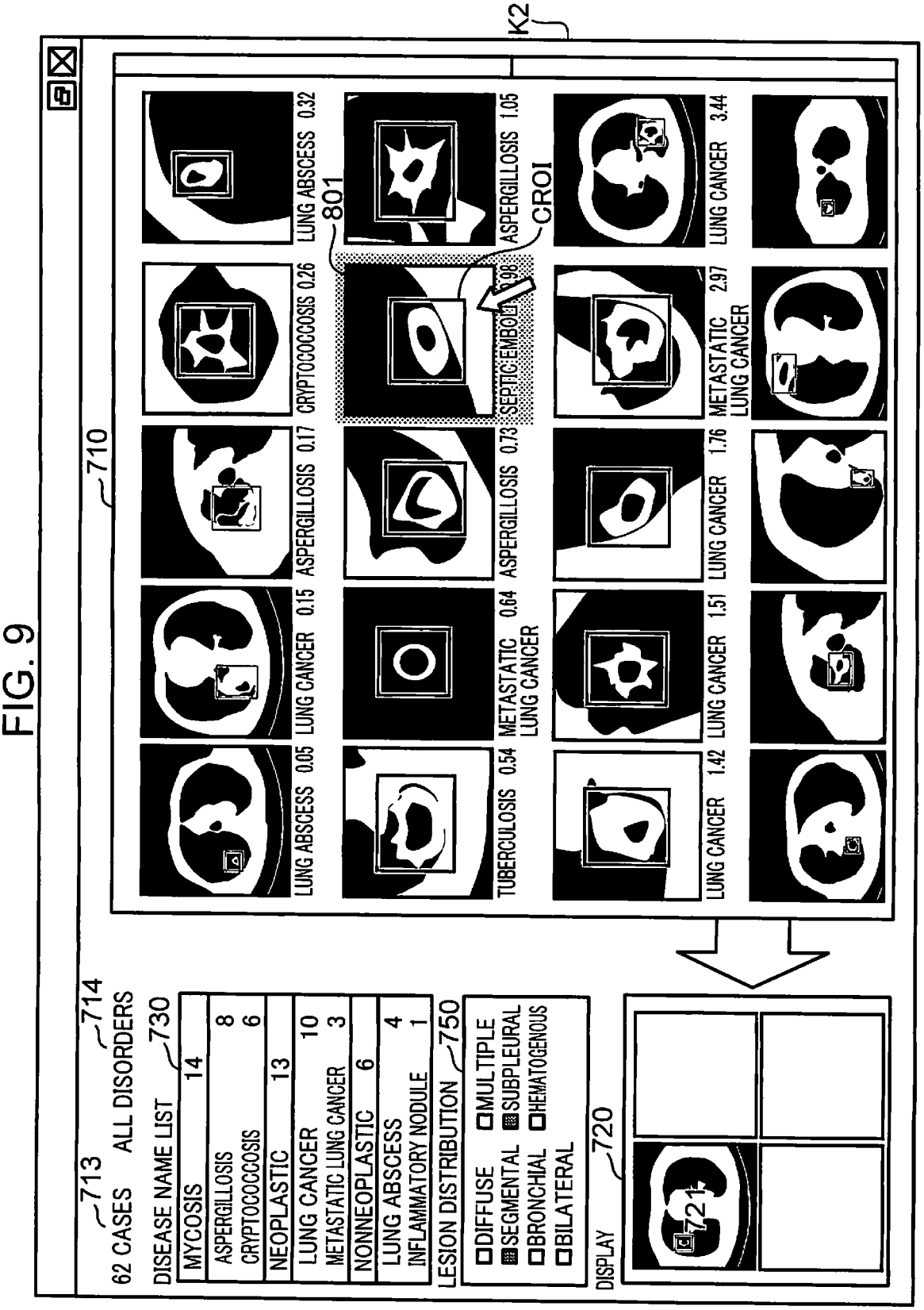
FIG. 9 is a diagram showing a basic screen when a part of thumbnail images that are displayed in a case display region is magnified.

FIG. 9 is a diagram showing the basic screen K2 when a part of thumbnail images that are displayed in the case display region 710 is magnified. Specifically, in FIG. 9, not only the selected thumbnail image but a total of 11 thumbnail images from a thumbnail image (1st-row, 4th-column) adjacent to the above of the selected thumbnail image to a thumbnail image (3rd-row, 4th-column) adjacent to below of the selected thumbnail image are magnified in an order of lateral arrangement. Accordingly, compared to a case where all of the thumbnail images of similar case data of 62 cases received from the case retrieval system 300 are magnified, the processing burden on the information terminal 100 can be reduced significantly.

Moreover, when magnifying the displayed thumbnail image, the magnified image generating unit 112 generates a magnified image so that a center position of the corresponding region of interest CROI matches a center position of the display region 801 as shown in FIG. 9. In addition, when magnifying the thumbnail image, the display control unit 104 does not increase the size of the display region 801 and maintains the display region 801 at a same size as shown in FIG. 9.

Furthermore, the magnified image generating unit 112 may set magnification ratios to different values for each thumbnail image. Accordingly, as shown in FIG. 9, magnification can be performed so that the respective thumbnail images after magnification are in the same size.

In FIG. 9, thumbnail images of M number (M=20 in FIG. 9) of similar cases are displayed in the case display region 710 that is capable of displaying a maximum number ND (ND=20 in the present embodiment) of cases, and M number of or fewer thumbnail images (11 in FIG. 9) are magnified.

Figure 10:
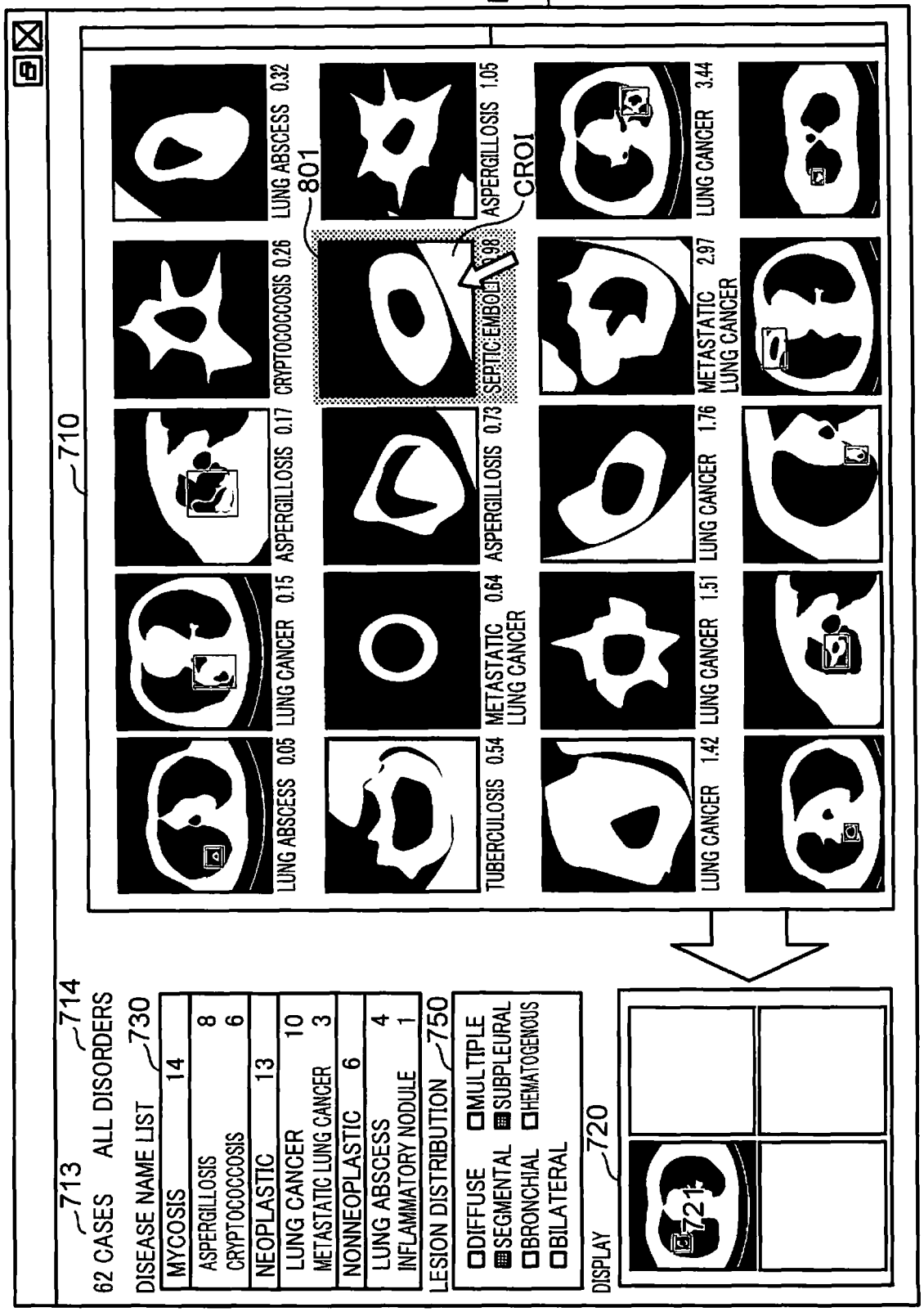
FIG. 10 is a diagram showing a basic screen when a part of thumbnail images that are displayed in a case display region is magnified which differs from the basic screen shown in FIG. 9.

FIG. 10 is a diagram showing the basic screen K2 when a part of thumbnail images that are displayed in the case display region 710 is magnified which differs from the basic screen K2 shown in FIG. 9. In FIG. 10, the magnified image generating unit 112 magnifies a total of 11 thumbnail images from a thumbnail image (1st-row, 4th-column) adjacent to the above of the selected thumbnail image to a thumbnail image (3rd-row, 4th-column) adjacent to below of the selected thumbnail image in an order of lateral arrangement. In addition, the magnified image generating unit 112 magnifies the 11 thumbnail images so that the size of the corresponding region of interest CROI matches the size of the display region 801.

Figure 11:
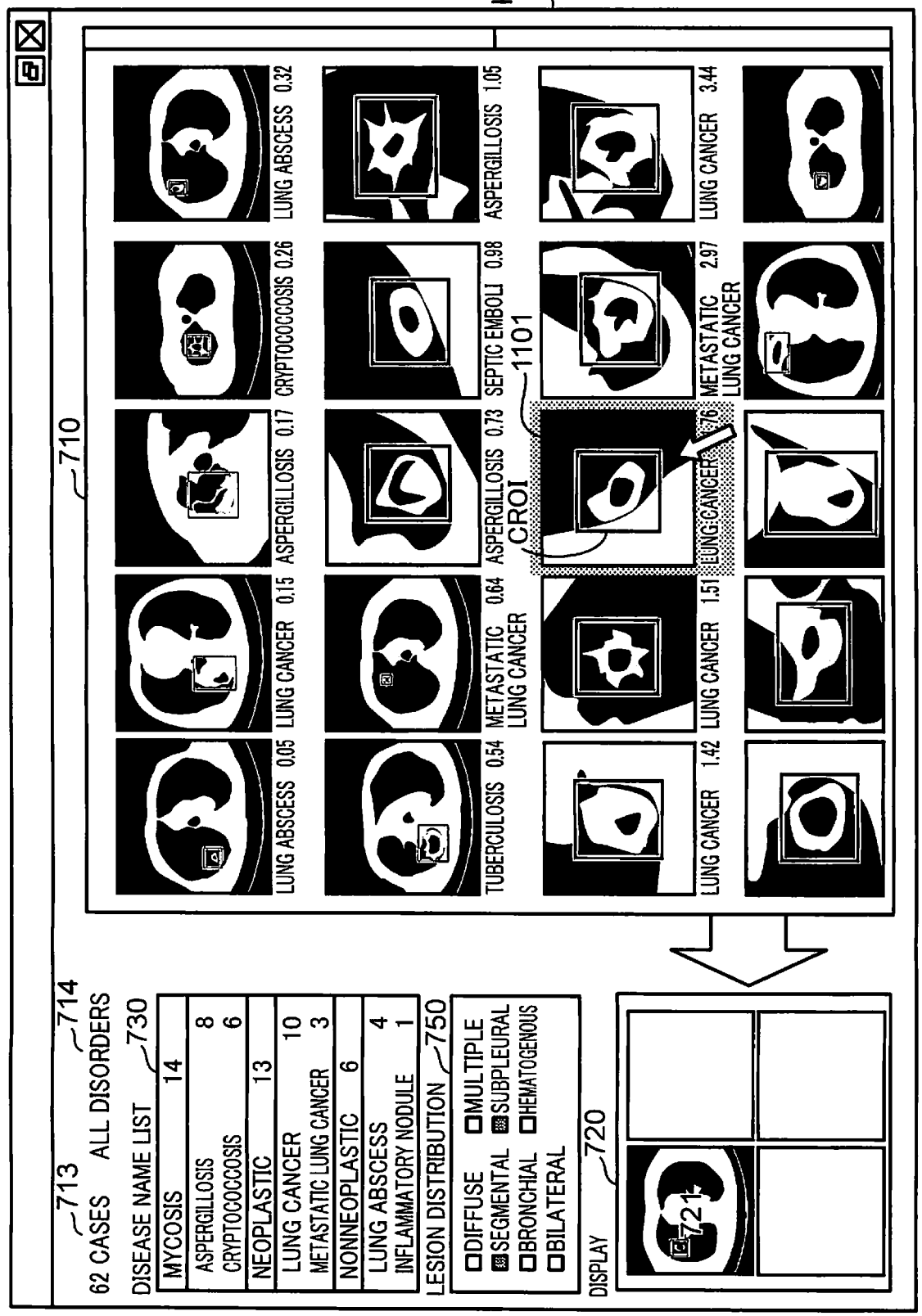
FIG. 11 is a diagram showing a basic screen when a part of thumbnail images that are displayed in a case display region is magnified which differs from the basic screens shown in FIGS. 9 and 10.

FIG. 11 is a diagram showing the basic screen K2 when a part of thumbnail images that are displayed in the case display region 710 is magnified which differs from the basic screens K2 shown in FIGS. 9 and 10. In FIG. 11, the user has selected a thumbnail image that differs from that shown in FIG. 9. Accordingly, the thumbnail image to be magnified is changed. In other words, in FIG. 11, a thumbnail image of a similar case displayed in the 3rd-row, 3rd-column display region 1101 has been selected. As a result, the magnified image generating unit 112 magnifies a total of 11 thumbnail images from a thumbnail image (2nd-row, 3rd-column) adjacent to the above of the selected thumbnail image to a thumbnail image (4th-row, 3rd-column) adjacent to below of the selected thumbnail image in an order of lateral arrangement.

Figure 12:
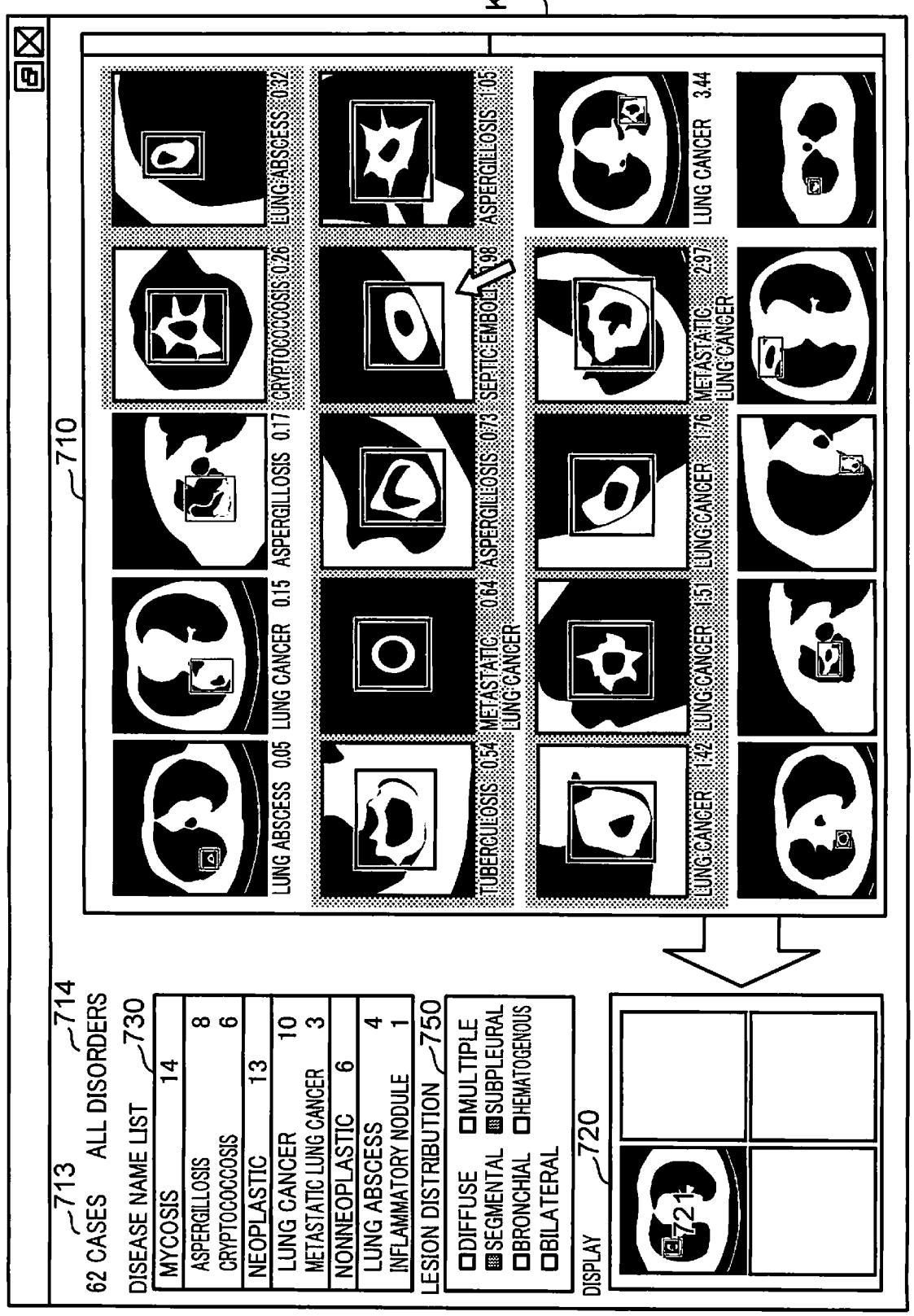
FIG. 12 is a diagram showing a different display mode when the same thumbnail image as shown in FIG. 9 is magnified.

FIG. 12 is a diagram showing a different display mode when the same thumbnail image (2nd-row, 4th-column) as shown in FIG. 9 is magnified. As shown in FIG. 12, the display control unit 104 has highlighted and displayed the thumbnail image to be magnified. In the example shown in FIG. 12, a color of a frame-like region that encloses an outer periphery of the magnified thumbnail image has been changed in a similar manner to the selected thumbnail image. Accordingly, the magnified thumbnail image can be emphasized to the user. As a result, even when magnified thumbnail images and thumbnail images that are not magnified coexist in the case display region 710 as shown in FIG. 12, the user can readily distinguish magnified thumbnail images from those that are not magnified.

As described above, by simply performing a magnification operation on one thumbnail image of a similar case having attracted the interest of a physician to perform image diagnosis, similar cases that are similar to the similar case of interest are also magnified and displayed in a connected manner. Therefore, the physician can perform a detailed comparison of a plurality of similar cases by one instruction. As a result, the number of operations can be reduced significantly.

Moreover, while a case where a part of the thumbnail images in the case display region 710 is magnified has been described, the present disclosure is not limited to such cases. For example, when any one of the thumbnail images is selected by the user, all of the 20 thumbnail images displayed in the case display region 710 may be magnified.

Figure 13:
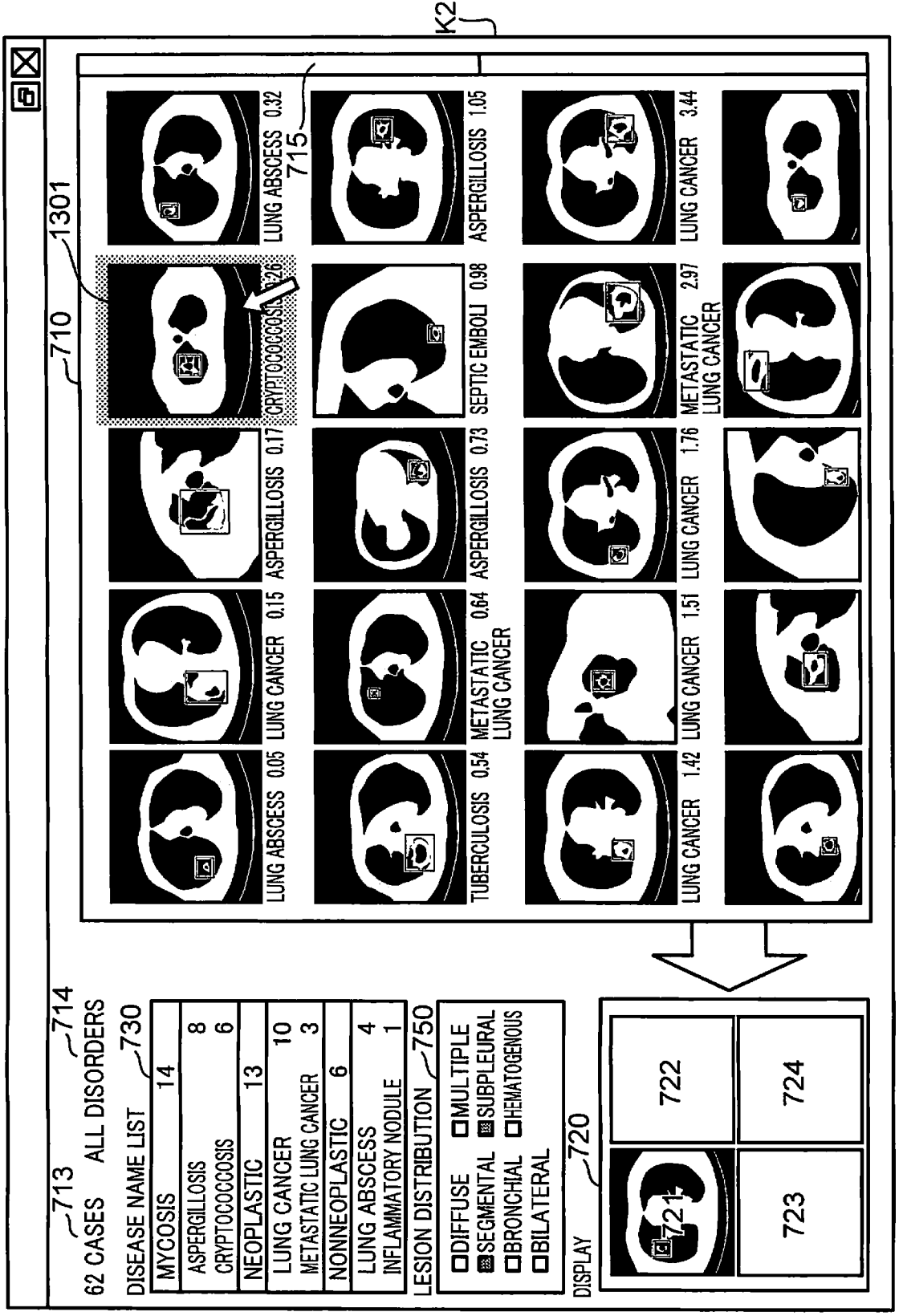
FIG. 13 is a diagram showing a basic screen when a different thumbnail image from that shown in FIG. 8 is selected among thumbnail images displayed in a case display region.

FIG. 13 is a diagram showing the basic screen K2 when a thumbnail image which differs from that shown in FIG. 8 is selected among the thumbnail images displayed in the case display region 710. In FIG. 13, a thumbnail image displayed in a 1st-row, 4th-column display region 1301 has been selected by the user.

As shown in FIG. 13, when the user performs a magnification operation by, for example, rotating the wheel of the mouse in a state where the 1st-row, 4th-column thumbnail image is selected, the input control unit 103 senses an amount of rotation of the wheel of the mouse and notifies the magnified image generating unit 112 of the sensed amount of rotation. As a result, for example, the magnified image generating unit 112 decides magnification ratios of the respective thumbnail images based on the notified amount of rotation and magnifies all of the thumbnail images at the decided magnification ratios. The display control unit 104 displays the thumbnail images magnified by the magnified image generating unit 112 in the case display region 710 as shown in FIG. 14 or 15, for example.

Figure 14:
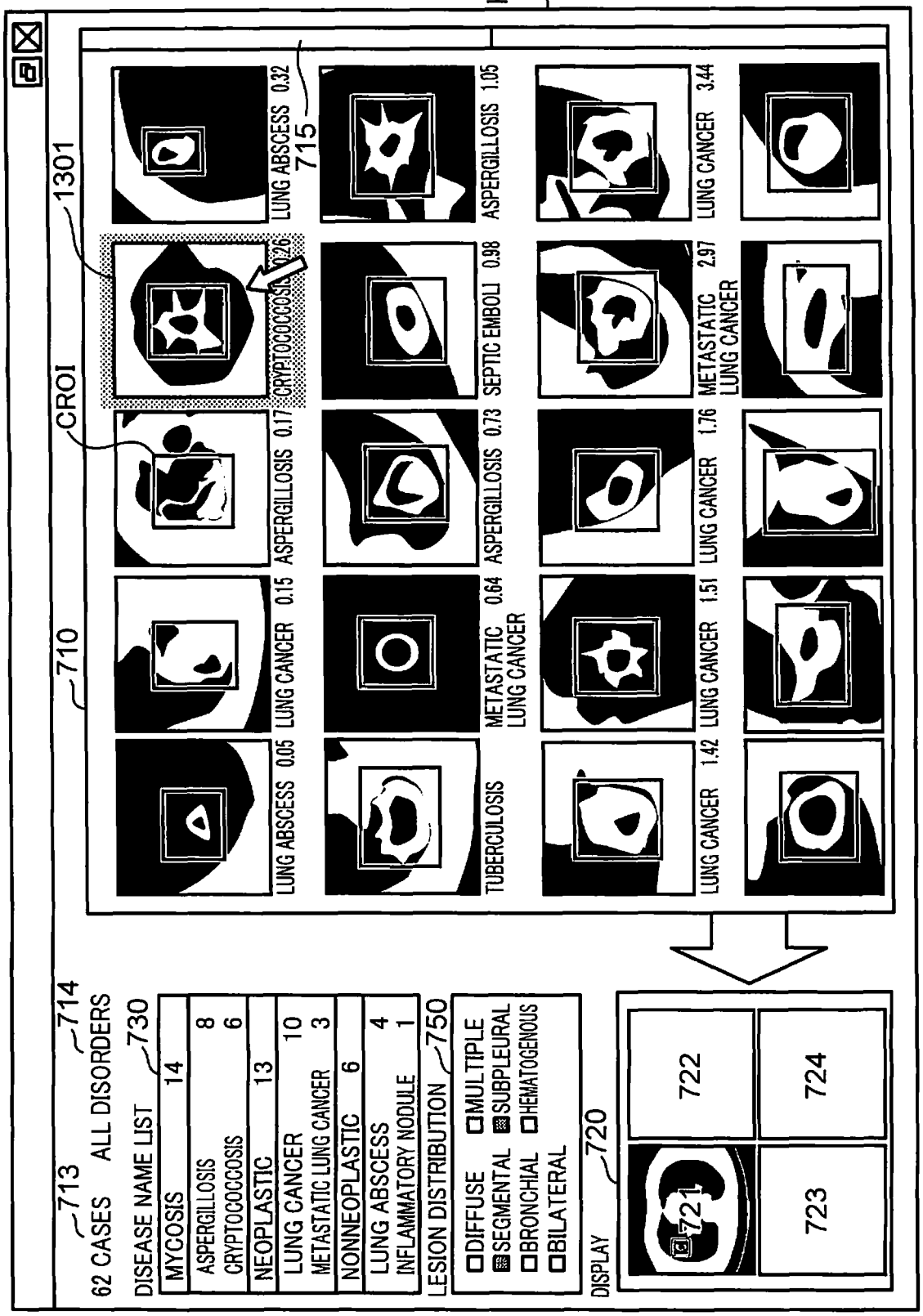
FIG. 14 is a diagram showing a basic screen when all thumbnail images that are displayed in a case display region are magnified.

FIG. 14 is a diagram showing the basic screen K2 when all thumbnail images that are displayed in the case display region 710 are magnified. Moreover, even in FIG. 14, the magnified image generating unit 112 respectively generates the magnified thumbnail images so that a center position of the corresponding region of interest CROI matches a center position of a display region in a similar manner to FIG. 9.

Figure 15:
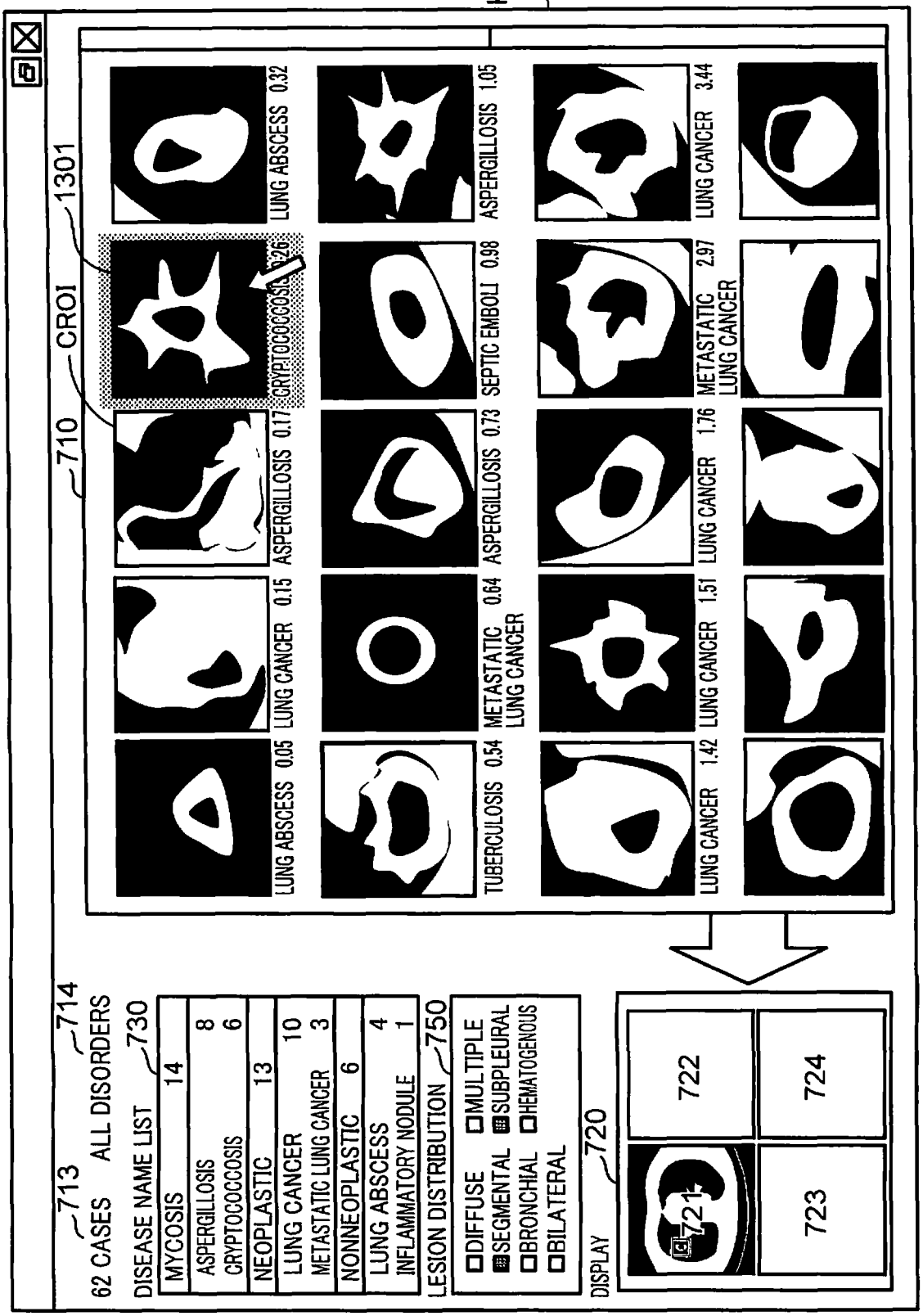
FIG. 15 is a diagram showing a basic screen when all thumbnail images that are displayed in a case display region are magnified which differs from the basic screen shown in FIG. 14.

FIG. 15 is a diagram showing the basic screen K2 when all thumbnail images that are displayed in the case display region 710 are magnified which differs from the basic screen K2 shown in FIG. 14. In FIG. 15, the magnified image generating unit 112 respectively generates the magnified thumbnail images so that a size of the corresponding region of interest CROI matches a size of a display region in a similar manner to FIG. 10.

According to the cases shown in FIG. 14 or FIG. 15, thumbnail images that are magnified and thumbnail images that are not magnified do not coexist in the case display region 710. Therefore, an advantage of improved visibility is gained.

Moreover, while a rotation of the wheel of the mouse is adopted as the magnification operation by the user in the description given above, the present disclosure is not limited thereto. For example, a magnification operation may be performed by arranging a mouse pointer on one thumbnail image displayed in the case display region 710 and by pressing, for example, an upward key or a downward key on a keyboard while keeping a button of the mouse depressed. In this case, the input control unit 103 may count the period of time during which the upward key or the downward key is depressed. The magnified image generating unit 112 may decide a magnification ratio based on, for example, the period of time during which the upward key or the downward key is depressed.

Moreover, details of specific procedures of a magnification process will be described later.

Returning to FIG. 6, the layout region 720 is arranged in a bottom left part of the basic screen K2 shown in FIG. 6, for example. In addition, the layout region 720 is used to display an image which the user wishes to observe in detail among the similar case thumbnail images displayed in the case display region 710 on a medical image viewer of the display 101a. As shown in FIG. 5, four medical image viewers 610 to 640 are arranged in two rows and two columns on the display 101a. In addition, four display boxes 721 to 724 exist in two rows and two columns in the layout region 720. In this manner, the number and arrangement of the medical image viewers 610 to 640 displayed on the display 101a and the number and arrangement of the display boxes 721 to 724 in the layout region 720 are matched with each other. As shown in FIG. 5, in conformance of a retrieval query image displayed in the medical image viewer 610, a thumbnail image of the retrieval query image is initially displayed in the display box 721.

The other display boxes 722 to 724 display thumbnail images of similar cases in conjunction with the medical image viewers 620 to 640. Specifically, when the input control unit 103 senses one of the thumbnail images displayed in the case display region 710 being dragged and dropped in any one of the display boxes 722 to 724, the display control unit 104 displays the one thumbnail image in the display box and, at the same time, displays a slice image corresponding to the thumbnail image on the medical image viewer corresponding to the display box. In this manner, the medical image viewers 610 to 640 correspond one-to-one with the display boxes 721 to 724.

In the example shown in FIG. 6, since the display boxes 722 to 724 are empty, the medical image viewers 620 to 640 shown in FIG. 5 are also blank.

By dragging and dropping using a mouse, the user moves a thumbnail image that the user wishes to observe in detail from the case display region 710 to the layout region 720. For example, assuming that the user has moved a thumbnail image to the display box 722, a slice image corresponding to the thumbnail image is displayed on the medical image viewer 620 corresponding to the display box 722. In a similar manner, assuming that the user has moved a thumbnail image to the display box 723, a slice image corresponding to the thumbnail image is displayed on the medical image viewer 630 corresponding to the display box 723. In other words, when a thumbnail image is moved to any display box among the display boxes 721 to 724, a thumbnail image of a similar case is displayed adjacent to a thumbnail image of a retrieval query image. Therefore, the user can compare a diagnosis object case with a similar case on a thumbnail image level and can promptly determine a degree of similarity between both cases. In other words, since an amount of information in a thumbnail image is smaller than that of a slice image, the user can make a rough estimate as to how similar the diagnosis object case and the similar case arranged adjacent to each other in the layout region 720 are to each other. Therefore, the user can efficiently narrow down a final candidate of a similar case which needs to be compared in detail at a slice image level with the diagnosis object case from the large number of similar cases displayed in the case display region 710.

In a similar manner, the display 101a also displays slice images of the retrieval query image and a similar case in the same arrangement relationship as in the layout region 720. Therefore, once an operation for narrowing down a final candidate of a similar case in the layout region 720 is finished, the diagnosis object case and a similar case that has been narrowed down as a final candidate are displayed on a slice image level in the display 101a without having to input any operation. As a result, the user can make a smooth transition to a next operation step that is to diagnostically interpret a diagnosis object and a similar case that is a final candidate in detail.

The disease name list display region 730 to which a heading reading "disease name list" is attached is arranged in an upper part of a left side of the basic screen K2 shown in FIG. 6. Definitively diagnosed disease names of all similar cases acquired as a similar case retrieval result are displayed in the disease name list display region 730. After a diagnosis is made and a definitively diagnosed disease name is assigned, a diagnosis object case is accumulated as a similar case in the case retrieval system 300. Therefore, a definitively diagnosed disease name assigned by a diagnosis is assigned in advance to each similar case.

FIG. 16 is an enlarged view of the disease name list display region 730. In FIG. 16, definitively diagnosed disease names are displayed divided into broadly categorized disease names (731, 734, 737, 741, and 744) and finely categorized disease names (732, 733, 735, 736, 738, 739, 740, 742, 743, and 745). In the example shown in FIG. 16, mycosis 731, neoplastic 734, nonneoplastic 737, mycobacteriosis 741, and other 744 are displayed as broadly categorized disease names.

In addition, in the example shown in FIG. 16, aspergillosis 732 and cryptococcosis 733 are displayed as finely categorized disease name of mycosis 731. Furthermore, lung cancer 735 and metastatic lung cancer 736 are displayed as finely categorized disease names of neoplastic 734. Moreover, lung abscess 738, sarcoidosis 739, and septic emboli 740 are displayed as finely categorized disease names of nonneoplastic 737. In addition, nontuberculous mycobacteria (NTM) 742 and tuberculosis 743 are displayed as finely categorized disease names of mycobacteriosis 741. Furthermore, bronchiectasis 745 is displayed as a finely categorized disease name of other 744.

Figure 17:
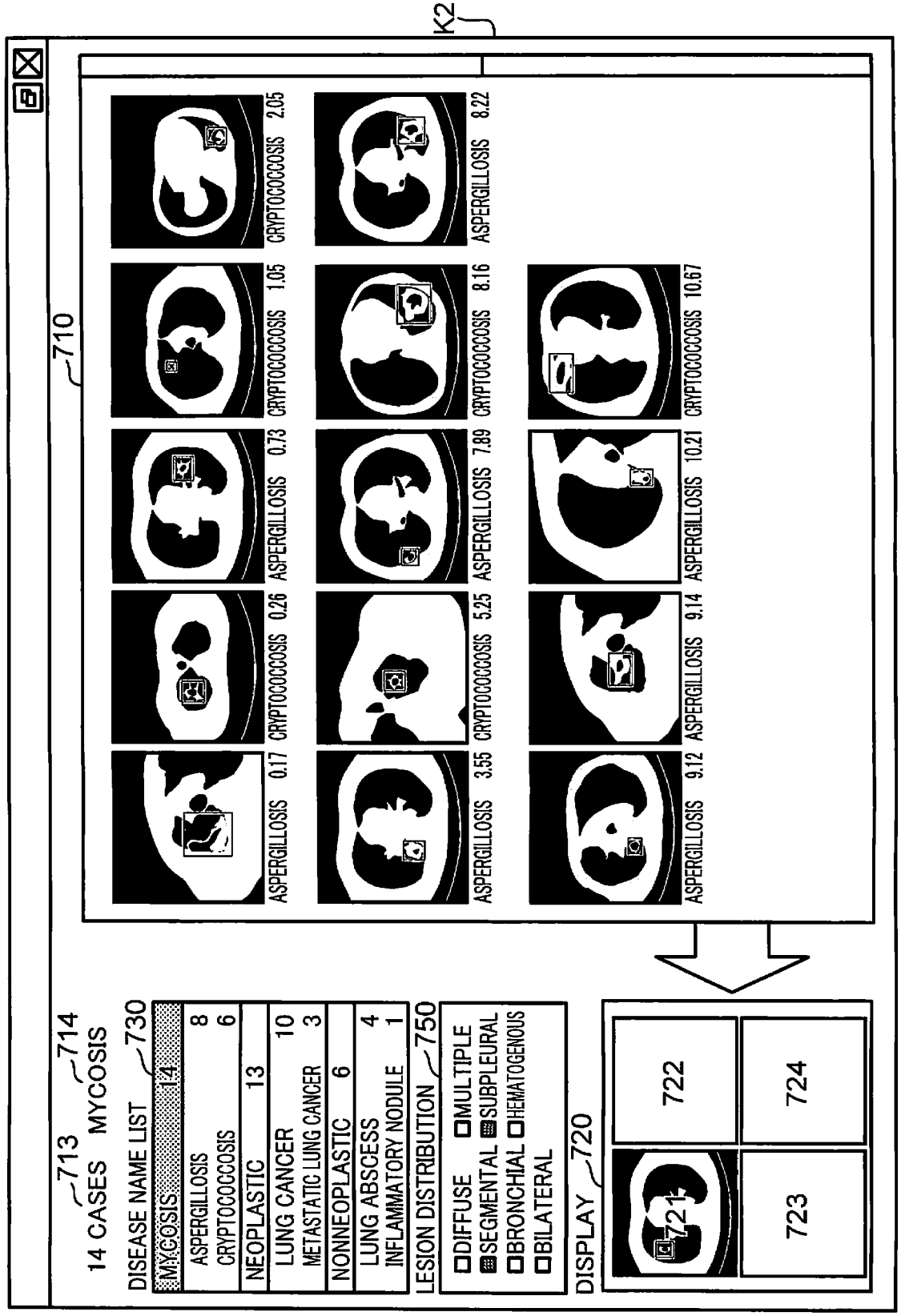
FIG. 17 is a diagram showing a basic screen when similar cases are narrowed down by "mycosis".
Figure 18:
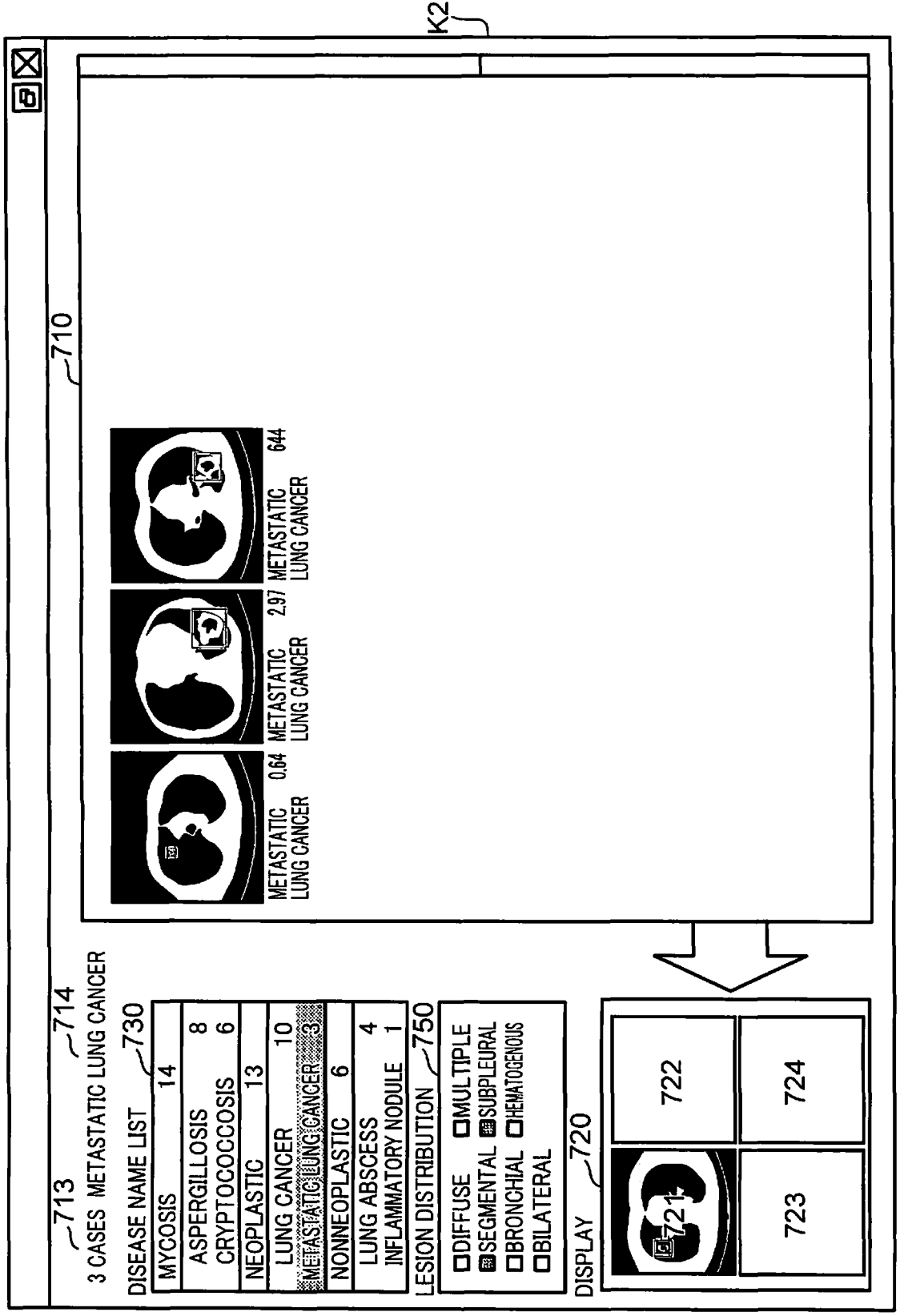
FIG. 18 is a diagram showing a basic screen when similar cases are narrowed down by "metastatic lung cancer".

In addition, the number of cases corresponding to a disease name is displayed besides broadly categorized disease names and finely categorized disease names. By selecting an arbitrary row of a broadly categorized disease name or a finely categorized disease name in the disease name list display region 730, the use can narrow down a similar case to be displayed in the case display region 710. While 62 similar cases including various disorders are set as display objects in a state immediately following similar case retrieval as shown in FIG. 6, when the row of mycosis 731 in FIG. 16 is clicked using a mouse, the display control unit 104 only displays similar cases of mycosis in the case display region 710 as shown in FIG. 17. Furthermore, when the row of metastatic lung cancer 736 in FIG. 16 is clicked using a mouse, the display control unit 104 only displays similar cases of metastatic lung cancer in the case display region 710 as shown in FIG. 18.

At this point, the display control unit 104 displays narrowed-down disease names in the display condition display region 714 so as to show what kind of narrowing condition applies to the similar cases currently displayed in the case display region 710. FIG. 17 is a diagram showing the basic screen K2 when similar cases are narrowed down by "mycosis". FIG. 18 is a diagram showing the basic screen K2 when similar cases are narrowed down by "metastatic lung cancer".

In the example shown in FIG. 17, since similar cases are narrowed down by "mycosis", "mycosis" is displayed in the display condition display region 714. In the example shown in FIG. 18, since similar cases are narrowed down by "metastatic lung cancer", "metastatic lung cancer" is displayed in the display condition display region 714.

In addition, at this point, the display control unit 104 shows the number of similar cases currently displayed in the case display region 710 by displaying the number in the number of retrieved results display region 713. In the example shown in FIG. 17, since there are 14 similar cases corresponding to "mycosis", "14" is displayed in the number of retrieved results display region 713. In the example shown in FIG. 18, since there are 3 similar cases corresponding to "metastatic lung cancer", "3" is displayed in the number of retrieved results display region 713.

Due to this function, only similar cases with disease names that are assumed to be objects of image diagnosis by a physician are displayed in the case display region 710 and the physician can readily check whether or not the diagnosis object case is consistent with the assumed disease names.

In FIG. 17, thumbnail images of M number (in FIG. 17, M=14) of similar cases are displayed in the case display region 710 that is capable of displaying a maximum number ND (in the present embodiment, ND=20) of cases.

The distribution list display region 750 to which a heading reading "lesion distribution" is attached is arranged in a middle part of the left side of the basic screen K2 shown in FIG. 6. Types of lesion distributions of all similar cases acquired from the case retrieval system 300 as a result of similar case retrieval are displayed in the distribution list display region 750.

FIG. 19 is an enlarged view of the distribution list display region 750. In the example shown in FIG. 19, names of seven lesion distributions are displayed and a check mark is arranged to the left of the name of each lesion distribution. In the example shown in FIG. 19, diffuse 751, segmental 752, bronchial 753, bilateral 754, multiple 755, subpleural 756, and hematogenous 757 are displayed as lesion distributions.

These lesion distributions are defined in advance and a distribution flag value (applicable: 1, not applicable: 0) indicating whether or not a similar case corresponds to any of diffuse 751 to hematogenous 757 is assigned to each similar case. Similar cases include those in which all distribution flag values are set to not applicable (:0) and those in which a plurality of all distribution flag values are set to applicable (:1).

The case retrieval system 300 according to the present embodiment retrieves a similar case having a region of interest that is similar to a region of interest set by the user in a slice image of a diagnosis object case. There may exist lesions other than the slice image to which a region of interest is set by the user. In addition, there may be cases where, after retrieving a similar case based on the slice image to which a region of interest is set, the user wishes to compare a slice image other than the slice image with the retrieved similar case. In such a case, the user inputs a slice feeding operation on the medical image viewer 610 to cause the medical image viewer 610 to display another slice image and performs an operation for comparing the slice image with the retrieved similar case. In this case, if only similar cases related to a lesion of interest among all retrieved similar cases are displayed in the case display region 710, an operation of extracting a slice image having a desired lesion from slice images other than the slice image to which a region of interest is set can be performed smoothly. In consideration thereof, in the present embodiment, a function for narrowing down retrieved similar cases by a desired lesion distribution is provided to enable this operation to be performed in a smooth manner.

In the present embodiment, as lesion distributions in a lung field region, the lesion distributions represented by diffuse 751 to hematogenous 757 shown in FIG. 19 are adopted. In addition, as shown in FIG. 19, with respect to check boxes and disease name distributions, the display control unit 104 displays lesion distributions that can be narrowed down in an active state and displays lesion distributions that cannot be narrowed down in an inactive state. In this case, a state in which brightness is higher than the inactive state is adopted as the active state and a state in which brightness is lower than the active state is adopted as the inactive state.

In the example shown in FIG. 19, diffuse 751, and bronchial 753 to hematogenous 757 are displayed in the active state and segmental 752 is displayed in the inactive state. This is because, among all similar cases acquired by a similar case retrieval, the distribution flag values of diffuse 751, and bronchial 753 to hematogenous 757 are currently set to 1 (applicable) in at least one of the similar cases while the distribution flag values of segmental 752 is currently set to 0 (not applicable) in all of the acquired similar cases.

When the input control unit 103 senses that a check mark has been input to one or more check boxes among the check boxes in the active state, the display control unit 104 displays only similar cases corresponding to lesion conditions for which a check mark had been input in the case display region 710.

Moreover, for segmental 752, the distribution flag value is set to 0 (not applicable) in all of the similar cases acquired as a retrieval result. Therefore, when a configuration that enables a check mark to be input for segmental 752 is adopted and a check mark is input for these lesion distributions, no similar case is to be displayed in the case display region 710. As a result, inputting a check mark becomes meaningless. In consideration thereof, in the present embodiment, in order to avoid such circumstances, a lesion distribution for which the distribution flag value is set to 0 (not applicable) in all of the similar cases acquired as a retrieval result is displayed in the inactive state.

Figure 21:
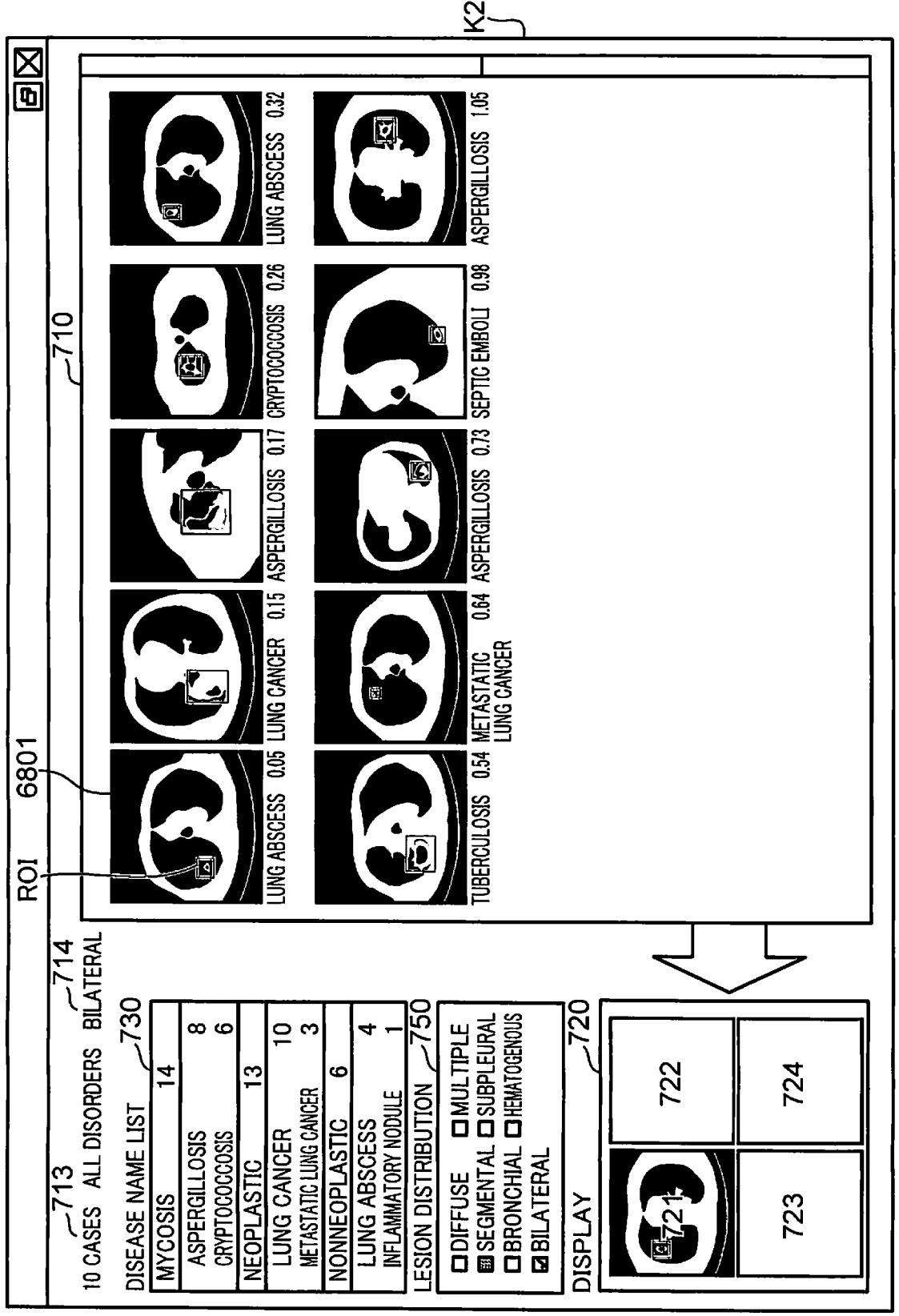
FIG. 21 is a diagram showing a basic screen having been narrowed down by a lesion distribution of bilateral.

FIG. 20 is a diagram showing the distribution list display region 750 in which a check mark is input to a check box corresponding to bilateral 754. FIG. 21 is a diagram showing the basic screen K2 having been narrowed down by a lesion distribution of bilateral 754. When a check mark is input to the check box of bilateral 754 as shown in FIG. 20, the display control unit 104 displays only similar cases with a bilateral lesion distribution in the case display region 710 as shown in FIG. 21. In this example, there are 10 similar cases with a bilateral lesion distribution. Therefore, the display control unit 104 displays "10" in the number of retrieved results display region 713. In addition, the display control unit 104 displays a disease name of a display object and "bilateral" that is the name of the lesion distribution in the display condition display region 714. In the example shown in FIG. 21, since similar cases have not been narrowed down by a disease name listed in the disease name list display region 730, the display condition display region 714 displays "all disorders".

When a check mark is input to the check box of bilateral 754 as shown in FIG. 20, the display control unit 104 displays thumbnail images magnified by the magnified image generating unit 112 at a magnification ratio corresponding to the selected lesion distribution in the case display region 710 as shown in FIG. 21. When the lesion distribution name "bilateral" is selected, both sides of the lung must be made observable. Therefore, the magnified image generating unit 112 sets the magnification ratio to 1.0. The display control unit 104 displays thumbnail images at a magnification ratio of 1.0.

In a similar manner, when a check mark is input to the check box of multiple 755, the display control unit 104 displays only similar cases with a multiple lesion distribution in the case display region 710. When the lesion distribution name "multiple" is selected, a distribution of lesions occurring in numbers must be made observable. Therefore, the magnified image generating unit 112 sets the magnification ratio to 1.0. The display control unit 104 displays thumbnail images at a magnification ratio of 1.0.

In a similar manner, when a check mark is input to the check box of diffuse 751, the display control unit 104 displays only similar cases with a diffuse lesion distribution in the case display region 710. When the lesion distribution name "diffuse" is selected, a distribution of a diffuse lesion which spreads over a wide range must be made observable. Therefore, the magnified image generating unit 112 sets the magnification ratio to 1.0. The display control unit 104 displays thumbnail images at a magnification ratio of 1.0.

In a similar manner, when a check mark is input to the check box of hematogenous 757, the display control unit 104 displays only similar cases with a hematogenous lesion distribution in the case display region 710. In the case of hematogenous, there is a possibility that the lesion may have spread to parts other than the lesion of interest. Therefore, an entire image must be confirmed. As a result, the magnified image generating unit 112 sets the magnification ratio to 1.0. The display control unit 104 displays thumbnail images at a magnification ratio of 1.0.

Figure 23:
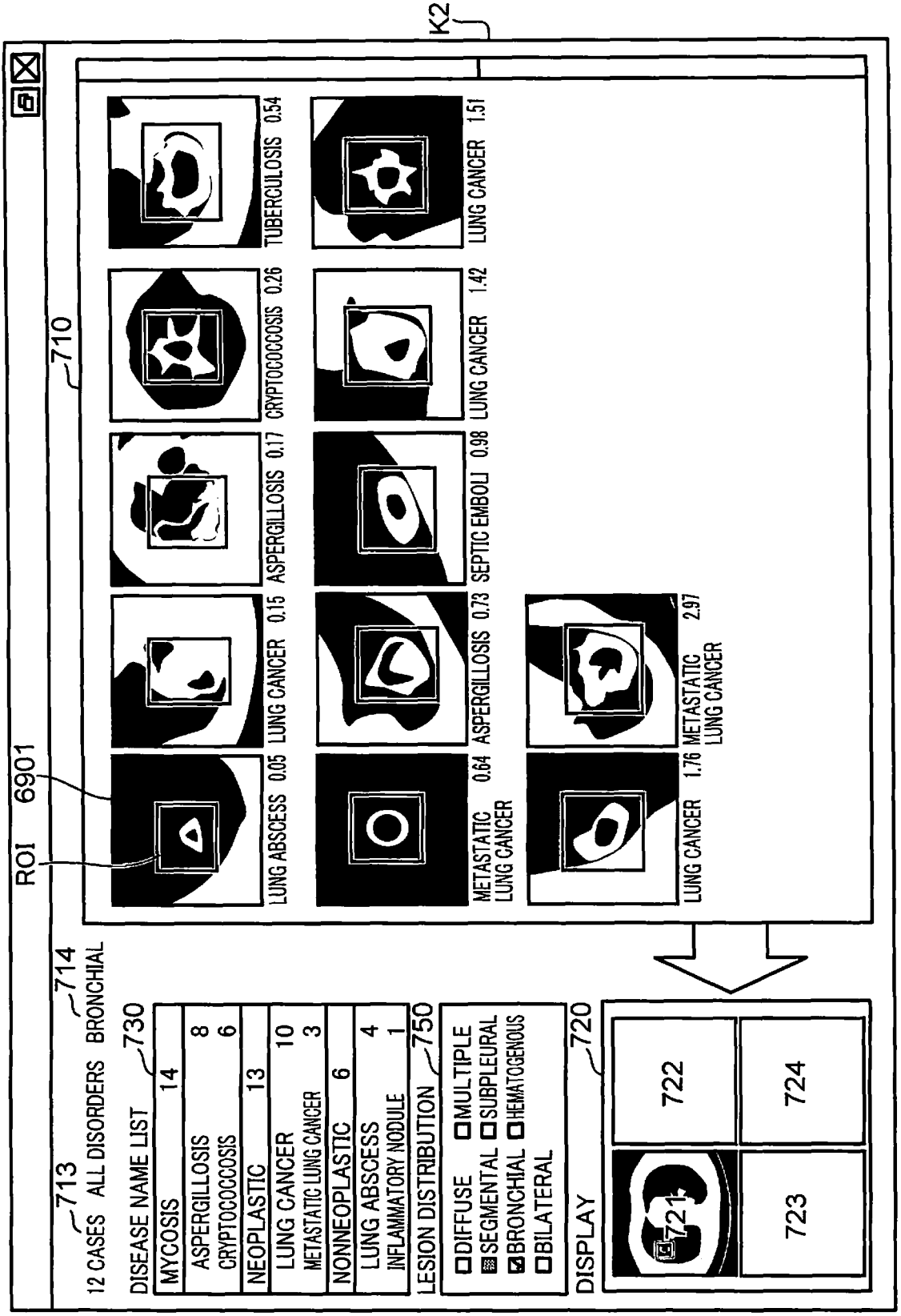
FIG. 23 is a diagram showing a basic screen having been narrowed down by a bronchial lesion distribution.

FIG. 22 is a diagram showing the distribution list display region 750 in which a check mark is input to the check box of bronchial 753. FIG. 23 is a diagram showing the basic screen K2 having been narrowed down by a bronchial lesion distribution. When a check mark is input to the check box of bronchial 753 as shown in FIG. 22, the display control unit 104 displays only similar cases with a bronchial lesion distribution in the case display region 710 as shown in FIG. 23. In this example, there are 12 similar cases with a bronchial lesion distribution. Therefore, the display control unit 104 displays "12" in the number of retrieved results display region 713. In addition, the display control unit 104 displays a disease name that is a display object and "bronchial" that is the name of the lesion distribution in the display condition display region 714. In the example shown in FIG. 23, since similar cases have not been narrowed down by a disease name listed in the disease name list display region 730, the display condition display region 714 displays "all disorders".

When a check mark is input to the check box of bronchial 753 as shown in FIG. 22, the display control unit 104 displays thumbnail images magnified by the magnified image generating unit 112 at a magnification ratio corresponding to the selected lesion distribution in the case display region 710 as shown in FIG. 23. When the lesion distribution name "bronchial" is selected, whether or not a lesion is bronchial must be determinable. Therefore, the magnified image generating unit 112 decides a magnification ratio that causes an area of a region of interest to be around ½ of the display region. The display control unit 104 displays each of the thumbnail images magnified by the magnified image generating unit 112.

In a similar manner, when a check mark is input to the check box of segmental 752, the display control unit 104 displays only similar cases with a segmental lesion distribution in the case display region 710. When the lesion distribution name "segmental" is selected, details of a segmental lesion must be confirmable. Therefore, the magnified image generating unit 112 decides a magnification ratio that causes an area of a region of interest to be around ½ of the display region. The display control unit 104 displays each of the thumbnail images magnified by the magnified image generating unit 112.

Figure 25:
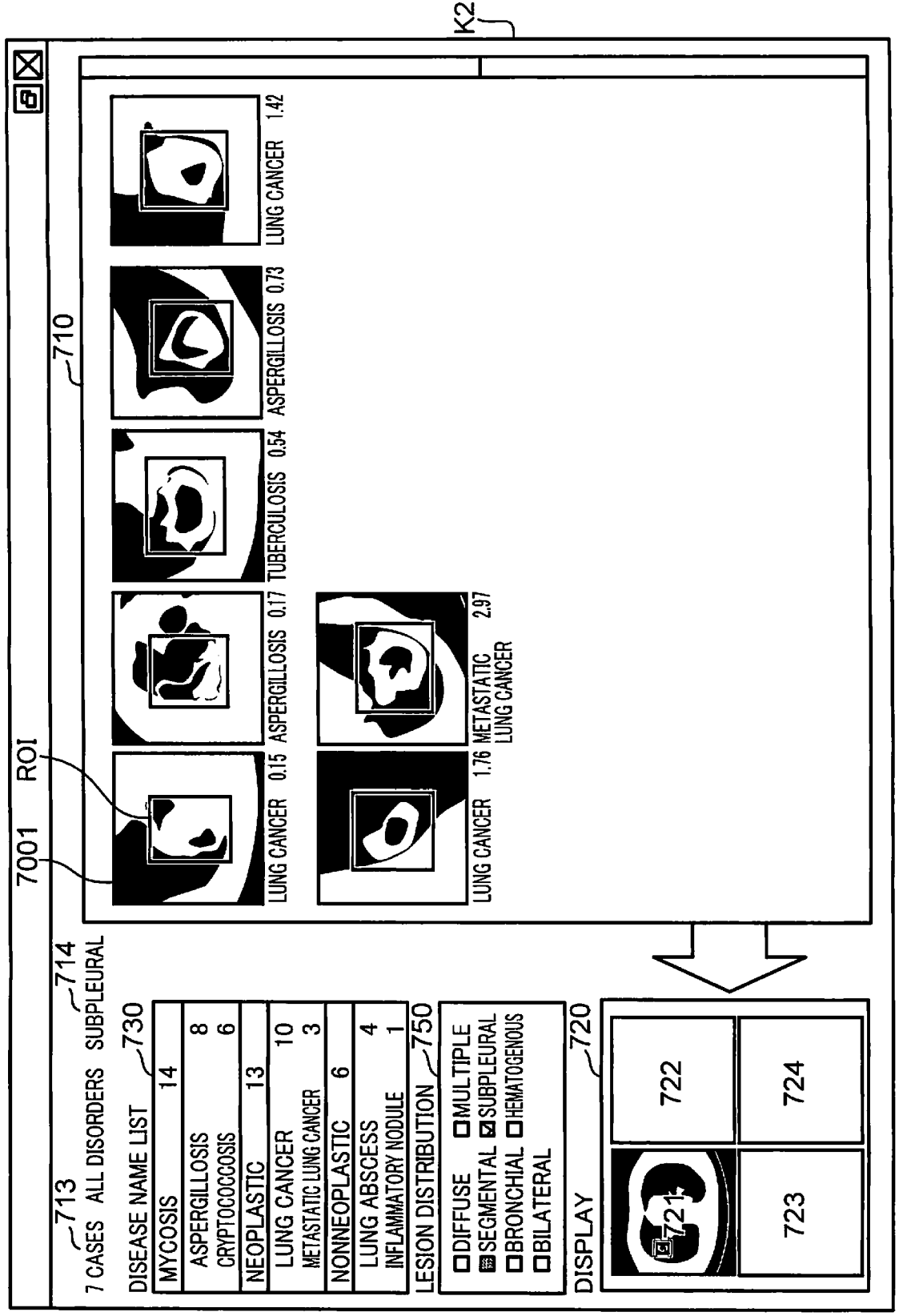
FIG. 25 is a diagram showing a basic screen having been narrowed down by a lesion distribution of subpleural.

FIG. 24 is a diagram showing the distribution list display region 750 in which a check mark is input to a check box corresponding to subpleural 756. FIG. 25 is a diagram showing the basic screen K2 having been narrowed down by a lesion distribution of subpleural 756. When a check mark is input to the check box of subpleural 756 as shown in FIG. 24, the display control unit 104 displays only similar cases with a subpleural lesion distribution in the case display region 710 as shown in FIG. 25. In this example, there are 7 similar cases with a subpleural lesion distribution. Therefore, the display control unit 104 displays "7" in the number of retrieved results display region 713. In addition, the display control unit 104 displays a disease name of a display object and "subpleural" that is the name of the lesion distribution in the display condition display region 714. In the example shown in FIG. 25, since similar cases have not been narrowed down by a disease name listed in the disease name list display region 730, the display condition display region 714 displays "all disorders".

When a check mark is input to the check box of subpleural 756 as shown in FIG. 24, the display control unit 104 displays thumbnail images magnified by the magnified image generating unit 112 at a magnification ratio corresponding to the selected lesion distribution in the case display region 710 as shown in FIG. 25. When the lesion distribution name "subpleural" is selected, a positional relationship with the pleura must be made observable. Therefore, the magnified image generating unit 112 decides a magnification ratio that causes the pleura to be included. The display control unit 104 displays each of the thumbnail images magnified by the magnified image generating unit 112.

Moreover, details of a magnification process with respect to the respective thumbnail images when selecting a lesion distribution in FIGS. 21, 23, and 25 will be described later.

FIG. 26 is a diagram showing a data configuration of the patient information 1000. The patient information 1000 is accumulated and managed in the patient information accumulating unit 201 for each patient by the patient information managing unit 202 of the medical information management system 200. Personal information of a patient such as gender and age, clinical information of the patient such as medical history, and examination information of the patient such as a blood test are registered in the patient information 1000. As shown in FIG. 26, the patient information 1000 includes a patient ID 1100, a name 1200, an age 1300, a gender 1400, a medical history 1500, a family medical history 1600, a chief complaint 1700, examination information 1800, and a definitive diagnosis 1900.

The patient ID 1100 is an identifier unique to a patient. The name 1200, the age 1300, the gender 1400, the medical history 1500, the family medical history 1600, and the chief complaint 1700 are, respectively, the name, the age, the gender, the medical history, the family medical history, and the chief complaint of the patient represented by the patient ID 1100. As shown in FIG. 27, the examination information 1800 represents information related to one or more examinations previously undergone by the patient.

FIG. 27 is a diagram showing a data configuration of examination information 1800 shown in FIG. 26. The examination information 1800 is information related to an examination performed on a patient and is created one piece at a time in correspondence to each examination. The examination information 1800 includes an examination ID 1810, an examination date/time 1820, an examination type 1830, and an examination result 1840. The examination ID 1810 is an identifier unique to an examination. The examination date/time 1820 represents a date and time when the examination had been performed. The examination type 1830 represents a type of the examination. Examples of examination types include a blood test, a respiratory function test, an endoscopic examination, plain radiography, and a CT scan.

In a case of a blood test, various indicators including a white blood cell count, LDH, and GPT correspond to the examination result 1840. In addition, for example, a judgment made by a physician based on various indicators also corresponds to the examination result 1840. Furthermore, in a case of an image-based examination such as plain radiography and a CT scan, the examination result 1840 includes pointer information to a photographed image or pointer information to a report containing an image diagnosis result. Moreover, images photographed in the course of an examination are accumulated in the DICOM format in the medical image data accumulating unit 203 of the medical information management system 200.

In addition, when the examination type 1830 is an image-based examination such as plain radiography, a CT, an MRI, and a PET, medical image data thereof are accumulated in a medical image database 2000 stored by the medical image data accumulating unit 203 of the medical information management system 200.

Figure 28:
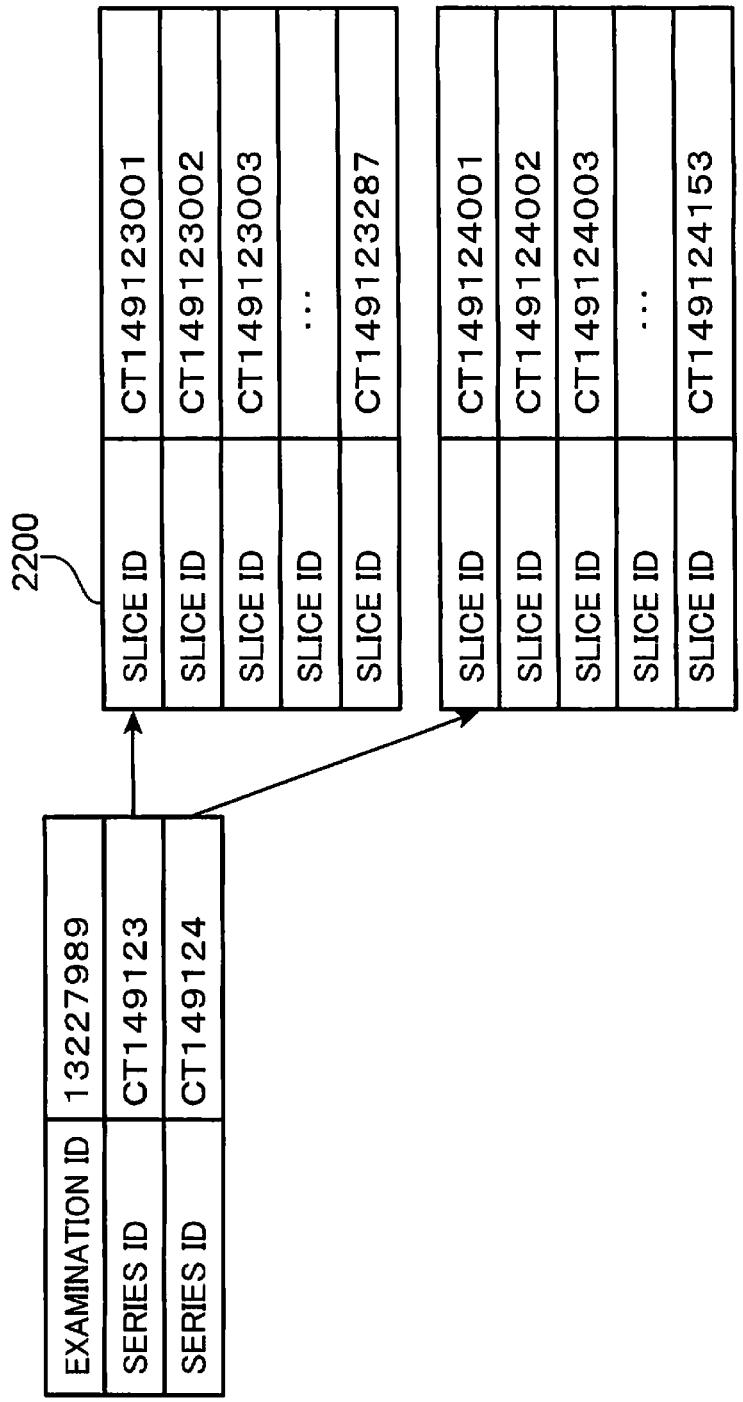
FIG. 28 is a diagram showing a data configuration of a medical image database.

FIG. 28 is a diagram showing a data configuration of the medical image database 2000. The medical image database 2000 includes the examination ID 1810 and a series ID 2100. Since there are cases where a plurality of types of photography (for example, a plain CT and a contrast-enhanced CT) are performed in one examination, there may be cases where a plurality of series IDs 2100 are associated with one examination ID 1810. In other words, the number of acquired series corresponds to the number of types of photography.

In addition, besides each type of photography, a series is obtained for each reconstruction condition of a photographed image. For example, when a photographed image is reconstructed in a lung window setting and a mediastinal window setting, one series is obtained for each of the settings. Moreover, in an image reconstructed in a lung window setting, blood vessels, bronchi, alveoli, and the like of the lungs are displayed highlighted. In addition, in an image reconstructed in a mediastinal window setting, a mediastinum including blood vessels and lymph nodes are displayed highlighted. Since a lung window setting and a mediastinal window setting are obtained by reconstructing an image obtained in one photographic session, when two photographic sessions are performed with plain CT and contrast-enhanced CT and images are reconstructed in a lung window setting and a mediastinal window setting for each of the two photographic sessions, two series in the lung window setting are obtained and two series in the mediastinal window setting are obtained.

In an image-based examination by a CT and an MRI, since a plurality of slice images are acquired by one photographic session, a plurality of slice IDs 2200 are associated with one series ID 2100. Since two series IDs "CT149123" and "CT149124" are associated with the examination ID "13227989" in FIG. 28, it is shown that two CT image series have been obtained from the examination. It is also shown that a plurality of slice IDs 2200 are associated with each of the series IDs "CT149123" and "CT149124".

When the examination type 1830 is an image-based examination such as plain radiography, a CT, an MRI, and a PET, a diagnostic report 3000 such as that shown in FIG. 29 is accumulated in the diagnostic report managing unit 205 of the medical information management system 200. A diagnostic result by a physician with respect to each examination is registered in the diagnostic report 3000.

FIG. 29 is a diagram showing a data configuration of the diagnostic report 3000. The diagnostic report 3000 includes the examination ID 1810, findings 3100, and a diagnosis 3200. The examination ID 1810 is the same as the examination ID 1810 shown in FIG. 27. Accordingly, the diagnostic report 3000 and the examination information 1800 are associated with each other. A text representing findings of the physician with respect to the examination is registered in the findings 3100. A text representing a diagnosis of the physician with respect to the examination is registered in the diagnosis 3200.

FIG. 30 is a diagram showing a data configuration of similar case data 4000. The similar case data 4000 is data that is referred to when retrieving a similar case that is similar to a diagnosis object case. One piece of similar case data 4000 is created corresponding to one similar case. Moreover, the similar case data 4000 is an example of the additional information of the similar medical image. The similar case data 4000 is accumulated for each similar case in the similar case data accumulating unit 301 of the case retrieval system 300. As shown in FIG. 30, the similar case data 4000 includes a similar case ID 4100, a slice ID 4200, region of interest information 4300, image feature data 4400, thumbnail image data 4500, lesion distribution information 4600, a definitive diagnosis (broadly categorized disease name) 4700, and a definitive diagnosis (finely categorized disease name) 4800.

The similar case ID 4100 is an identifier of the similar case data 4000. In this case, since one piece of similar case data is generated for each region of interest set in a slice image of a similar case, the similar case ID 4100 can also be considered an identifier of a region of interest. In the example shown in FIG. 30, the similar case ID 4100 is constituted by a symbol string constituted by "SIM" followed by a numeral.

Figure 31:
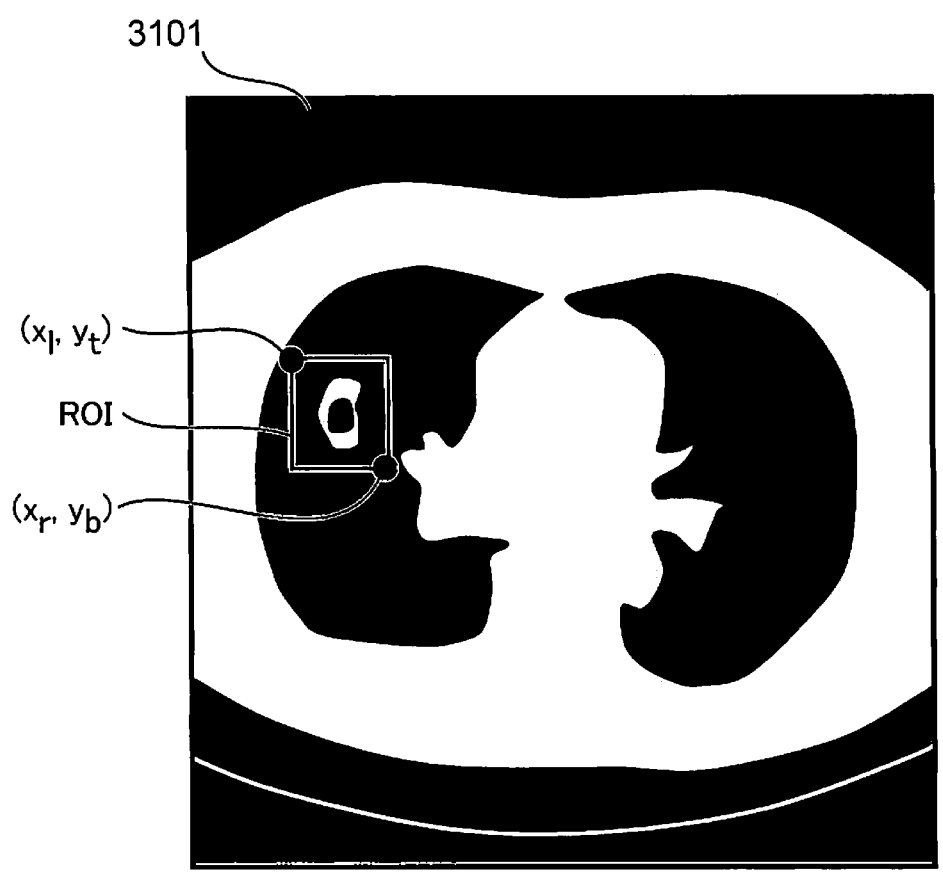
FIG. 31 is a diagram schematically showing a region of interest set in a slice image.

The slice ID 4200 is an identifier of a slice image in which a region of interest is set and is the same as the slice ID 2200 shown in FIG. 28. The region of interest information 4300 is information indicating a position of a region of interest set in the slice image. FIG. 31 is a diagram schematically showing a region of interest set in a slice image. In the example shown in FIG. 31, the region of interest is set in a rectangular shape. Therefore, the region of interest information 4300 is constituted by four values including coordinates (xl, yt) of a top left vertex and coordinates (xr, yb) of a bottom right vertex of the region of interest. Obviously, a region of interest may have a shape other than a rectangle. In such a case, a parameter capable of uniquely specifying the region is adopted as the region of interest information 4300. For example, when the region of interest has a circular shape, center coordinates and a radius of a circle are adopted as the region of interest information 4300.

The image feature data 4400 is a feature value of a prescribed number of dimensions (in this case, N-number of dimensions) that is extracted from the region of interest as defined by the region of interest information 4300. The thumbnail image data 4500 is image data of a thumbnail image generated to be displayed in the case display region 710 based on a slice image in the DICOM format as identified by a slice ID. In this case, in the thumbnail image data 4500, pixel values of a thumbnail image are arranged in a raster scanning sequence from a top left vertex to a bottom right vertex of the thumbnail image, for example. As described earlier, a DICOM image obtained by a CT examination is a 11 bit (pixel value: −1000 to +1000) image with 512×512 pixels. In consideration thereof, in the present embodiment, in order to facilitate display of a thumbnail image, a thumbnail image with a 8 bit pixel value is created in advance by subjecting a DICOM image that is a source of the thumbnail image to a low resolution process and a gradation conversion process and is registered in the similar case data 4000. Alternatively, for example, a thumbnail image may be created by the medical information management system 200 and transmitted to the case retrieval system 300 or the case retrieval system 300 may acquire a DICOM image from the medical information management system 200 to create a thumbnail image.

The lesion distribution information 4600 is a distribution flag value (1: applicable, 0: not applicable) indicating whether or not a similar case that is an object corresponds to any of lesion distributions represented by diffuse 4610 to hematogenous 4670 determined in advance.

The definitive diagnosis (broadly categorized disease name) 4700 represents a broadly categorized disease name that is confirmed with respect to a similar case that is an object. The definitive diagnosis (broadly categorized disease name) 4700 is used when narrowing down similar cases by a broadly categorized disease name.

The definitive diagnosis (finely categorized disease name) 4800 represents a finely categorized disease name that is confirmed with respect to a similar case that is an object. The definitive diagnosis (finely categorized disease name) 4800 is used when narrowing down similar cases by a finely categorized disease name.

As for the definitive diagnosis (broadly categorized disease name) 4700, a broadly categorized disease name which uniquely corresponds to the definitive diagnosis (finely categorized disease name) 4800 is defined in advance and stored in the similar case data 4000 using the correspondence relationship.

As for the definitive diagnosis (finely categorized disease name) 4800, the series ID 2100 is identified from the slice IDs 2200 shown in FIG. 28 in the medical image data accumulating unit 203. Subsequently, the examination ID 1810 is identified by the patient information accumulating unit 201 from the identified series ID, corresponding patient information 1000 (FIG. 26) is identified from the examination ID 1810, and a definitive diagnosis 1900 of a corresponding patient is identified from the identified patient information 1000.

Next, a flow from the start of a diagnostic interpretation operation to the start of a similar case retrieval by the information terminal 100 in cooperation with the medical information management system 200 and the case retrieval system 300 will be described.

Figure 32:
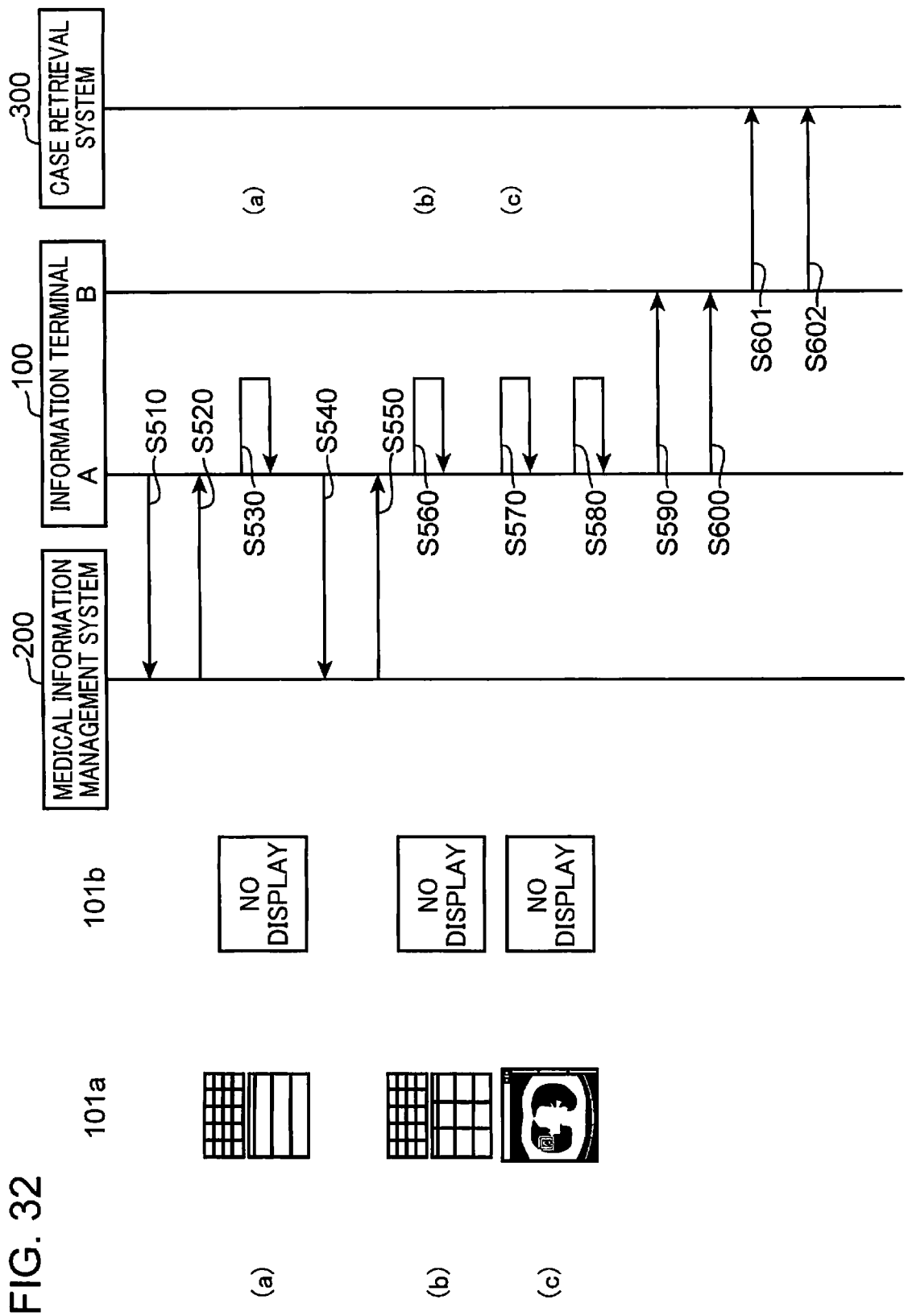
FIG. 32 is a sequence diagram showing a process in which an information terminal first acquires a diagnosis object case from a medical information management system and then issues a request for similar case retrieval to a case retrieval system, and the case retrieval system subsequently receives the request for similar case retrieval.

FIG. 32 is a sequence diagram showing a process in which the information terminal 100 first acquires a diagnosis object case from the medical information management system 200 and then issues a request for similar case retrieval to the case retrieval system 300, and the case retrieval system 300 subsequently receives the request for similar case retrieval. Moreover, in FIG. 32, two columns of rectangles shown to the left of the sequence diagram represent screens displayed on the displays 101*a* and 101*b* due to the processes of corresponding steps. In addition, in FIG. 32, "A" shown near the information terminal represents a medical information management application and "B" represents a similar case retrieval application. It is assumed that the medical information management application has been started prior to the start of the present sequence.

First, the information terminal 100 accepts a display request for an examination list to be a diagnostic interpretation object of a user (a physician to perform the diagnostic interpretation) through the operating unit 102, and transmits the display request for the examination list to the communication control unit 206 of the medical information management system 200 through the input control unit 103 and the communication control unit 110 (S510).

The patient information managing unit 202 of the medical information management system 200 lists examinations for which image-based examination has been performed but diagnostic interpretation has not been completed and generates a diagnostic interpretation object examination list. In addition, the patient information managing unit 202 transmits the generated examination list to the communication control unit 110 of the information terminal 100 through the communication control unit 206 (S520). In this case, the examination list includes patient information 1000 and examination information 1800 of a corresponding patient.

The display control unit 104 of the information terminal 100 displays the examination list received by the communication control unit 110 on the display 101 (S530).

In this case, the display 101*a* displays the examination list and the display 101*b* displays nothing.

FIG. 33 is a screen diagram of an examination list. The examination list includes a region 800 for displaying examinations for which diagnostic interpretation has not been completed and a region 810 for displaying information related to a series included in the examinations. Fields of a "patient ID", a "patient name", an "examination date/time", an "examination ID", and an "examination type" are provided in the region 800. The patient ID 1100 and the name 1200 registered in the patient information 1000 are displayed in the "patient ID" and "patient name" fields, and the examination date/time 1820, the examination ID 1810, and the examination type 1830, which are registered in the examination information 1800, are displayed in the "examination date/time", "examination ID", and "examination type" fields. The region 810 is a region for displaying details of an examination selected by the user in the region 800 and is provided with fields of a "series ID", a "definition", and an "image". In this case, since an examination (corresponding to rows) have not been selected by the user in the region 800, nothing is displayed in the region 810.

The user selects an examination for which diagnostic interpretation is to be performed from the examinations displayed in the region 800. When the selection is sensed by the input control unit 103, as shown in FIG. 32, the communication control unit 110 transmits a display request for all series included in the examination ID of the selected examination to the medical information management system 200 (S540).

When the communication control unit 206 of the medical information management system 200 receives the display request, the patient information managing unit 202 refers to the medical image database 2000 shown in FIG. 28, acquires all slice images of all series included in the examination ID specified by the display request, and transmits the slice images to the information terminal 100 through the communication control unit 206 (S550). For example, in the example shown in FIG. 28, when the examination with the examination ID "13227989" is selected by the user, all slice images included in the series with the series IDs "CT149123" and "CT149124" are transmitted in S550.

When the communication control unit 110 of the information terminal 100 acquires images of all series, the display control unit 104 displays a series list that displays information related to all series included in the specified examination ID as a list in the region 810 (S560).

In this case, a series list of the series corresponding to the examination selected in the region 800 is displayed in the region 810 of the examination list displayed on the display 101*a*. Meanwhile, nothing is displayed on the display 101*b*.

FIG. 34 is a screen diagram of the examination list after an examination is selected. In the region 800 shown in FIG. 34, the background of a selected row is highlighted. In the example shown in FIG. 34, an examination on "Taro Pana" in the second row is selected in the region 800. Therefore, in the region 810, the "series ID", the "definition", and the "image" of the selected examination are displayed. In this case, the series ID associated with the examination ID of the selected examination in the medical image database 2000 is displayed in the "series ID" field and a thumbnail image of one slice image representing the displayed series ID is displayed in the "image" field. As the one slice image that represents the series ID, an image at a prescribed slice position is adopted. The prescribed slice position may be a top slice position or a central slice position. The "definition" indicates a photographic condition or a reconstruction condition with respect to a corresponding series. Although not shown, for example, the "definition" is registered in association with a series ID in the medical image database 2000 shown in FIG. 28.

Figure 35:
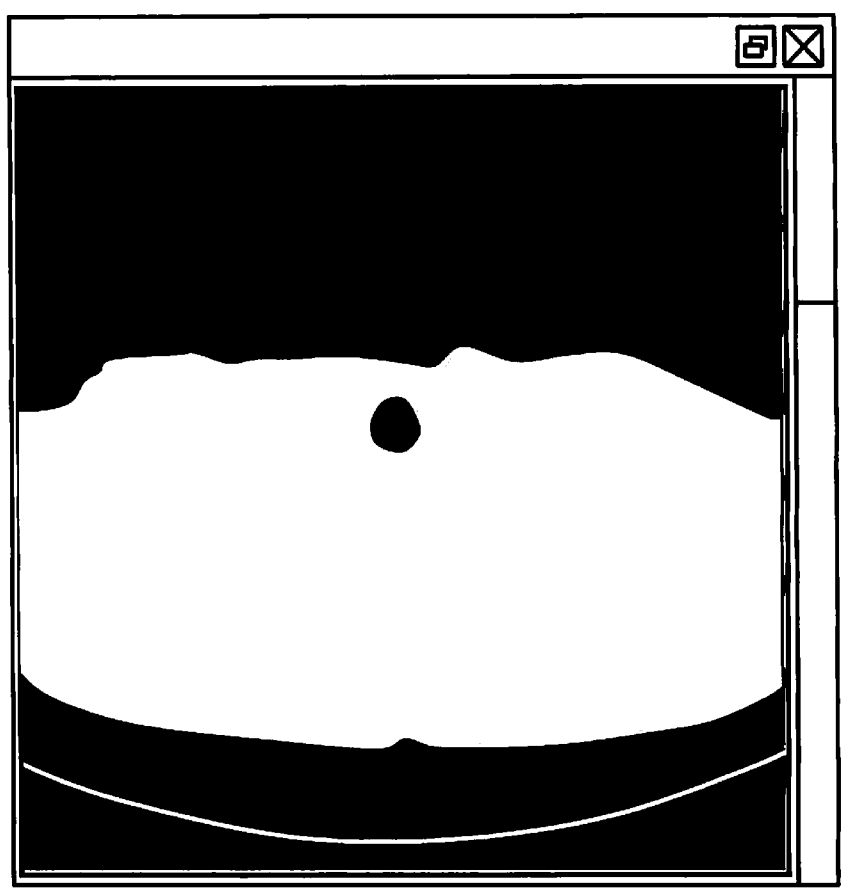
FIG. 35 is a diagram showing a slice image that is displayed on a medical image viewer when a series is selected by a user.

When a diagnostic interpretation object series is selected by the user in the region 810 and the input control unit 103 senses the selection, the display control unit 104 displays a top slice image of the selected series on the display 101*a* as shown in FIG. 35 (S570). FIG. 35 is a diagram showing a slice image that is displayed on the display 101*a* when a series is selected by the user. FIG. 35 is a diagram showing a top slice of a chest CT radiograph and is a slice image taken at a shoulder position that is slightly closer to the head than the pulmonary apex. At this point, the display control unit 104 displays all slice images of the selected series on the display 101*a* so that the slice images can be series-fed. Meanwhile, nothing is displayed on the display 101*b*. For example, the user positions a mouse pointer on the display 101*a* and inputs a slice feeding operation by rotating a mouse wheel, whereby the input control unit 103 senses the operation. As a result, the display control unit 104 switches the slice image displayed on the display 101*a* to a slice image at a different slice position in accordance with an amount of rotation of the mouse wheel. The user performs image diagnosis while inputting a slice feeding operation. In addition, when the user hesitates in performing the image diagnosis, the user starts the similar case retrieval application.

At this point, the similar case retrieval application may be started when a shortcut key determined in advance is input on a keyboard of the operating unit 102 or when a menu of a medical image viewer is displayed by a right click of the mouse and a similar case retrieval menu is specified from the menu. When an instruction to start the similar case retrieval application is issued, management of the information terminal 100 is handed over to the ROI managing unit 105 and the information terminal 100 enters a region of interest (ROI) standby state.

The user sets a region of interest (ROI) to a lesion on the slice image displayed on the display 101*a* through the operating unit 102 (S580). At this point, as shown in FIG. 31, for example, the user left-clicks the mouse to input coordinates of a top left vertex of the region of interest ROI in a slice image 3101. Subsequently, the user may input a bottom right vertex of the region of interest ROI by dragging the mouse diagonally rightward and downward while holding the left click of the mouse and then releasing the left click.

When the input control unit 103 senses an operation for setting a region of interest, the ROI managing unit 105 receives coordinate data of the top left and bottom right vertices of the region of interest from the input control unit 103 and generates region of interest information with the received coordinate data. In addition, the ROI managing unit 105 transmits the generated region of interest information to the communication control unit 110 (S590).

At the same time, the ROI managing unit 105 transmits a slice image of the diagnosis object case to the communication control unit 110 (S600). In this case, in S550, one slice image (retrieval query image) to which a region of interest has been set by the user in a series selected by the user is transmitted among the slice images of all series received by the information terminal 100 from the medical information management system 200.

Next, the communication control unit 110 receives the region of interest information transmitted from the ROI managing unit 105 and transmits the region of interest information to the communication control unit 304 of the case retrieval system 300 (S601).

At the same time, the communication control unit 110 receives the slice image transmitted from the ROI managing unit 105 and transmits the slice image to the communication control unit 304 of the case retrieval system 300 (S602).

While a slice image itself is transmitted in S600 and S601, only a slice ID of the slice image may be transmitted instead. In this case, the case retrieval system 300 having received the slice ID may acquire a slice image from the medical information management system 200 by specifying the slice ID.

Next, a process until the case retrieval system 300 performs similar case retrieval and the information terminal 100 initially displays a similar case retrieval result will be described.

FIG. 36A is a sequence diagram showing a process in which, after the case retrieval system 300 receives a request for similar case retrieval, the case retrieval system 300 sends back a similar case retrieval result to the information terminal 100.

The image feature extracting unit 302 of the case retrieval system 300 extracts an image feature of a plurality of number of dimensions determined in advance from the region of interest set in the retrieval query image (S610).

As an "image feature", an image feature related to a shape of an organ or a lesion portion in a medical image, an image feature related to brightness distribution, or the like can be adopted. For example, Non Patent Literature "Nemoto, Shimizu, Hagihara, Kobatake, and Nawano; Improvement of Tumor Detection Performance in Mammograms by Feature Selection from a Large Number of Features and Proposal of Fast Feature Selection Method; IEICE TRANSACTIONS on Information and Systems D-II, Vol. J88-D-II, No. 2, pp. 416-426, February 2005" describes using an image feature with 490 dimensions. In the present embodiment, for example, the image feature described in this Non Patent Literature is adopted. However, this is simply an example and other image features may be adopted instead.

The similar case retrieving unit 303 compares the image feature extracted by the image feature extracting unit 302 and an image feature of each similar case accumulated in the similar case data accumulating unit 301 with each other (S620). At this point, the similar case retrieving unit 303 compares both image features with each other by calculating a distance between image feature data extracted from the retrieval query image and image feature data 4400 registered in the similar case data 4000 (FIG. 30) accumulated for each similar case in the similar case data accumulating unit 301.

Next, the similar case retrieving unit 303 sorts similar cases with distances that are equal to or shorter than a prescribed threshold in an ascending order of distance and decides the similar cases to be transmission objects (S630). Next, among the similar case data 4000 accumulated in the similar case data accumulating unit 301, the communication control unit 304 transmits the similar case ID 4100, the slice ID 4200, the region of interest information 4300, the thumbnail image data 4500, the lesion distribution information 4600, the definitive diagnosis (broadly categorized disease name) 4700, and the definitive diagnosis (finely categorized disease name) 4800 of a similar case decided as the transmission object as well as the distance calculated by the similar case retrieving unit 303 to the information terminal 100 (S640).

Hereinafter, a process is executed for generating an initial basic screen K2 (FIG. 6) on which a similar case retrieval result is displayed. First, management information that is used when generating the layout region 720 on the initial basic screen K2 will be described.

First, the communication control unit 304 of the case retrieval system 300 transmits layout information to the information terminal 100 (S650). In this case, layout information refers to information that specifies the number of rows and the number of columns of display boxes constituting the layout region 720.

Next, when the communication control unit 110 of the information terminal 100 receives the layout information, the display box managing unit 106 registers the number of rows and the number of columns of display boxes specified by the transmitted layout information in display box management information 4410 (FIG. 36B) and, at the same time, registers the slice ID of the retrieval query image in display box management information (FIG. 36B) (S660).

FIG. 36B is a diagram showing a data configuration of the display box management information 4410. The display box management information 4410 includes a table 4411 in which number of rows and the number of columns are registered and a table 4412 in which a slice ID of the slice image displayed in each display box is registered. Therefore, the display box managing unit 106 registers the number of rows and the number of columns of display boxes specified by the layout information transmitted from the case retrieval system 300 in the number of row field and the number of column field of the table 4411. In addition, in the present embodiment, a thumbnail image of the retrieval query image is displayed in a top left display box 721 among the four display boxes 721 to 724. Therefore, the display box managing unit 106 registers the slice ID of the retrieval query image transmitted from the medical information management system 200 in a 1st-row, 1st-column item of the table 4412.

In this case, default values of the number of rows and the number of columns of display boxes constituting the layout region 720 are set in advance by the case retrieval system 300. The default values of the number of rows and the number of columns are, for example, two rows and two columns. Therefore, "2 rows and 2 columns" are registered in the display box management information 4410 shown in FIG. 36B.

In the example shown in FIG. 6, the display boxes 721 to 724 are displayed in two rows and two columns in the layout region 720. The number of rows and the number of columns in the layout region 720 can be set at will by the user.

Figure 36C:
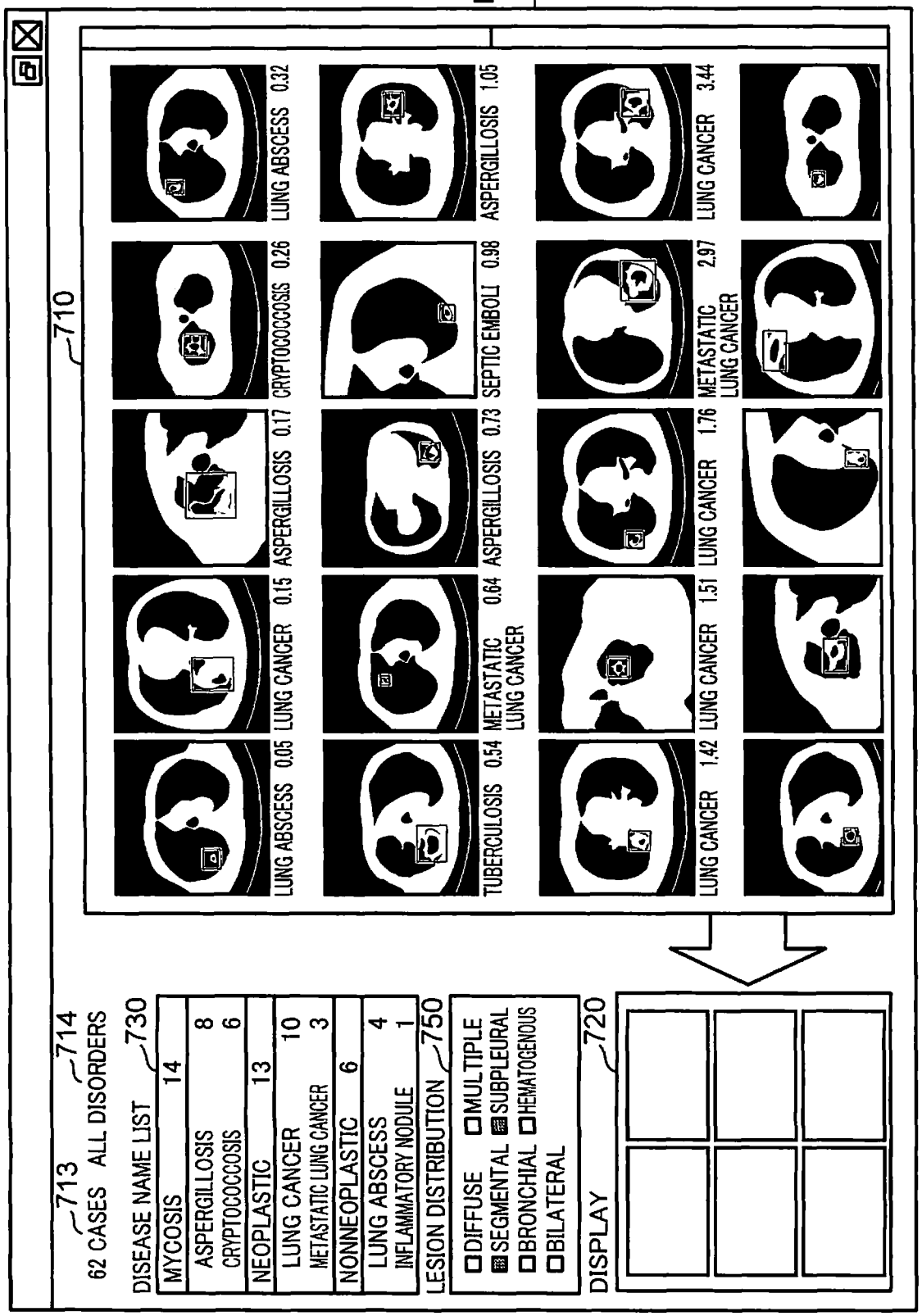
FIG. 36C is a diagram showing a basic screen having a layout region in which display boxes are set in three rows and two columns.

FIG. 36C is a diagram showing the basic screen K2 having the layout region 720 in which display boxes are set in three rows and two columns. If the display boxes constituting the layout region 720 are to be generalized as M rows and N columns, when M≠N, it is desirable that M>N when the display 101 is an upright display and desirable that M<N when the display 101 is a horizontal display.

An important feature of the present embodiment is that a thumbnail image of a diagnosis object case is displayed in one display box among the display boxes constituting the layout region 720. In other words, by displaying a similar case and a diagnosis object case adjacent to each other, the user can more easily determine the degree of similarity between both cases. Therefore, the arrangement of the display boxes in the layout region 720 is desirably set to three rows and three columns at the most.

In addition, when the arrangement of the display boxes is three rows and two columns, the thumbnail image of the retrieval query image is favorably displayed in the 2nd-row, 1st-column display box or the 2nd-row, 2nd-column display box. Furthermore, when the arrangement of the display boxes is two rows and three columns, the thumbnail image of the retrieval query image is favorably displayed in the 1st-row, 2nd-column display box or the 2nd-row, 2nd-column display box. Moreover, when the arrangement of the display boxes is three rows and three columns, the thumbnail image of the retrieval query image is favorably displayed in the 2nd-row, 2nd-column display box. Accordingly, the similar case is to be always displayed adjacent to the diagnosis object case in the layout region 720.

Layout information of the layout region 720 set by the user is registered in layout management information 4200 shown in FIG. 36D or 36E.

Moreover, the box layout managing unit 111 that stores the layout management information 4200 may be included in the case retrieval system 300.

Even for the same user, a layout of the layout region 720 may be changed so as to accommodate a size or a screen type (upright or horizontal) of the display 101 of the information terminal 100. Therefore, as shown in FIG. 36D, the layout information set by the user may be registered in the layout management information 4200 in association with a user ID and a terminal ID. FIG. 36D is a diagram showing an example of the layout management information 4200. In the layout management information 4200, a "user ID", a "terminal ID", the "number of columns", the "number of rows", and a "position of diagnosis object case" are associated with each other. In this case, the "user ID" is an identifier that is assigned to a user who uses the information terminal 100 in advance. The "terminal ID" is an identifier of the information terminal 100 that is expected to be used by a corresponding user.

In the example shown in FIG. 36D, since the user with a user ID "U01" is expected to use terminal IDs "T02" and "T04", the user ID "U01" is associated with the terminal IDs "T02" and "T04". The number of rows and the number of columns of the layout region 720 as set by a corresponding user are registered in the "number of columns" and the "number of rows". The "position of diagnosis object case" represents a position of a display box that displays the diagnosis object case. For example, in the information terminal 100 with the terminal ID "T04", the layout region 720 is set to two rows and three columns, and (2,1) indicating the 2nd row and 1st column is registered as the "position of diagnosis object case" so that the diagnosis object case is displayed adjacent to all of the similar cases.

Moreover, while a mode in which layout information is managed in association with a user ID and a terminal ID has been shown in FIG. 36D, layout information may be managed in association with only a user ID. FIG. 36E is a diagram showing an example of the layout management information 4200. In the layout management information 4200 shown in FIG. 36E, the "terminal ID" field has been omitted from the layout management information 4200 shown in FIG. 36D. Otherwise, the layout management information 4200 shown in FIG. 36E is the same as the layout management information 4200 shown in FIG. 36D. Moreover, in the mode shown in FIG. 36E, since one user had been expected to use one information terminal 100, the "terminal ID" field is omitted.

When layout information is managed by the case retrieval system 300, layout information of a corresponding user is transmitted to the information terminal 100 in S650 in FIG. 36A.

Next, using the similar case data transmitted in S640 and the display box management information 4410 stored in S660, the display control unit 104 generates the initial basic screen K2 on which a similar case retrieval result is displayed (S670).

In this case, the basic screen K2 shown in FIG. 6 is displayed on the display 101b. In addition, the retrieval query image is displayed on the display 101a.

Figure 37:
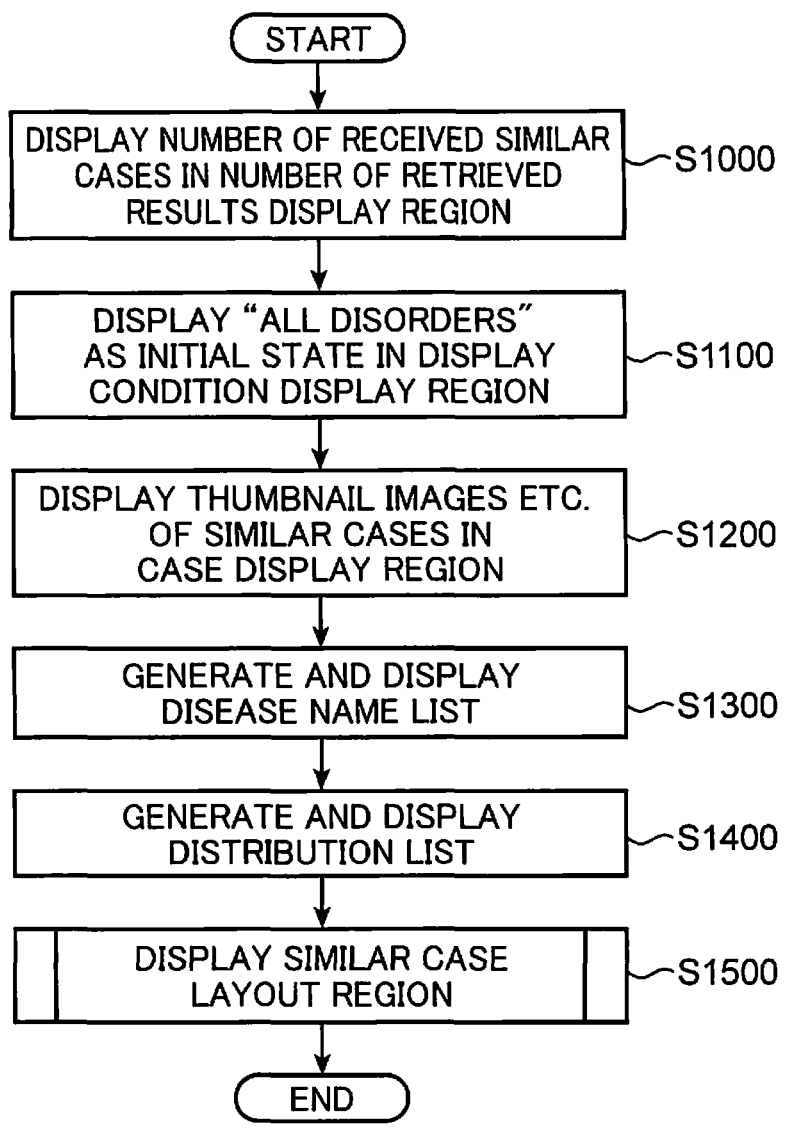
FIG. 37 is a flow chart showing details of a process for generating an initial basic screen shown in S670 in FIG. 36A.

FIG. 37 is a flow chart showing details of the process for generating the initial basic screen K2 shown in S670 in FIG. 36A.

First, in S1000, the display control unit 104 counts the number of similar cases received in S640 shown in FIG. 36A and displays the count value in the number of retrieved results display region 713.

Next, in S1100, the display control unit 104 displays "all disorders" in the display condition display region 714. "All disorders" is displayed at this point because, on the initial basic screen K2, similar cases have not yet been narrowed down by a disease name or a lesion distribution by the user.

Next, in S1200, the display control unit 104 displays thumbnail images of similar cases in the case display region 710 for the number of similar cases for which thumbnail images can be displayed in the case display region 710 among the similar cases received in S640 shown in FIG. 36A and, at the same time, displays a definitive diagnosis and a degree of similarity in association with each thumbnail image.

In the example shown in FIG. 6, the maximum value of the number of similar cases that can be displayed in the case display region 710 is 20. This maximum value is determined in advance. Alternatively, a configuration may be adopted in which the user can change the maximum value at will. When the number of similar cases received in S640 shown in FIG. 36A is larger than the maximum value, the display control unit 104 displays the scroll bar 715 that is elongated in a vertical direction at a right end of the case display region 710. Accordingly, the user can move the scroll bar 715 and view thumbnail images of similar cases which had been hidden on the initial basic screen K2.

Next, in S1300, a disease name list is generated and displayed. First, a disease name list is generated from the similar cases received in S640 shown in FIG. 36A. The disease name list is a list in which the similar cases received in S640 are classified according to definitively diagnosed disease names.

Figure 38:
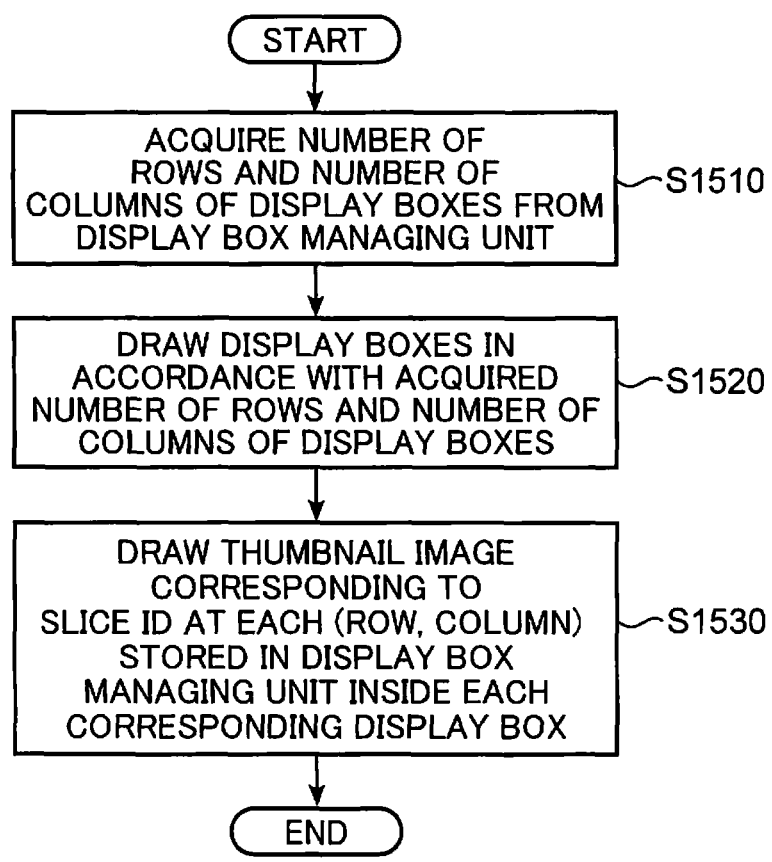
FIG. 38 is a flow chart showing a process of S1500 shown in FIG. 37.

Let us assume that the number of similar cases received in S640 is expressed as NC. The disease name list managing unit 108 generates the disease name list using the definitive diagnosis (broadly categorized disease name) 4700 and the definitive diagnosis (finely categorized disease name) 4800 respectively registered in the NC-number of pieces of similar case data 4000. The generated disease name list is managed by the disease name list managing unit 108 as table format data as shown in FIG. 38.

FIG. 39 is a diagram showing a data configuration of a disease name list that is generated in S1300 shown in FIG. 37. The disease name list includes fields of a "disease name ID", a "broadly categorized disease name", a "finely categorized disease name", the "number of cases", and a "similar case ID". The "disease name ID" is an identifier assigned to each definitively diagnosed disease name. In this case, one disease name ID is assigned to one combination of a broadly categorized disease name and a finely categorized disease name.

The "broadly categorized disease name" is the definitively diagnosed disease name represented by the definitive diagnosis (broadly categorized disease name) 4700 registered in the similar case data 4000. The "finely categorized disease name" is the definitively diagnosed disease name represented by the definitive diagnosis (finely categorized disease name) 4800 registered in the similar case data 4000. The "number of cases" is the number of similar cases corresponding to the definitively diagnosed disease name represented by the "disease name ID". The "similar case ID" is a similar case ID representing a similar case corresponding to the disease name represented by the "disease name ID".

The disease name list managing unit 108 extracts the definitive diagnosis (broadly categorized disease name) 4700 and the definitive diagnosis (finely categorized disease name) 4800 for all pieces of similar case data 4000 received in S640 and classifies the same similar case data 4000 as the similar case of a same definitively diagnosed disease name for both definitive diagnoses. In addition, the disease name list managing unit 108 counts the number of similar cases with the same definitively diagnosed disease name and registers the number of similar cases in the "number of cases" field in a record of a corresponding definitively diagnosed disease name. Furthermore, the disease name list managing unit 108 registers a similar case ID of a similar case classified as a same definitively diagnosed disease name in the "similar case ID" field in a record of a corresponding definitively diagnosed disease name.

In the example shown in FIG. 39, a disease name ID "DIS528" is assigned to a definitively diagnosed disease name whose broadly categorized disease name is "neoplastic" and whose finely categorized disease name is "lung cancer". In addition, since the number of similar cases corresponding to the definitively diagnosed disease name is 10, 10 is registered in the "number of cases" field of a corresponding record and similar case IDs "SIM258", "SIM551", "SIM1209", "SIM2341", and the like of similar cases corresponding to the definitively diagnosed disease name are registered in the "similar case ID" field of the corresponding record.

Subsequently, the display control unit 104 generates the disease name list display region 730 using the disease name list generated as described above and displays the disease name list display region 730 on the display 101.

FIGS. 40, 41, and 42 are, respectively, diagrams showing a first display example, a second display example, and a third display example of the disease name list display region 730. As shown in FIG. 40, in the first display example, similar cases obtained as a result of a similar case retrieval are displayed associated with the number of cases of a finely categorized disease name in a descending order of the number of cases as a list.

As shown in FIG. 41, in the second display example, similar cases obtained as a result of a similar case retrieval are displayed associated with the number of cases of a broadly categorized disease name in a descending order of the number of cases as a list.

As shown in FIG. 42, in the third display example, similar cases obtained as a result of a similar case retrieval are displayed associated with the number of cases of a broadly categorized disease name in a descending order of the number of cases as a list and, for each broadly categorized disease name, the finely categorized disease names included in the broadly categorized disease name are displayed associated with the number of cases in a descending order of the number of cases as a list. In this case, a definitively diagnosed disease name is expressed by a hierarchical structure of a broadly categorized disease name and a finely categorized disease name.

Figure 43:
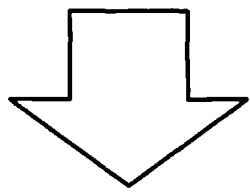
FIG. 43 is a diagram showing a screen transition of the disease name list display region shown in FIG. 41.

FIG. 43 is a diagram showing a screen transition of the disease name list display region 730 shown in FIG. 41. As shown in an upper part of FIG. 43, when the input control unit 103 senses an operation by a user for selecting one broadly categorized disease name among the broadly categorized disease names displayed as a list, the display control unit 104 displays the finely categorized disease names belonging to the selected broadly categorized disease name in association with the number of cases in a descending order of the number of cases as shown in a lower part of FIG. 43. At this point, for example, the user may select one broadly categorized disease name by double-clicking or single-clicking one desired broadly categorized disease name among the broadly categorized disease names displayed as a list in the disease name list display region 730. In the example shown in FIG. 43, since nonneoplastic has been double-clicked, the finely categorized disease names belonging to nonneoplastic are displayed as a list.

In the lower part of FIG. 43, when a region in which the finely categorized disease names are displayed as a list is double-clicked or single-clicked by the user, the display control unit 104 may hide the finely categorized disease names that had been displayed in the corresponding region.

Moreover, the display control unit 104 may judge the finely categorized disease names belonging to the broadly categorized disease name by referring to the disease name list (FIG. 39). For example, in the example shown in FIG. 39, since aspergillosis and cryptococcosis are associated with mycosis, the display control unit 104 may determine that aspergillosis and cryptococcosis belong to mycosis.

Returning now to FIG. 37, in S1400, a distribution list is generated and displayed. First, a distribution list is generated from the similar cases received in S640. The distribution list is a list in which the similar cases received in S640 are classified according to lesion distributions.

The disease name list managing unit 108 generates a distribution list using lesion distribution information 4600 registered in each similar case data 4000 of the NC-number of cases. The generated distribution list is managed by the distribution list managing unit 109 as table format data as shown in FIG. 44A.

FIG. 44A is a diagram showing a data configuration of a distribution list that is generated in S1400 shown in FIG. 37. The disease name list includes fields of a "distribution name", the "number of cases", and a "similar case ID". The "distribution name" is a name of plurality of lesion distributions determined in advance such as diffuse and segmental. The "number of cases" represents the number of similar cases corresponding to a lesion distribution. The "similar case ID" is a similar case ID representing a similar case corresponding to a lesion distribution.

The distribution list managing unit 109 extracts lesion distribution information 4600 for all pieces of similar case data 4000 received in S640, counts the number of lesion distributions for which 1 (applicable) is set to the distribution flag value in the extracted lesion distribution information 4600, and registers the count value in the "number of cases" field of a record of a corresponding lesion distribution. In addition, the distribution list managing unit 109 registers a similar case ID of a similar case for which 1 is set to the distribution flag value in the "similar case ID" field in the record of a corresponding lesion distribution.

In the example shown in FIG. 44A, since there are three similar cases corresponding to diffuse, 3 is registered in the "number of cases" of the record of diffuse. In addition, similar case IDs "SIM2521", "SIM4123", and "SIM5225" representing similar cases corresponding to diffuse are registered in the "similar case ID" field of the record of diffuse.

Subsequently, the display control unit 104 generates the distribution list display region 750 using the distribution list generated as described above and displays the distribution list display region 750 on the display 101.

FIG. 44B is a diagram showing the distribution list display region 750 generated using the distribution list shown in FIG. 44A. In FIG. 44A, since the numbers of cases of segmental and subpleural are zero, in FIG. 44B, segmental 752 and subpleural 756 are displayed in an inactive state and since other lesion distributions have one or more cases, the other lesion distributions are displayed in an active state.

Returning now to FIG. 37, in S1500, the layout region 720 is displayed. This process is performed by the display control unit 104.

FIG. 38 is a flow chart showing a process of S1500 shown in FIG. 37. In S1510, the display control unit 104 acquires the number of rows and the number of columns of display boxes constituting the layout region 720 from the display box management information 4410 set in S660. In the example of the display box management information 4410 shown in FIG. 36B, since two rows and two columns are set as the number of rows and the number of columns, information reading "2 rows and 2 columns" is acquired. Moreover, when the user has changed the number of rows and the number of columns of display boxes, the number of rows and the number of columns of display boxes constituting the layout region 720 are acquired from the layout management information 4200 shown in FIG. 36D or 36E.

Next, in S1520, the display control unit 104 draws display boxes in accordance with the number of rows and the number of columns of display boxes acquired in S1510.

Finally, in S1530, the display control unit 104 identifies a slice ID of each display box from the display box management information 4410 and draws a thumbnail image corresponding to the identified slice ID in each corresponding display box.

In the example shown in FIG. 36B, the slice ID of a diagnosis object case is stored in the 1st-row, 1st-column display box. Therefore, the display control unit 104 generates a thumbnail image from the slice ID of the diagnosis object case transmitted in S600 shown in FIG. 32 and draws the generated thumbnail image in the display box 721.

At this stage, since slice IDs are not stored in the remaining display boxes (the 1st-row, 2nd-column display box 722, the 2nd-row, 1st-column display box 723, and the 2nd-row, 2nd-column display box 724), the display control unit 104 does not display anything in these display boxes. A thumbnail image of a similar case is to be displayed in these display boxes by a process to be described later.

Returning now to FIG. 36A, the communication control unit 110 transmits the display box management information 4410 stored in the display box managing unit 106 to the display control unit 104 (S680).

Next, the display control unit 104 starts a medical image viewer in a same display state and a same layout as a display state and a layout of the layout region 720 (S690).

Figure 45:
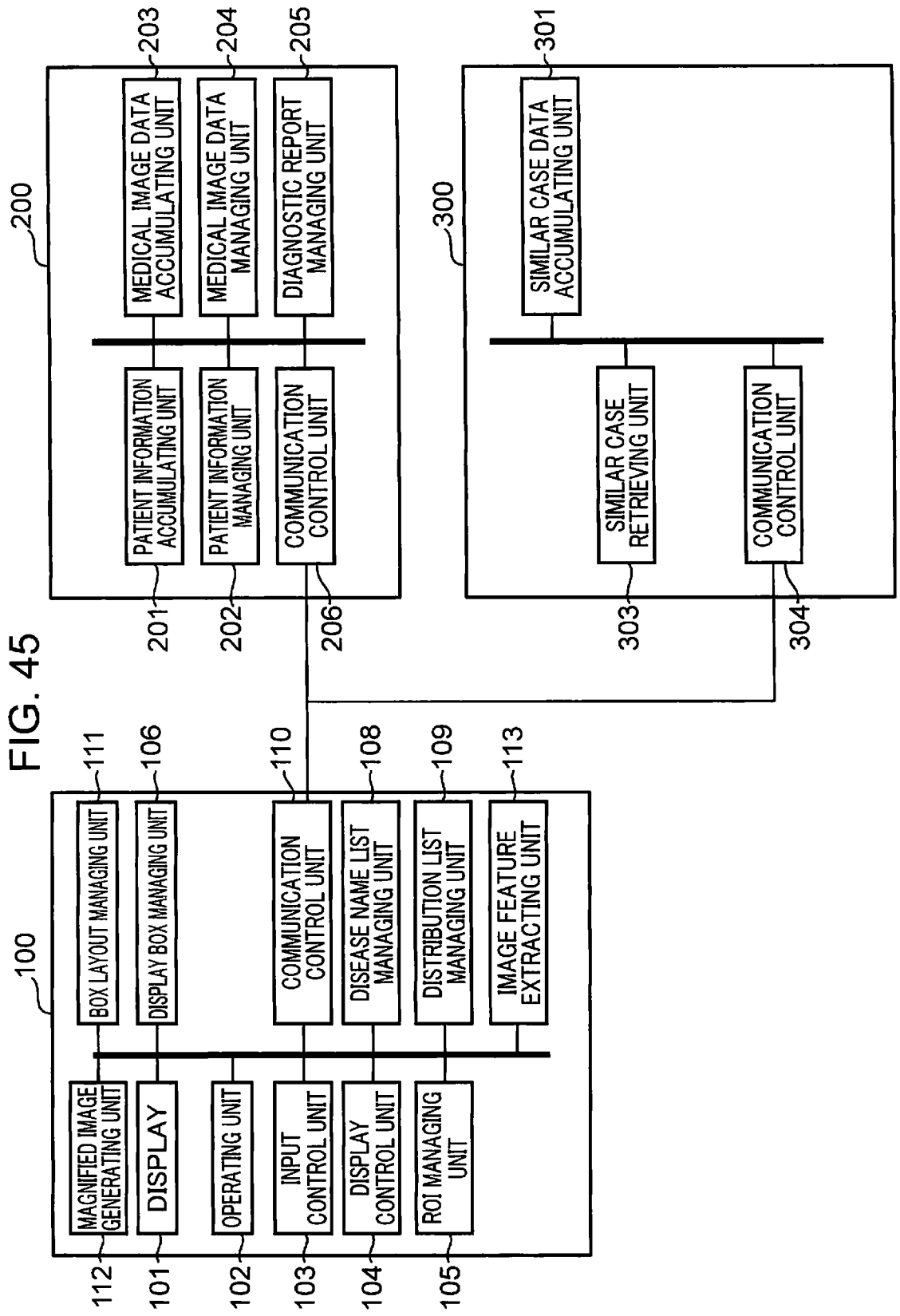
FIG. 45 is a block diagram of an information terminal, a medical information management system, and a case retrieval system when a mode is adopted in which the case retrieval system extracts an image feature.

While an example in which the case retrieval system 300 extracts an image feature has been shown, alternatively, the information terminal 100 may extract an image feature. FIG. 45 is a block diagram of the information terminal 100, the medical information management system 200, and the case retrieval system 300 when a mode is adopted in which the case retrieval system 300 extracts an image feature.

Differences from FIG. 2 are that the image feature extracting unit 112 has been added to the information terminal 100 and that the image feature extracting unit 302 has been omitted from the case retrieval system 300.

Figure 46:
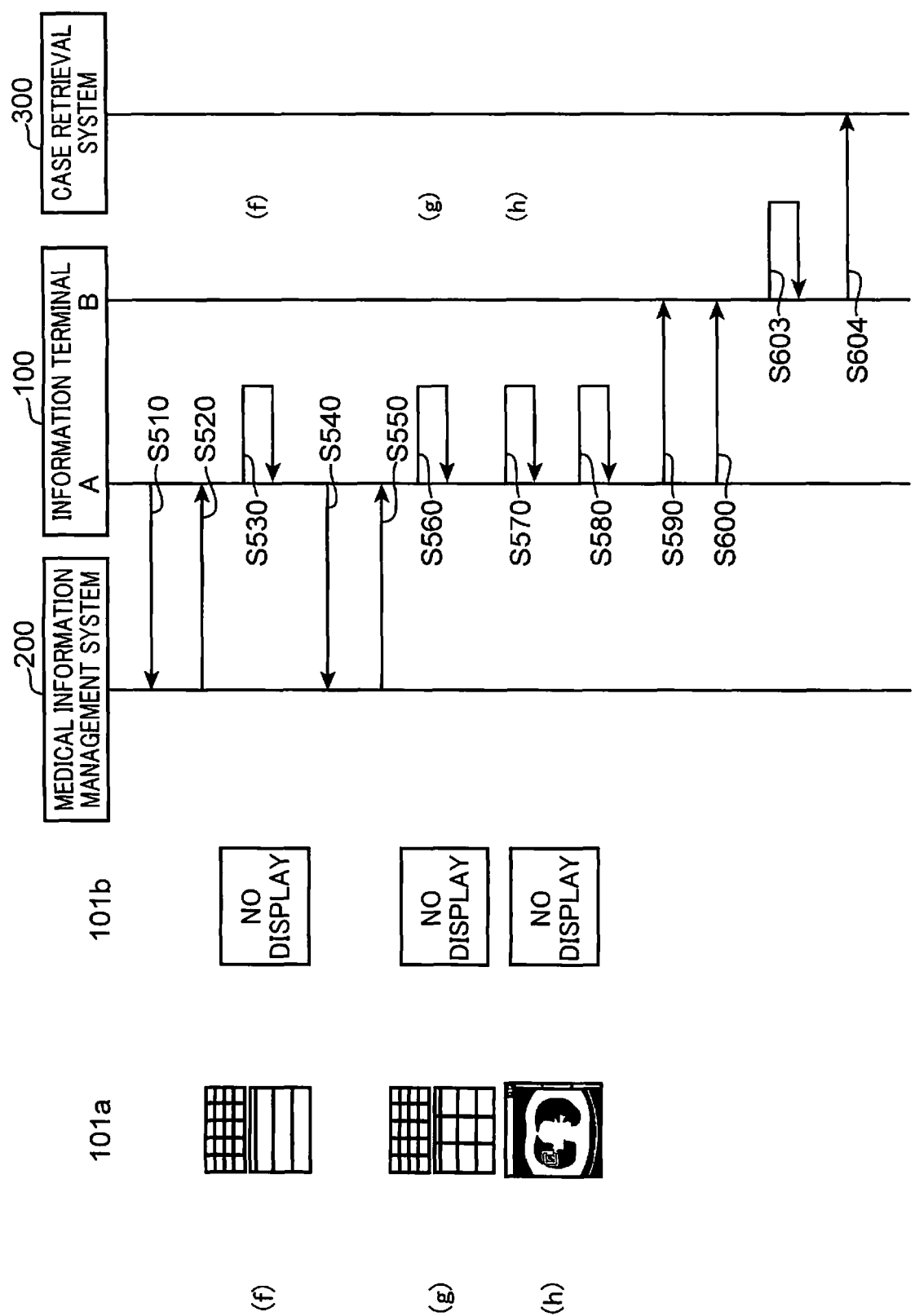
FIG. 46 is a sequence diagram showing a process in which, after an information terminal acquires a diagnosis object case from a medical information management system, a case retrieval system receives a request for similar case retrieval.

FIG. 46 is a sequence diagram showing a process in which, after the information terminal 100 acquires a diagnosis object case from the medical information management system 200, the case retrieval system 300 receives a request for similar case retrieval.

Differences from FIG. 32 are that, after a process by the ROI managing unit 105 for transmitting a slice image of a diagnosis object case to the communication control unit 110 (S600), extraction of an image feature is performed by the information terminal 100 (S603) and the extracted image feature is transmitted to the case retrieval system 300 (S604). The process content of image feature extraction (S604) is similar to the image feature extraction performed by the case retrieval system 300.

Figure 47:
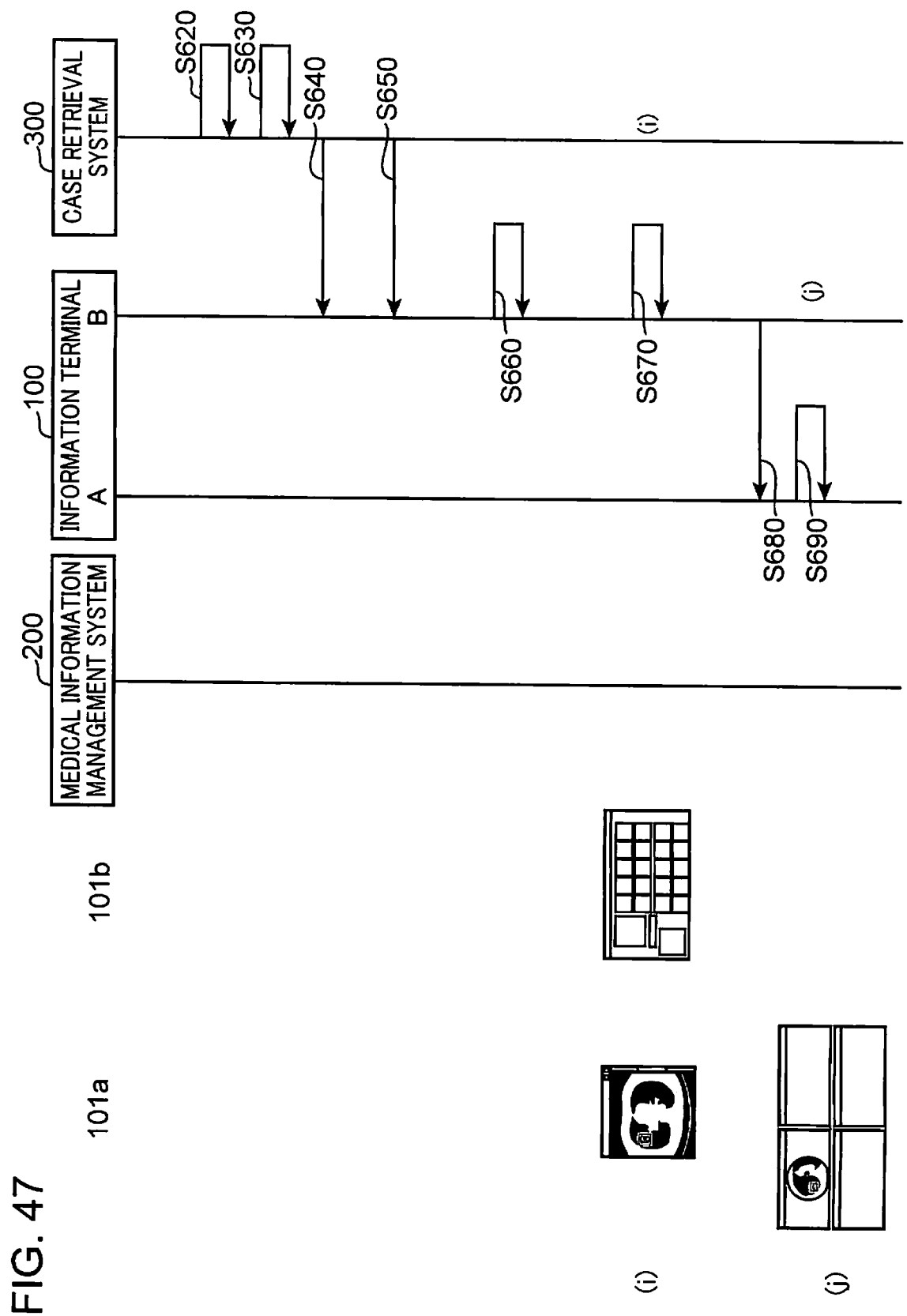
FIG. 47 is a sequence diagram showing a process in which, after a case retrieval system receives a request for similar case retrieval, the case retrieval system sends back a similar case retrieval result to an information terminal.

FIG. 47 is a sequence diagram showing a process in which, after the case retrieval system 300 receives a request for similar case retrieval, the case retrieval system 300 sends back a similar case retrieval result to the information terminal 100. A difference from FIG. 36A is that, since image feature extraction is performed by the information terminal 100, the image feature extraction (S610) included in FIG. 36A has been omitted in FIG. 47.

Next, a magnification process of thumbnail images displayed in the case display region 710 described with reference to FIGS. 8 to 15 will be described.

Figure 48:
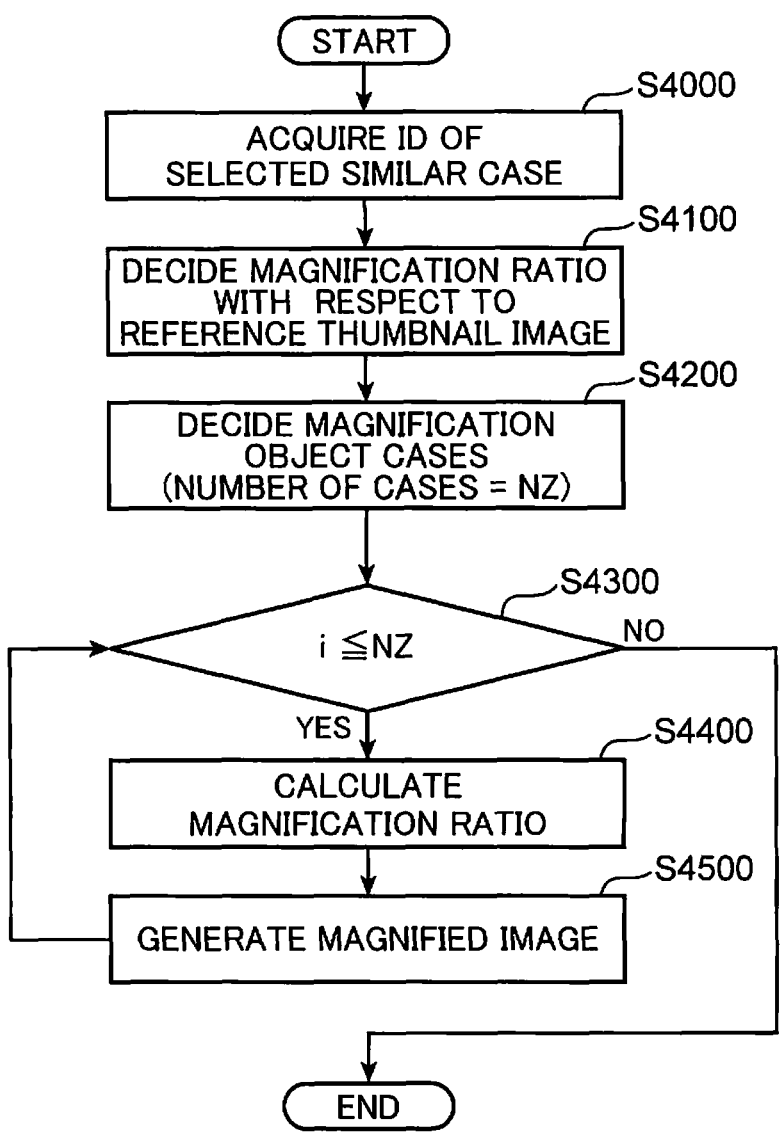
FIG. 48 is a flow chart showing a magnification process of thumbnail images that are displayed in a case display region.

FIG. 48 is a flow chart showing a magnification process of thumbnail images that are displayed in the case display region 710.

In S4000, the magnified image generating unit 112 acquires a similar case ID 4100 (FIG. 30) of the thumbnail image (2nd-row, 4th-column in FIG. 8) selected by the user. Hereinafter, a thumbnail image selected by the user will be referred to as a reference thumbnail image. The magnified image generating unit 112 decides a magnification ratio of other thumbnail images displayed in the case display region 710 in connection with a magnification operation by the user with respect to the reference thumbnail image.

In S4100, the magnified image generating unit 112 acquires an operation amount of the magnification operation with respect to the reference thumbnail image which is input to the operating unit 102 by the user from the input control unit 103. In addition, the magnified image generating unit 112 decides a magnification ratio with respect to the reference thumbnail image based on the acquired operation amount.

Specifically, the input control unit 103 senses an amount of rotation of the wheel of the mouse which is input as a magnification operation to the operating unit 102. The input control unit 103 notifies the magnified image generating unit 112 of the sensed amount of rotation. The magnified image generating unit 112 calculates the magnification ratio with respect to the reference thumbnail image by multiplying the amount of rotation by a coefficient determined in advance.

As described earlier, the magnification operation by the user may involve an upward key or a downward key of a keyboard. In this case, the input control unit 103 may sense a depression time of the key. The magnified image generating unit 112 may calculate the magnification ratio with respect to the reference thumbnail image by multiplying the depression time of the key by a coefficient determined in advance.

In S4200, the magnified image generating unit 112 decides object similar cases on which a magnification process is to be performed among a large number of similar cases acquired from the case retrieval system 300. As shown in FIG. 6, the display control unit 104 displays, in the case display region 710, a maximum number ND (ND=20 in the present embodiment) of displayable cases as determined in advance by the case display region 710 among similar case data of NC (NC=62 in FIG. 6) number of cases retrieved by the similar case retrieving unit 303 of the case retrieval system 300.

In the present step, the magnified image generating unit 112 decides object similar cases on which a magnification process is to be performed within a range of ND or fewer so as to include the thumbnail image selected by the user. In the present embodiment, the magnified image generating unit 112 decides NZ number of similar cases as objects on which a magnification process is to be performed, where NZ≤ND. According to the present step, compared to a case where thumbnail images of all of the NC number of similar cases are magnified, the processing load on the information terminal 100 can be reduced.

In S4300, the magnified image generating unit 112 decides a thumbnail image of a similar case i (where i is an index specifying a similar case that is a processing object and is an integer not less than 1) as a thumbnail image that is a processing object. Subsequently, the magnified image generating unit 112 repeats the processes of S4400 and S4500 until the index i reaches NZ (YES in S4300). The magnified image generating unit 112 increments the index i by 1 each time the processes of S4400 and S4500 are executed. Once the index i exceeds NZ (NO in S4300), the process shown in FIG. 48 is finished.

In S4400, the magnified image generating unit 112 calculates a magnification ratio of the thumbnail image of the similar case i that is the magnification object. Based on the magnification ratio with respect to the reference thumbnail image as decided in S4100, the region of interest information 4300 (FIG. 30) of a similar case corresponding to the reference thumbnail image, and the region of interest information 4300 (FIG. 30) of the similar case i that is the magnification object, the magnified image generating unit 112 calculates a magnification ratio of the similar case i that is the magnification object.

Figure 49:
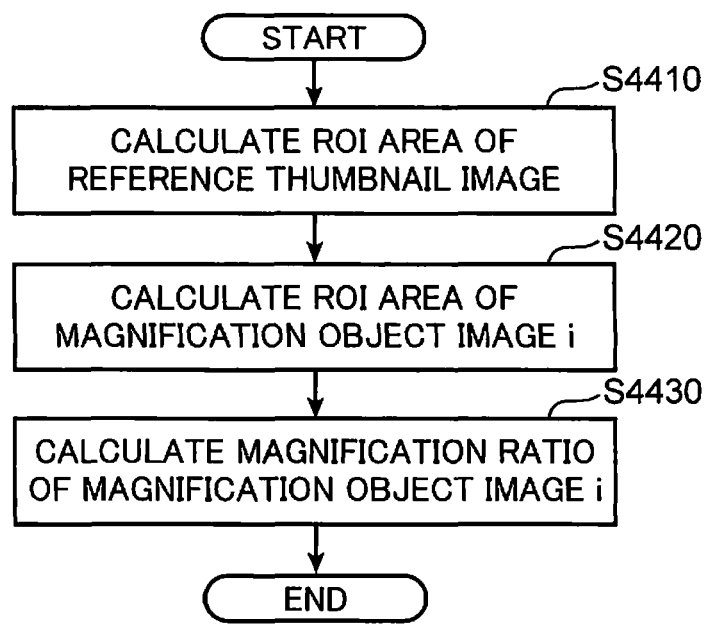
FIG. 49 is a flow chart showing a process of a subroutine of S4400 in FIG. 48.

FIG. 49 is a flow chart showing a process of the subroutine of S4400 in FIG. 48.

In S4410, the magnified image generating unit 112 calculates an area of the region of interest of the reference thumbnail image based on the region of interest information 4300 of the similar case corresponding to the reference thumbnail image. In this case, if the area of the region of interest of the reference thumbnail image is denoted by Sr, top left coordinates of the region of interest are denoted by (xl, yt), and bottom right coordinates of the region of interest are denoted by (xr, yb), then the area Sr of the region of interest can be calculated according to the equation below.

$$Sr = |xl - xr| \times |yt - yb|$$

In S4420, based on the region of interest information 4300 of the similar case i that is the magnification object, the magnified image generating unit 112 calculates an area of the region of interest of the thumbnail image of the similar case i that is the magnification object. In this case, if the area of the region of interest of the thumbnail image of the similar case i that is the magnification object is denoted by Si, top left coordinates of the region of interest are denoted by (xli, yti), and bottom right coordinates of the region of interest are denoted by (xri, ybi), then the area Si of the region of interest can be calculated according to the equation below.

$$Si = |xli - xri| \times |yti - ybi|$$

In S4430, the magnified image generating unit 112 calculates the magnification ratio of the similar case i that is the magnification object based on the area Sr of the region of interest of the reference thumbnail image calculated in S4410, the area Si of the region of interest of the thumbnail image of the similar case i that is the magnification object calculated in S4420, and the magnification ratio with respect to the reference thumbnail image as decided in S4100. In this case, if the magnification ratio with respect to the reference thumbnail image is denoted by kr, then a magnification ratio ki of the similar case i that is the magnification object can be calculated according to the equation below.

$$ki = kr(Sr/Si)$$

Figure 50:
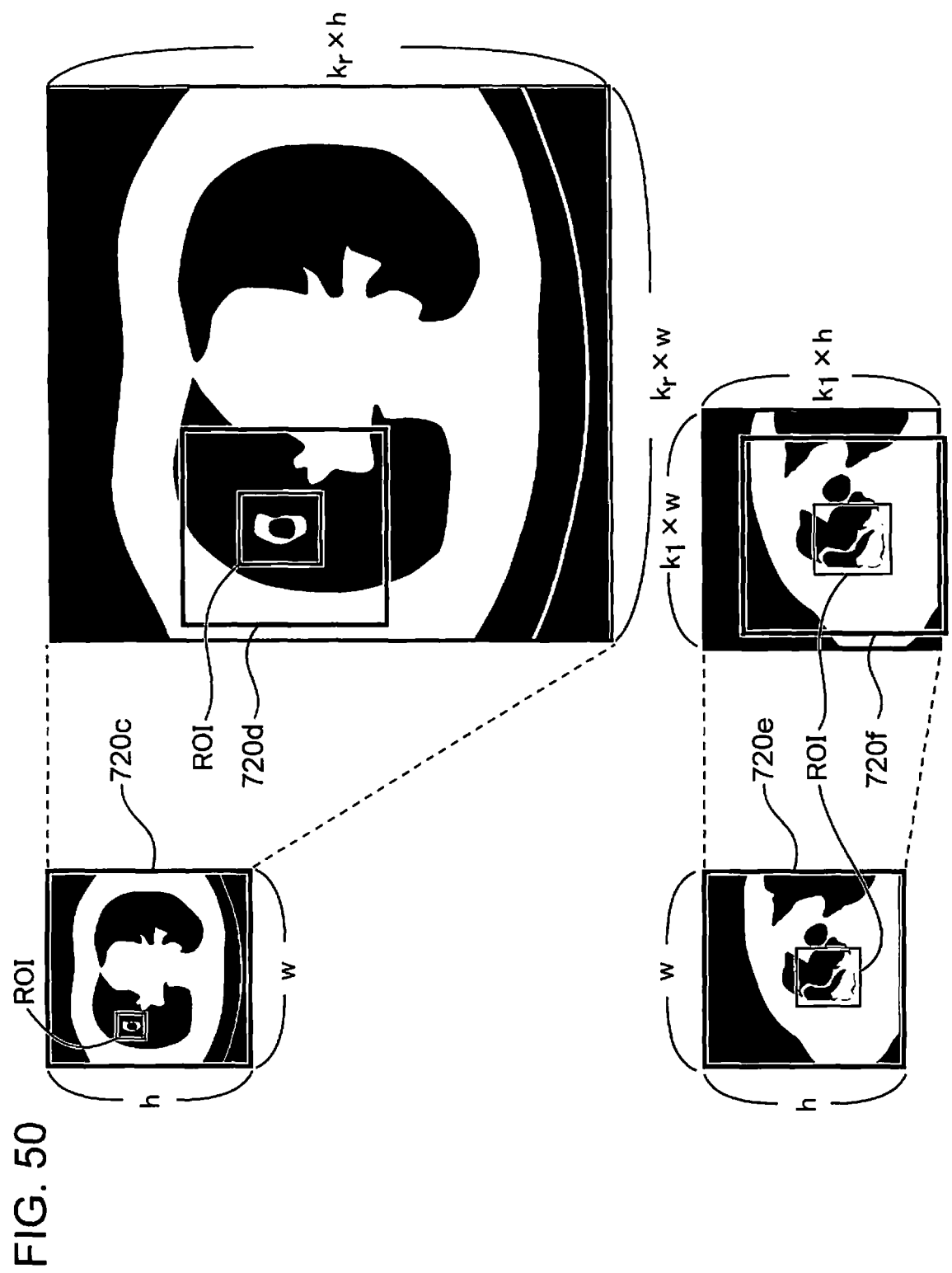
FIG. 50 is a diagram schematically showing a reference thumbnail image and a thumbnail image that is a magnification object before and after a magnification process.

FIG. 50 is a diagram schematically showing a reference thumbnail image and a thumbnail image that is a magnification object before and after a magnification process. A top left diagram in FIG. 50 shows a reference thumbnail image before the magnification process. A top right diagram in FIG. 50 shows the reference thumbnail image after the magnification process. A bottom left diagram in FIG. 50 shows the thumbnail image that is the magnification object before the magnification process. A bottom right diagram in FIG. 50 shows the thumbnail image that is the magnification object after the magnification process.

By magnifying the reference thumbnail image shown in the top left diagram in FIG. 50 at the magnification ratio kr, the thumbnail image shown in the top right diagram in FIG. 50 is obtained. The magnified image generating unit 112 decides a display region 720d so that a center position of a region of interest ROI matches a center position of the display region 720d in the top right diagram in FIG. 50. The magnified image generating unit 112 maintains a size of the display region 720d at a same size as a size of a display region 720c before the magnification process.

By magnifying the thumbnail image that is the magnification object shown in the bottom left diagram in FIG. 50 at the magnification ratio ki, the thumbnail image shown in the bottom right diagram in FIG. 50 is obtained. The magnified image generating unit 112 sets a display region 720f so that a center position of the region of interest ROI matches a center position of the display region 720f in the bottom right diagram in FIG. 50. The magnified image generating unit 112 maintains a size of the display region 720f at a same size as a size of a display region 720e before the magnification process.

In FIG. 50, with respect to the magnification ratio kr of the reference thumbnail image, the magnification ratio ki of the thumbnail image i that is the magnification object is decided in accordance with an area ratio of regions of interest. Therefore, as shown in FIG. 50, a size of the region of interest ROI after magnification is the same.

Returning now to FIG. 48, in S4500, the magnified image generating unit 112 generates a magnified thumbnail image of the similar case i that is the magnification object based on the magnification ratio calculated in S4400, and the region of interest information 4300 and the thumbnail image data 4500 in the similar case data 4000 (FIG. 30). The display control unit 104 displays the thumbnail image generated by the magnified image generating unit 112.

Figure 51:
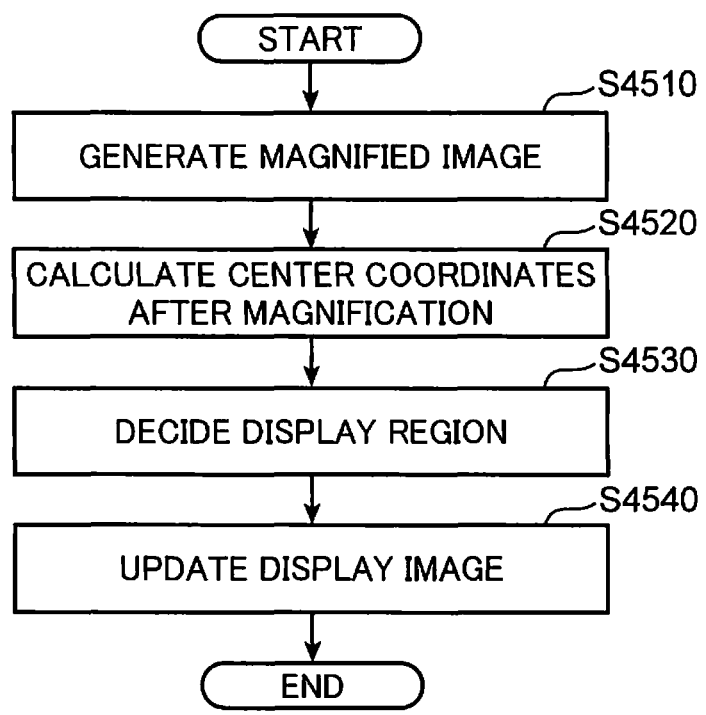
FIG. 51 is a flow chart showing a process of a subroutine of S4500 in FIG. 48.
Figure 52:
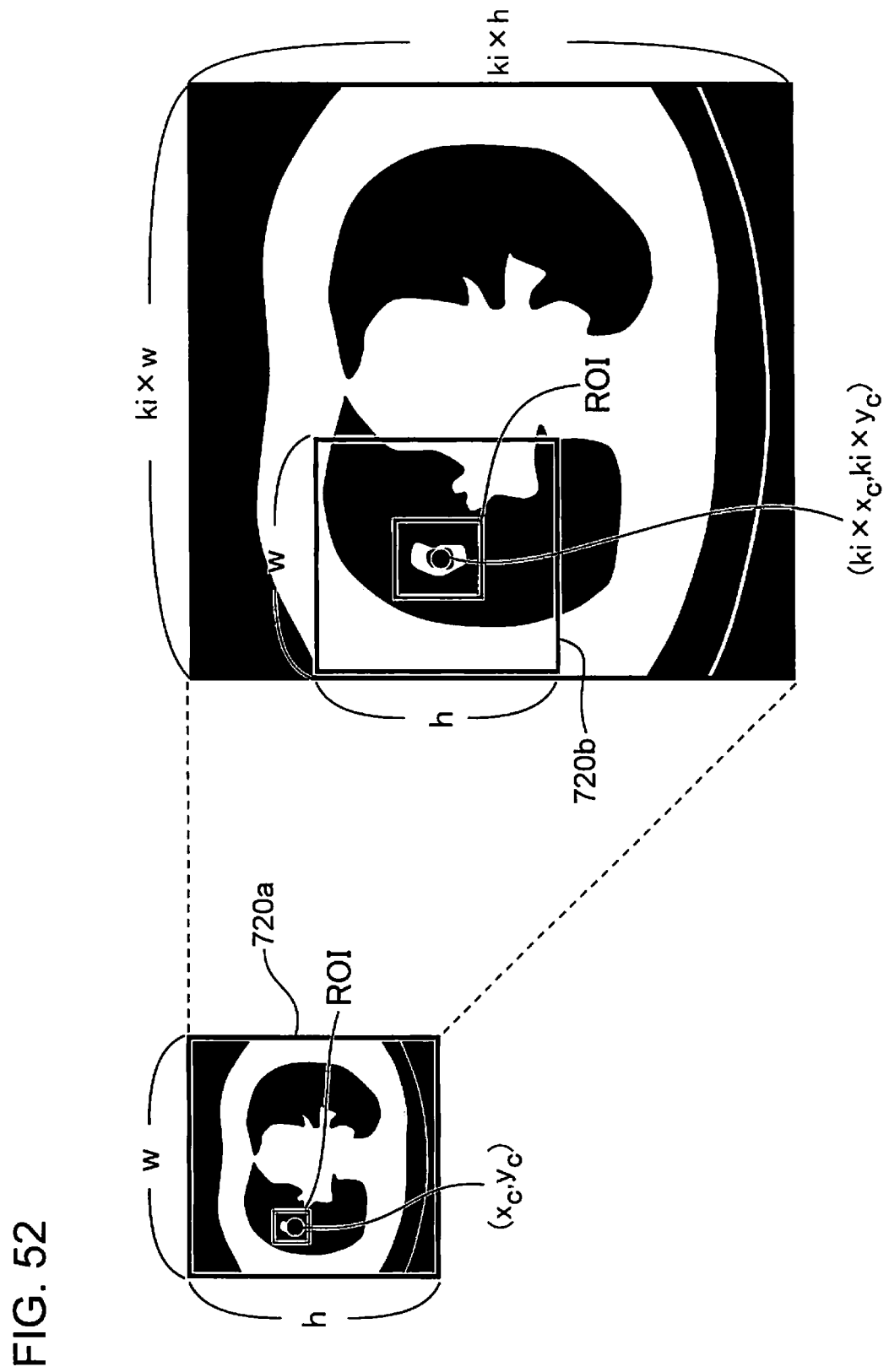
FIG. 52 is a diagram schematically showing a relationship between a magnification ratio and a display region.

FIG. 51 is a flow chart showing a process of the subroutine of S4500 in FIG. 48. FIG. 52 is a diagram schematically showing a relationship between a magnification ratio and a display region. Hereinafter, details of a process for generating a magnified image so that a center position of a region of interest matches a center position of a magnified thumbnail image will be described with reference to FIGS. 51 and 52.

In S4510, the magnified image generating unit 112 generates a magnified image based on the magnification ratio calculated in S4400 and the thumbnail image data 4500 in the similar case data 4000 (FIG. 30). When the magnification ratio is ki, a magnified thumbnail image shown in a right diagram in FIG. 52 is generated from a thumbnail image shown in a left diagram in FIG. 52.

In S4520, the magnified image generating unit 112 calculates center coordinates of a region of interest in the thumbnail image after magnification based on the region of interest information 4300 in the similar case data 4000 (FIG. 30) and the magnification ratio calculated in S4400. In this case, if center coordinates of the region of interest before magnification are denoted by (xc, yc), as shown in FIG. 52, coordinates (ki×xc, ki×yc) that are obtained by multiplying the center coordinates of the region of interest before magnification at the magnification ratio are the center coordinates of the region of interest after the magnification.

In S4530, the magnified image generating unit 112 decides a display region in the thumbnail image i after magnification based on the center coordinates (ki×xc, ki×yc) of the region of interest after the magnification calculated in S4520 and a size of a display region determined in advance. In this case, as shown in the left diagram in FIG. 52, a display region 720a is set to have a horizontal dimension of w and a vertical dimension of h. In this case, a rectangular region 720b shown in the right diagram in FIG. 52 is the display region. Top left coordinates of the rectangular region 720b are (ki×xc−w/2, ki×yc−h/2) and bottom right coordinates of the rectangular region 720b are (ki×xc+w/2, ki×yc+h/2).

In S4540, the display control unit 104 displays, in the display region of the similar case i in the case display region 710, an image in the display region 720b calculated in S4530 among the magnified image generated in S4510 by the magnified image generating unit 112. Due to the process shown in FIG. 51, the magnified thumbnail image i in which a center position of the region of interest matches a center position of the display region can be generated.

According to the process described above, a thumbnail image is displayed at an arbitrary magnification ratio specified by the user in the case display region 710. The magnification ratio of all of the thumbnail images in the case display region 710 can be changed by a magnification operation with respect to one thumbnail image by the user.

Therefore, an operation burden on the user is reduced. In addition, the thumbnail images are displayed in the case display region 710 with uniform sizes of regions of interest. Therefore, an occurrence of a situation where a region of interest is magnified at a low magnification ratio in a part of the similar medical images and the region of interest is overlooked can be prevented and diagnostic accuracy can be improved. Furthermore, a magnification process is only performed on similar cases displayed in the case display region 710 instead of on all of the similar cases obtained by the similar case retrieval. Therefore, a load on the system is significantly reduced.

Next, a flow of a magnification process of a thumbnail image when, after a magnified thumbnail image is displayed in the case display region 710, the user operates the scroll bar 715 will be described. In this case, it is assumed that all of the thumbnail images displayed in the case display region 710 are to be magnified as shown in FIG. 14 or 15.

Figure 53A:
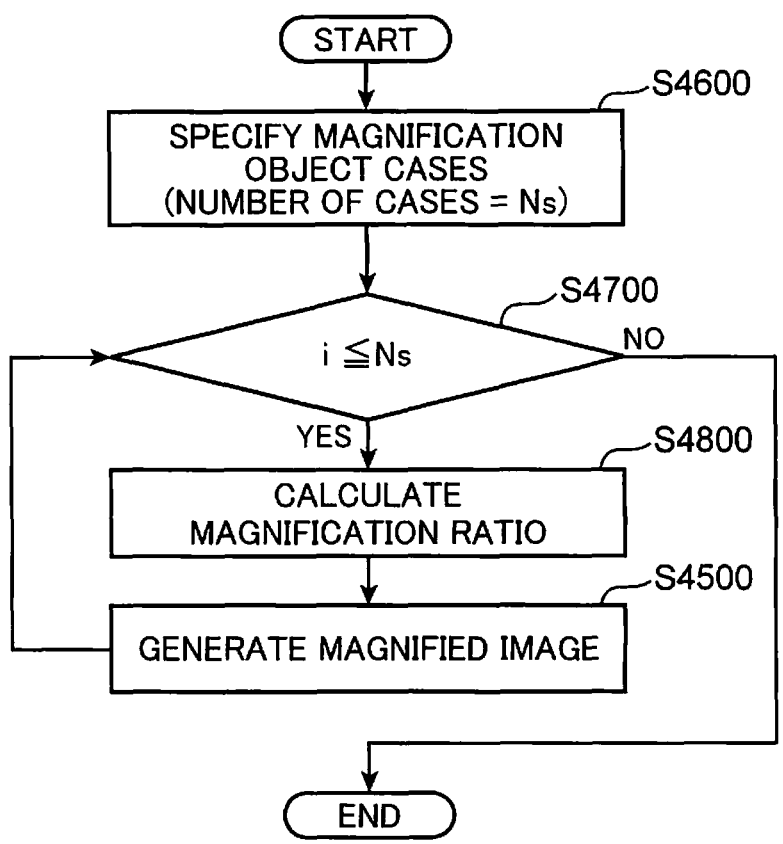
FIG. 53A is a flow chart showing a magnification process of thumbnail images when, after magnified thumbnail images are displayed in a case display region, a user operates a scroll bar.
Figure 53B:
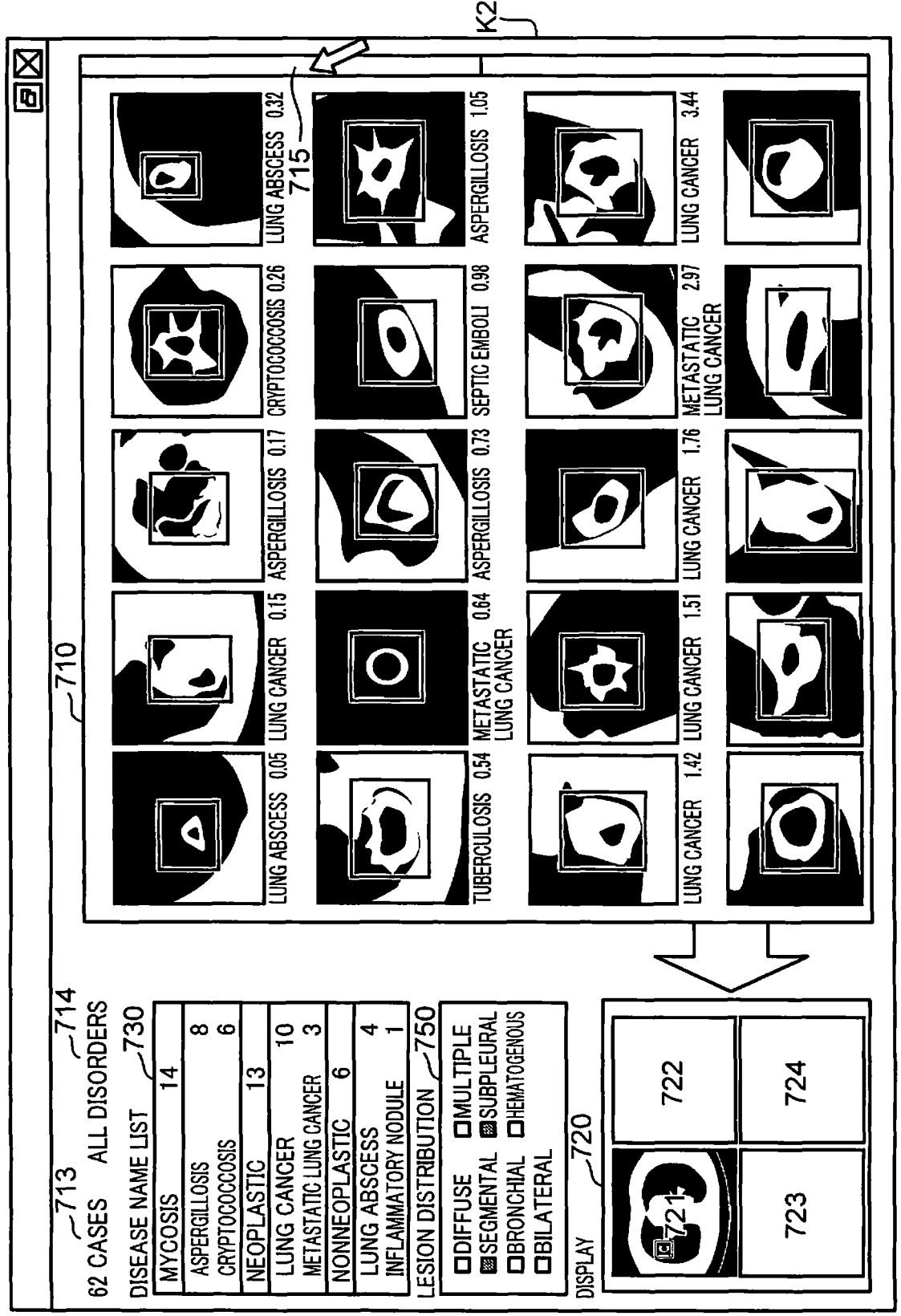
FIG. 53B is a diagram showing a basic screen in a state where magnified thumbnail images are displayed in a case display region.

FIG. 53A is a flow chart showing a magnification process of thumbnail images when, after magnified thumbnail images are displayed in the case display region 710, a user operates the scroll bar 715. FIG. 53B is a diagram showing the basic screen K2 in a state where magnified thumbnail images are displayed in the case display region 710.

When the user operates the scroll bar 715 in a downward direction in a state shown in FIG. 53B, the input control unit 103 senses an operation amount thereof and notifies the magnified image generating unit 112 of the sensed operation amount. As a result, the magnified image generating unit 112 starts the process shown in FIG. 53A.

In S4600, due to the operation of the scroll bar 715 by the user, the magnified image generating unit 112 acquires Ns number of cases to be newly displayed in the case display region 710. Specifically, the magnified image generating unit 112 acquires the maximum number of displayable cases ND determined in advance by the case display region 710 from the display control unit 104. In the present embodiment, as shown in FIG. 6, the maximum number of displayable cases ND is 20 (4 rows by 5 columns). Therefore, since five thumbnail images are to become new display objects, the magnified image generating unit 112 acquires Ns=5.

In addition, in S4600, the magnified image generating unit 112 acquires similar case IDs of the thumbnail images to be newly displayed in the case display region 710. At this point, the magnified image generating unit 112 refers to degrees of similarity of the similar cases received from the similar case retrieving unit 303 of the case retrieval system 300. The display control unit 104 currently displays thumbnail images of ND number of similar cases among similar cases with highest degrees of similarity. Therefore, the magnified image generating unit 112 considers similar cases from a (ND+1)th similar case to a (ND+Ns)th similar case as counted from a similar case with a highest degree of similarity as magnification object cases. The magnified image generating unit 112 specifies the similar case IDs of these magnification objects.

In S4700, the magnified image generating unit 112 decides a thumbnail image of a similar case i (where i is an index specifying a similar case that is a processing object and is an integer not less than 1) as a thumbnail image that is a processing object. Subsequently, the magnified image generating unit 112 repeats the processes of S4800 and S4500 until the index i reaches Ns. The magnified image generating unit 112 increments the index i by 1 each time the processes of S4800 and S4500 are executed. Once the index i exceeds Ns (NO in S4700), the process shown in FIG. 53A is finished.

In S4800, the magnified image generating unit 112 calculates a magnification ratio ki of the similar case i that is the magnification object. Magnified thumbnail images are already displayed in the case display region 710. Therefore, the magnified image generating unit 112 uses the magnification ratio kr for the reference thumbnail image which has been decided in S4100 shown in FIG. 48. In addition, the magnified image generating unit 112 calculates the magnification ratio ki of the similar case i that is the magnification object in a similar manner to S4400 in FIG. 48. Since subsequent S4500 is the same as S4500 in FIG. 48, a detailed description thereof will be omitted. Due to the process shown in FIG. 53A, a screen shown in FIG. 53C is obtained.

Figure 53C:
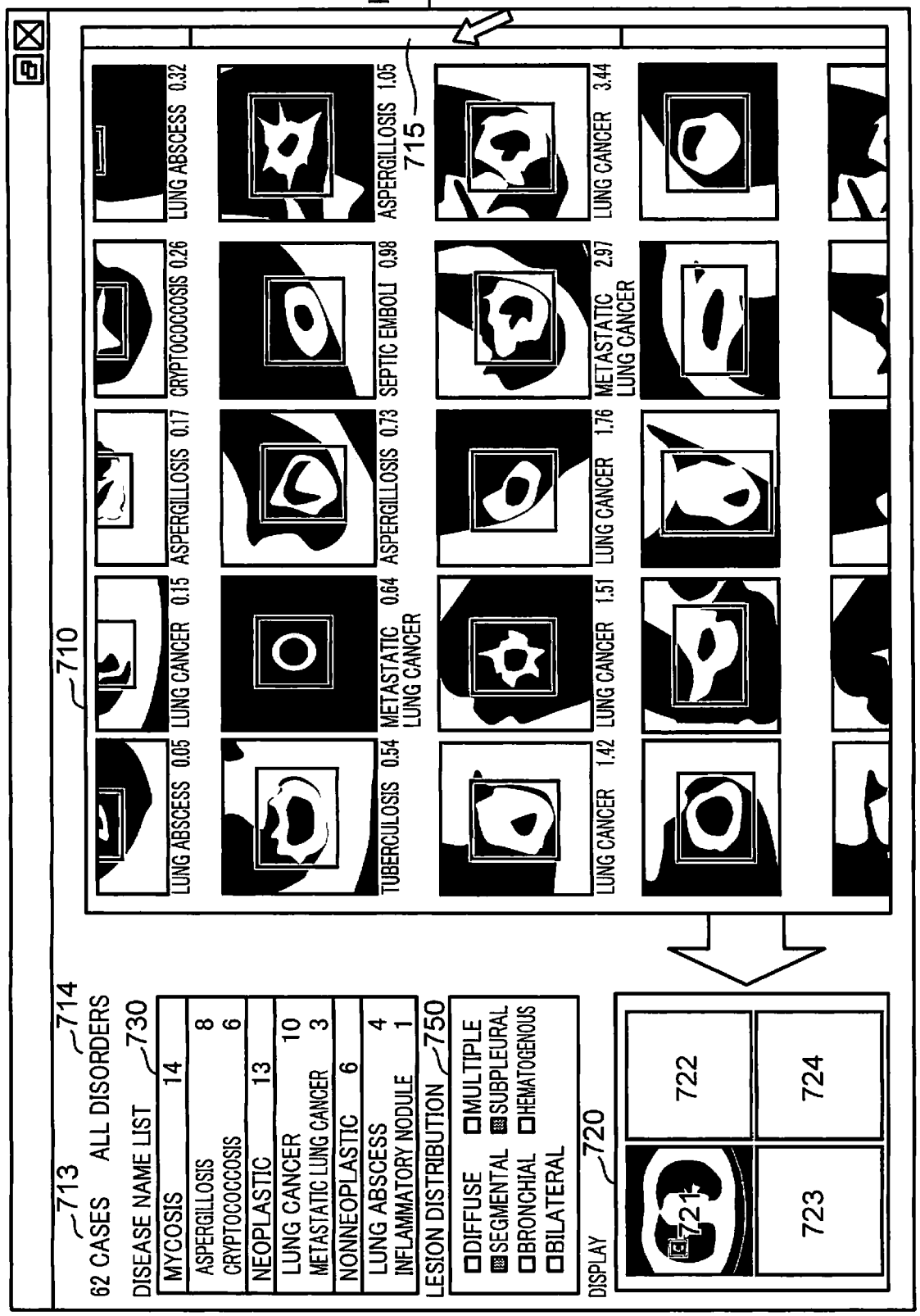
FIG. 53C is a diagram showing a basic screen when magnified thumbnail images have moved from the state shown in FIG. 53B.

FIG. 53C is a diagram showing the basic screen K2 when magnified thumbnail images have moved from the state shown in FIG. 53B. As shown in FIG. 53C, the thumbnail images of the similar cases displayed in the case display region 710 have been moved upward by an operation of the scroll bar 715.

Moreover, when the user continues to operate the scroll bar 715, the magnified image generating unit 112 further executes the process shown in FIG. 53A.

Due to the process described above, even when there are a large number of similar cases, the magnified image generating unit 112 may perform a magnification process only on thumbnail images that are newly displayed in the case display region 710 by an operation of the scroll bar 715. Therefore, a load on the system is significantly reduced.

Figure 54:
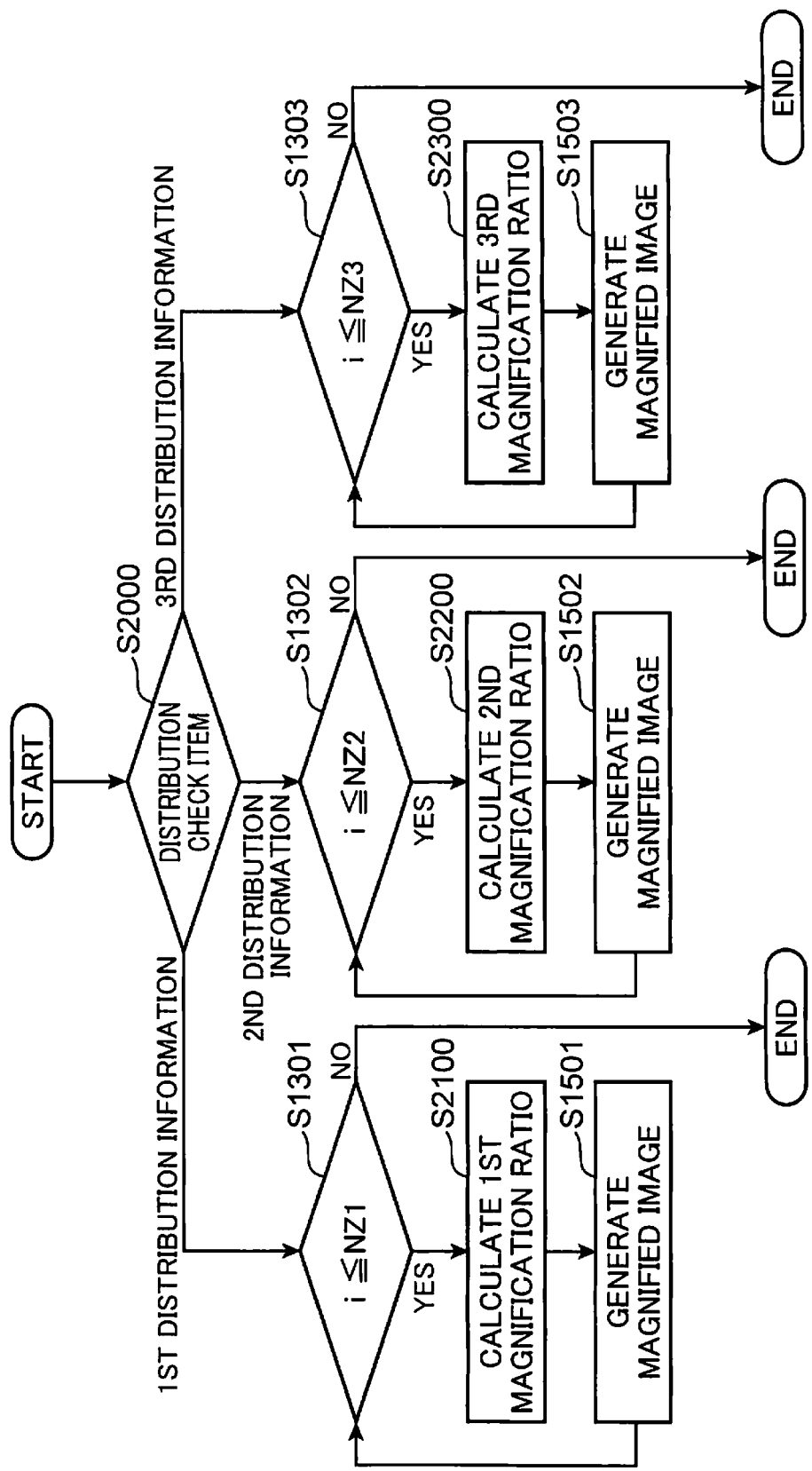
FIG. 54 is a flow chart showing a process when a lesion distribution displayed in a distribution list display region is selected.

Next, a process when a lesion distribution displayed in the distribution list display region 750 shown in FIGS. 20, 22 and 24 is selected will be described. FIG. 54 is a flow chart showing a process when a lesion distribution displayed in the distribution list display region 750 is selected.

In S2000, when the input control unit 103 senses an operation for selecting any one distribution check item among lesion distribution (distribution check items) displayed in the distribution list display region 750, the magnified image generating unit 112 judges which of first to third distribution information the sensed distribution check item corresponds to. In the case of the first distribution information, the process is advanced to S1301, in the case of the second distribution information, the process is advanced to S1302, and in the case of the third distribution information, the process is advanced to S1303.

The first distribution information is information for selecting a thumbnail image, in which a size of a region of interest belongs to a prescribed first range, from among thumbnail images of similar cases that are displayed as a list in the case display region 710. The prescribed first range indicates that the size of the region of interest is larger than a lung region. In this case, "bilateral", "multiple", "diffuse", and "hematogenous" correspond to the first distribution information. Therefore, a value range to which a size of a region of interest, which is set when diagnosing such lesion distribution, belongs is adopted as the first range.

The second distribution information is information for selecting a thumbnail image, in which a size of a region corresponding to a region of interest belongs to a prescribed second range (lower than the first range, that is, an upper limit value of the second range is not more than a lower limit value of the first range), from among thumbnail images of similar cases that are displayed as a list in the case display region 710. The prescribed second range indicates that a size of a region corresponding to a region of interest is a part of a lung region. In this case, "bronchial" and "segmental" correspond to the second distribution information. Therefore, a value range to which a size of a region of interest, which is set when diagnosing such lesion distribution, belongs is adopted as the second range.

The third distribution information is information for selecting a thumbnail image, in which a region of interest exists at a periphery of the pleura, from among thumbnail images of similar cases that are displayed as a list in the case display region 710. In this case, "subpleural" corresponds to the third distribution information.

In S1301, the magnified image generating unit 112 extracts, in a descending order of degrees of similarity, similar cases whose number is not more than a maximum displayable number (20 in the present embodiment) of thumbnail images in the case display region 710 among similar cases which have been obtained as a result of a similar case retrieval and which are similar cases of the lesion distribution selected by the user as the first distribution information, and decides the number of the extracted similar cases as a number NZ1 of similar cases that are magnification objects. In addition, the magnified image generating unit 112 decides that a thumbnail image of an extracted similar case i (i is an index specifying the extracted similar cases and is an integer not less than 1) is a thumbnail image of a processing object. Subsequently, the magnified image generating unit 112 repeats the processes of S2100 and S1501 until the index i reaches NZ1. The magnified image generating unit 112 increments the index i by 1 each time the processes of S2100 and S1501 are executed. Once the index i exceeds NZ1 (NO in S1301), the process of FIG. 54 is finished.

In S2100, the magnified image generating unit 112 calculates a first magnification ratio corresponding to the first distribution information with respect to the similar case i. In this case, as the first magnification ratio, for example, 1.0 is adopted. However, this is simply an example and a magnification ratio other than 1.0 may be adopted as the first magnification ratio as long as the magnification ratio is a value that enables an entire region of interest that is set when diagnosing a lesion distribution representing the first distribution information to fit inside the display region.

In S1501, a process is performed in a similar manner to S4500 in FIG. 48. As a result, the display control unit 104 displays images obtained by magnifying the thumbnail image of the similar case i at the first magnification ratio of the similar case i in the case display region 710.

In FIG. 21 described above, bilateral is selected. In this case, only thumbnail images of similar cases whose lesion distribution corresponds to bilateral among the similar cases are displayed in the case display region 710. In addition, in this case, since the magnification ratio is 1.0, the thumbnail images are displayed in the case display region 710 in a same display mode as the thumbnail images displayed immediately after the similar retrieval result is obtained. In other words, the thumbnail images are displayed without a display position of the thumbnail images being adjusted so that a center of a region of interest ROI is positioned at a center of a display region 6801 and without being magnified.

In S1302, the magnified image generating unit 112 extracts, in a descending order of degrees of similarity, similar cases whose number is not more than a maximum displayable number of thumbnail images in the case display region 710 among similar cases which have been obtained as a result of a similar case retrieval and which are similar cases of the lesion distribution selected by the user as the second distribution information, and decides the number of the extracted similar cases as a number NZ2 of similar cases that are magnification objects. In addition, the magnified image generating unit 112 decides that a thumbnail image of an extracted similar case i is a thumbnail image of a processing object. Subsequently, the magnified image generating unit 112 repeats the processes of S2200 and S1502 until the index i reaches NZ2. The magnified image generating unit 112 increments the index i by 1 each time the processes of S2200 and S1502 are executed. Once the index i exceeds NZ2 (NO in S1302), the process of FIG. 54 is finished.

In S2200, the magnified image generating unit 112 calculates a second magnification ratio corresponding to the second distribution information with respect to the similar case i using a size of a display region determined in advance for one thumbnail image in the case display region 710 and the region of interest information of the similar case i.

When the second distribution information is selected, the magnified image generating unit 112 magnifies the similar case i so that a size of the region of interest is around ½ of a size of the display region. Therefore, the magnified image generating unit 112 calculates a second magnification ratio ki with respect to the similar case i using, for example, the mathematical expression given below. If an area of the display region is denoted by Sd and an area of the region of interest of the thumbnail image of the similar case i that is magnification object is denoted by Si, then the second magnification ratio ki can be calculated by the following equation.

$$ki = 1/2(Sd/Si)$$

In S1502, a process is performed in a similar manner to S4500 in FIG. 48. As a result, the magnified image generating unit 112 magnifies the thumbnail image of the similar case i by the second magnification ratio ki. The display control unit 104 displays thumbnail images magnified by the magnified image generating unit 112 in the case display region 710 so that a center of the region of interest of the thumbnail images is positioned at a center of the display region.

In FIG. 23 described above, bronchial is selected. In this case, only thumbnail images of similar cases whose lesion distribution corresponds to bronchial among the similar cases are displayed in the case display region 710. In addition, in the case display region 710, all thumbnail images have been magnified at the second magnification ratio so that the center of the region of interest ROI is positioned at the center of the display region 6901.

In S1303, the magnified image generating unit 112 extracts, in a descending order of degrees of similarity, similar cases whose number is not more than a maximum displayable number of thumbnail images in the case display region 710 among similar cases which have been obtained as a result of a similar case retrieval and which are similar cases of the lesion distribution selected by the user as the third distribution information. The magnified image generating unit 112 decides the number of the extracted similar cases as a number NZ3 of similar cases that are magnification objects. In addition, the magnified image generating unit 112 decides that a thumbnail image of the extracted similar case i is a thumbnail image of a processing object. Subsequently, the magnified image generating unit 112 repeats the processes of S2300 and S1503 until the index i reaches NZ3. The magnified image generating unit 112 increments the index i by 1 each time the processes of S2300 and S1503 are executed. Once the index i exceeds NZ3 (NO in S1303), the process of FIG. 54 is finished.

In S2300, the magnified image generating unit 112 calculates a third magnification ratio corresponding to the third distribution information with respect to the similar case i using a size of a display region determined in advance for one thumbnail image in the case display region 710, the region of interest information of the similar case i, and pleural region information 4900.

Figure 55:
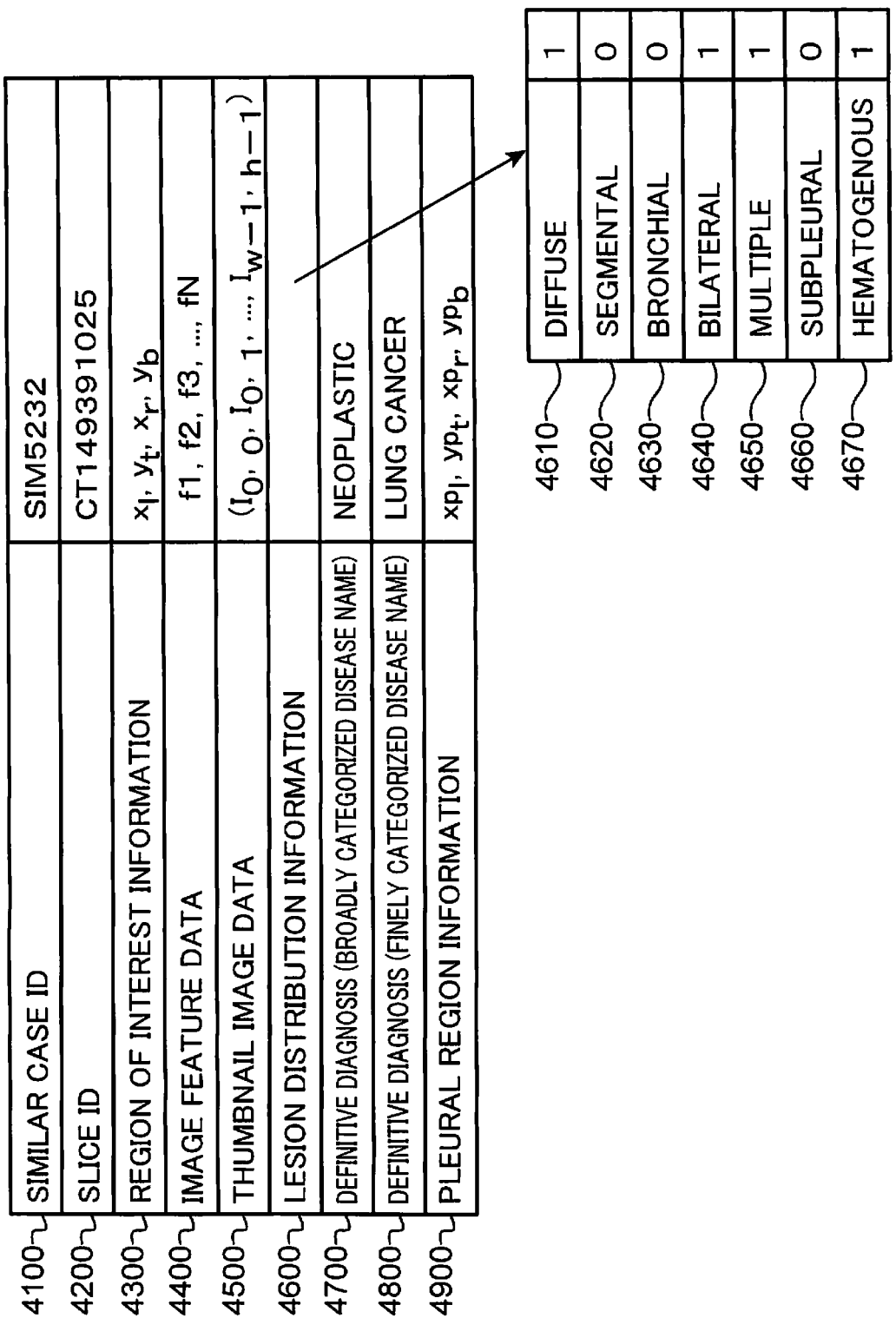
FIG. 55 is a diagram showing a data configuration of similar case data to which pleural region information has been added.

FIG. 55 is a diagram showing a data configuration of similar case data 4000 to which the pleural region information 4900 has been added. Moreover, when the pleural region information 4900 is not registered in the similar case data 4000, the pleural region information 4900 cannot be obtained. In this case, the magnified image generating unit 112 need only set the third magnification ratio to 1.0 which is the same value as the first magnification ratio. The pleural region information 4900 is information indicating a pleural region in a similar case.

In S1503, a process is performed in a similar manner to S4500 in FIG. 48. As a result, the magnified image generating unit 112 magnifies the thumbnail image of the similar case i by the third magnification ratio ki. The display control unit 104 displays thumbnail images magnified by the magnified image generating unit 112 in the case display region 710 so that a center of the region of interest of the thumbnail images is positioned at a center of the display region.

Figure 56:
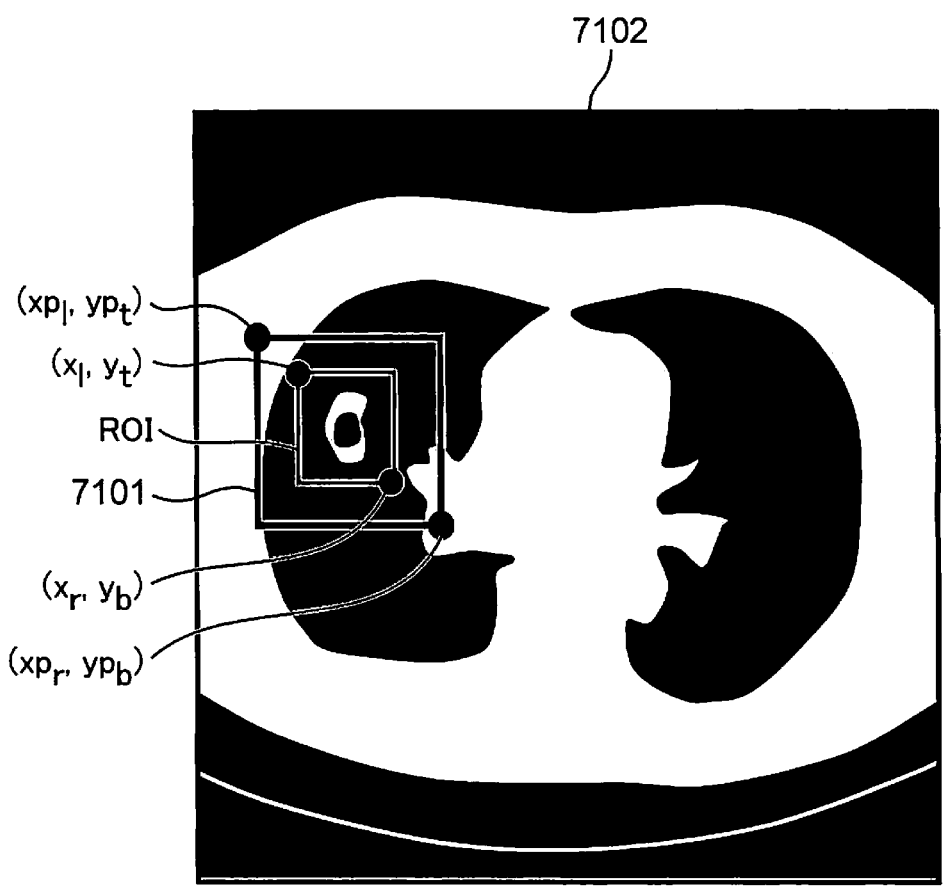
FIG. 56 is a diagram for describing a pleural region.

FIG. 56 is a diagram for describing a pleural region 7101. As shown in FIG. 56, the pleural region 7101 is a region which includes a pleura, whose center is positioned at a center of the region of interest ROI, and which has a rectangular shape slightly larger in size than the region of interest ROI. In this case, the pleural region information 4900 is constituted by four values including coordinates (xpl, ypt) of a top left vertex and coordinates (xrp, ypb) of a bottom right vertex of the pleural region 7101. When the third distribution information is selected, in order to display a magnified pleural region, the magnified image generating unit 112 calculates the third magnification ratio ki using the mathematical expression given below. If an area of the display region 7102 is denoted by Sd and an area of the pleural region 7101 is denoted by Sp, then the third magnification ratio ki can be calculated by the following equation.

$$ki = Sd/Sp$$

Moreover, the pleural region information 4900 may be input by the user together with region of interest information when creating the similar case data 4000. Alternatively, the pleural region information 4900 may be automatically created by having an image processing apparatus automatically extract a lung region from a slice image and judge a pleural position.

In FIG. 25 described above, subpleural is selected. In this case, only thumbnail images of similar cases whose lesion distribution corresponds to subpleural among the similar cases are displayed in the case display region 710. In addition, in the case display region 710, all thumbnail images have been magnified at the third magnification ratio so that the center of the region of interest ROI is positioned at the center of the display region 7001.

According to the process described above, thumbnail images are displayed in the case display region 710 at a magnification ratio that reflects contents of diagnosis with respect to lesion distribution. In addition, the thumbnail images are displayed in the case display region 710 while making sizes of regions of interest uniform. Therefore, an occurrence of a situation where a region of interest is magnified at a low magnification ratio in a part of the similar medical images and the region of interest is overlooked can be prevented and diagnostic accuracy can be improved. Furthermore, since the magnification process is only performed on the similar cases displayed in the case display region 710 instead of on all of the similar cases obtained by similar case retrieval, a load on the system can be significantly reduced.

Second Embodiment

In the first embodiment described above, a magnification ratio of thumbnail images of similar cases is controlled in accordance with an operation amount of the user with respect to the operating unit 102. In comparison, in the second embodiment, a magnification ratio is controlled based on an operation by the user with respect to a magnification ratio change button that is provided on a basic screen.

Figure 57:
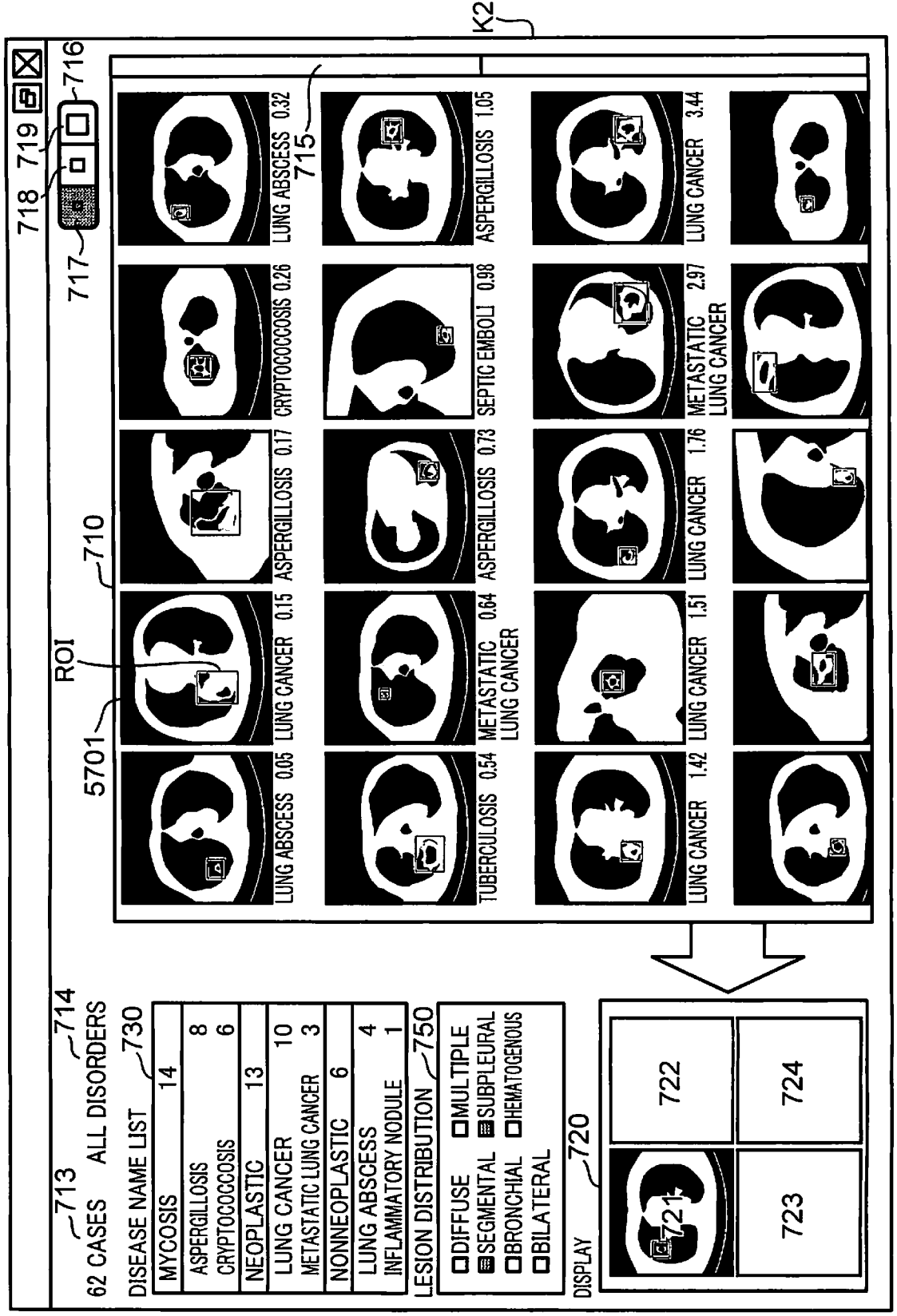
FIG. 57 is a diagram showing a basic screen in a state where thumbnail images of similar cases retrieved by similar case retrieval are displayed in a case display region according to a second embodiment.

FIG. 57 is a diagram showing the basic screen K2 in a state where thumbnail images of similar cases retrieved by similar case retrieval are displayed in the case display region 710 according to the second embodiment. The following description will focus on portions that differ from the first embodiment described above.

In the second embodiment, the basic screen K2 includes a magnification ratio change button 716 (an example of the one or more instruction buttons). As shown in FIG. 57, as the magnification ratio change button 716, the basic screen K2 includes a first instruction button 717, a second instruction button 718, and a third instruction button 719.

In the second embodiment, when the user selects any of the first instruction button 717, the second instruction button 718, and the third instruction button 719 which are included in the magnification ratio change button 716, the selection is sensed by the input control unit 103. Accordingly, the input control unit 103 notifies the magnified image generating unit 112 of information on the button selected by the user. In accordance with the notified button information, the magnified image generating unit 112 changes a magnification ratio of all of the thumbnail images displayed in the case display region 710.

When the first instruction button 717 is selected by the user, the magnified image generating unit 112 calculates a magnification ratio of 1.0. Moreover, the initial basic screen K2 after the similar case retrieval is in a state where the first instruction button 717 has been selected. Therefore, the magnification ratio of the thumbnail images on the basic screen K2 shown in FIG. 57 is 1.0. In addition, in FIG. 57, the display control unit 104 has changed the color of the first instruction button 717.

Figure 58:
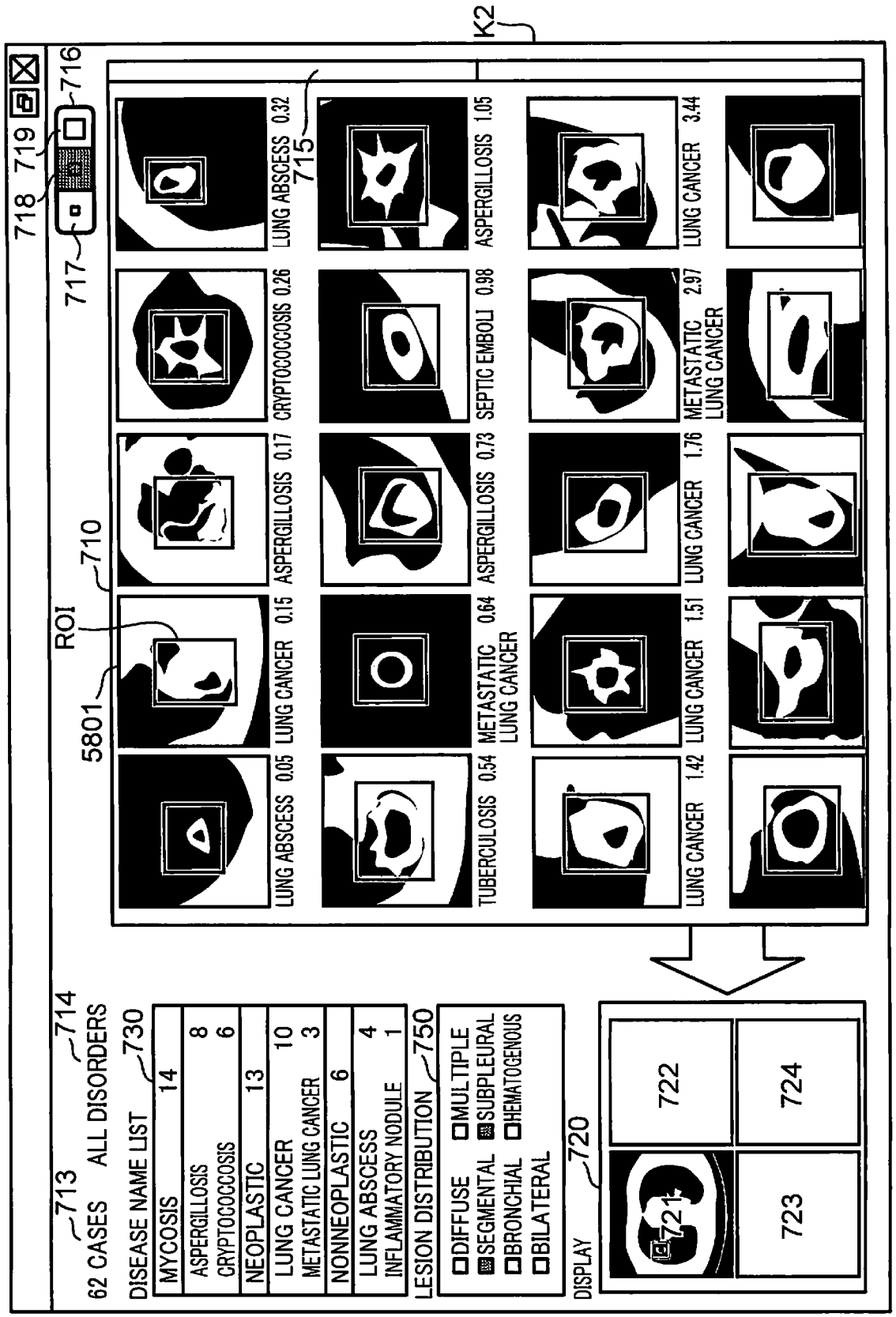
FIG. 58 is a diagram showing a basic screen in a case where a second instruction button is selected by a user.
Figure 59:
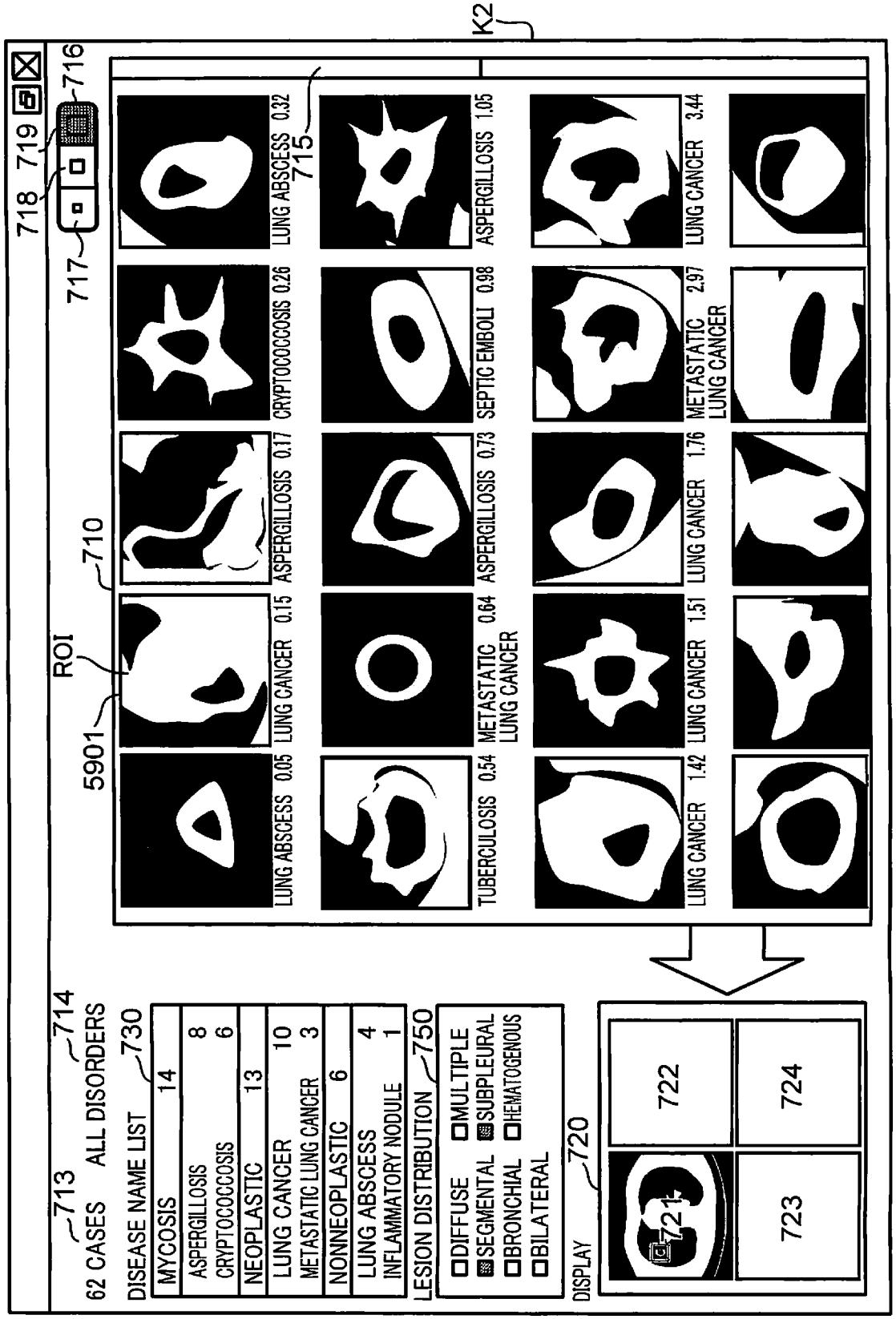
FIG. 59 is a diagram showing a basic screen in a case where a third instruction button is selected by a user.

FIG. 58 is a diagram showing the basic screen K2 in a case where the second instruction button 718 has been selected by the user. FIG. 59 is a diagram showing the basic screen K2 in a case where the third instruction button 719 has been selected by the user.

In FIG. 58, the display control unit 104 has changed the color of the second instruction button 718. In addition, in FIG. 59, the display control unit 104 has changed the color of the third instruction button 719.

When the second instruction button 718 is selected by the user on the basic screen K2 shown in FIG. 57 or 59, the magnified image generating unit 112 calculates the magnification ratio of each thumbnail image so that a size of the region of interest ROI is magnified to around ½ of a size of a display region 5801 as shown in FIG. 58.

When the third instruction button 719 is selected by the user on the basic screen K2 shown in FIG. 57 or 58, the magnified image generating unit 112 calculates the magnification ratio of each thumbnail image so that a size of the region of interest ROI is magnified to around a same size as a display region 5901 as shown in FIG. 59.

In FIGS. 58 and 59, thumbnail images of M number (M =20 in FIGS. 58 and 59) of similar cases are displayed in the case display region 710 that is capable of displaying a maximum number ND of cases (ND=20 in the present embodiment), and M number (20 in FIGS. 58 and 59) of thumbnail images are magnified. As shown, in the second embodiment, all of the thumbnail images displayed in the case display region 710 are magnified. For example, when M=14 as in the case of FIG. 17, all of the 14 thumbnail images are to be magnified.

Next, a magnification process when the user selects the magnification ratio change button 716 will be described.

Figure 60:
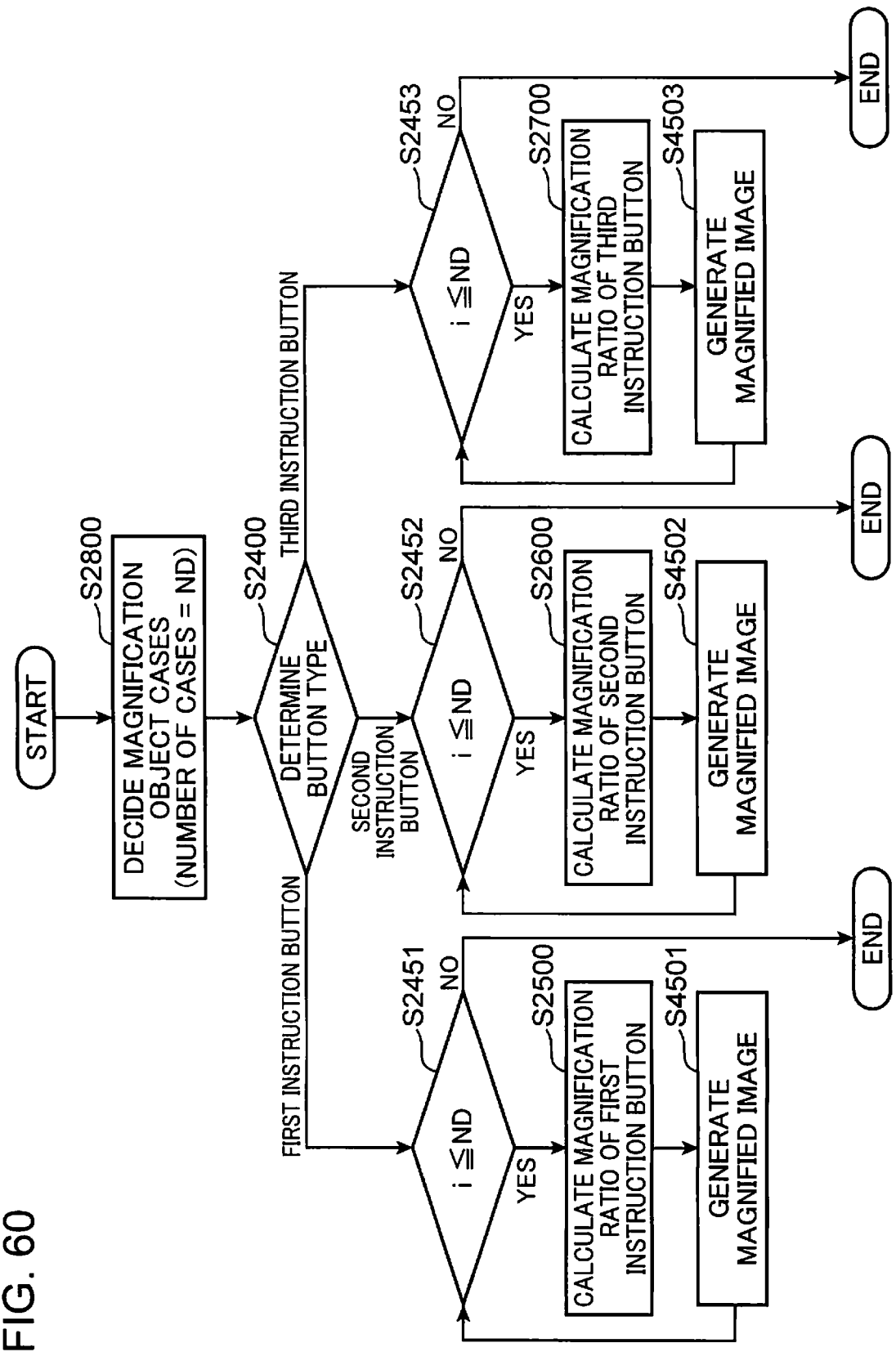
FIG. 60 is a flow chart showing a magnification process when a user selects a magnification ratio change button.

FIG. 60 is a flow chart showing a magnification process when the user selects the magnification ratio change button 716.

In S2800, the magnified image generating unit 112 decides an object on which a magnification process is to be performed among a large number of similar cases acquired by the similar case retrieval.

In the second embodiment, selection of a thumbnail image of a similar case to serve as a reference as in S4100 shown in FIG. 48 according to the first embodiment is not performed by the user, and only a selection of the magnification ratio change button 716 is performed by the user. Therefore, the magnified image generating unit 112 sets all of the similar cases displayed in the case display region 710 upon selection of the magnification ratio change button 716 by the user as objects on which the magnification process is to be performed. To this end, the magnified image generating unit 112 acquires similar case IDs of all of the thumbnail images displayed in the case display region 710 from the similar case data 4000 (FIG. 30).

In S2400, the magnified image generating unit 112 determines a type of a button selected by the user based on button information notified by the input control unit 103. When a button type selected by the user is the first instruction button 717, the process advances to S2451, when the selected button type is the second instruction button 718, the process advances to S2452, and when the selected button type is the third instruction button 719, the process advances to S2543.

In S2451, the magnified image generating unit 112 decides a thumbnail image of a similar case i (where i is an index specifying a similar case that is a processing object and is an integer not less than 1) as a thumbnail image that is a processing object. Subsequently, the magnified image generating unit 112 repeats the processes of S2500 and S4501 until the index i reaches ND. The magnified image generating unit 112 increments the index i by 1 each time the processes of S2500 and S4501 are executed. Once the index i exceeds ND (NO in S2451), the process shown in FIG. 60 is finished.

In S2500, the first instruction button 717 has been selected by the user. Therefore, in S2500, the magnified image generating unit 112 calculates the magnification ratio to be 1.0.

In S4501, a process is performed in a similar manner to S4500 in FIG. 48. As a result, since the magnification ratio is 1.0, as shown in FIG. 57, the display control unit 104 displays the thumbnail images in the case display region 710 in a same display mode as the thumbnail images displayed immediately after the similar retrieval result is obtained.

In S2452, the magnified image generating unit 112 decides a thumbnail image of a similar case i (where i is an index specifying a similar case that is a processing object and is an integer not less than 1) as a thumbnail image that is a processing object. Subsequently, the magnified image generating unit 112 repeats the processes of S2600 and S4502 until the index i reaches ND. The magnified image generating unit 112 increments the index i by 1 each time the processes of S2600 and S4502 are executed. Once the index i exceeds ND (NO in S2452), the process shown in FIG. 60 is finished.

In S2600, the second instruction button 718 has been selected by the user. Therefore, in S2600, as described earlier, the magnified image generating unit 112 calculates the magnification ratio of the thumbnail image i that is the processing object to cause a size of a region of interest to be around 1/2 of a size of the display region. The magnified image generating unit 112 calculates the magnification ratio based on the size of the display region and the region of interest information 4300 in the similar case data 4000 (FIG. 30) of the thumbnail image i that is the processing object. The magnified image generating unit 112 calculates a magnification ratio ki using an equation such as that provided below. If an area of a display region 5701 (FIG. 57) is denoted by Sd and an area of a region of interest ROI (FIG. 57) of the thumbnail image i that is the processing object is denoted by Si, then the magnification ratio ki of the thumbnail image of the similar case i that is the processing object can be calculated using the following equation.

$$ki=1/2(Sd/Si)$$

In S4502, a process is performed in a similar manner to S4500 in FIG. 48. As a result, the magnified image generating unit 112 magnifies the thumbnail images so that a center of the region of interest of the thumbnail image of the similar case i is positioned at a center of the display region. The display control unit 104 displays the magnified thumbnail images generated by the magnified image generating unit 112 in the case display region 710.

Moreover, in this second embodiment, the magnified image generating unit 112 calculates a magnification ratio when the second instruction button 718 is selected so that a ratio of a size of the region of interest to a size of the display region is around ½. However, in the present disclosure, the ratio is not limited to ½. For example, another value such as ⅓ and ⅔ may be adopted as the ratio.

In S2453, the magnified image generating unit 112 decides a thumbnail image of a similar case i (where i is an index specifying a similar case that is a processing object and is an integer not less than 1) as a thumbnail image that is a processing object. Subsequently, the magnified image generating unit 112 repeats the processes of S2700 and S4503 until the index i reaches ND. The magnified image generating unit 112 increments the index i by 1 each time the processes of S2700 and S4503 are executed. Once the index i exceeds ND (NO in S2453), the process shown in FIG. 60 is finished.

In S2700, the third instruction button 719 has been selected by the user. Therefore, in S2700, as described earlier, the magnified image generating unit 112 calculates the magnification ratio of the thumbnail image i that is the processing object so that a size of the region of interest is approximately the same as a size of the display region. The magnified image generating unit 112 calculates the magnification ratio based on the size of the display region and the region of interest information 4300 in the similar case data 4000 (FIG. 30) of the similar case i that is the processing object. The magnified image generating unit 112 calculates a magnification ratio ki using an equation such as that provided below. If an area of the display region 5701 (FIG. 57) is denoted by Sd and an area of the region of interest ROI (FIG. 57) of the thumbnail image of the similar case i that is the processing object is denoted by Si, then the magnification ratio ki of the thumbnail image of the similar case i that is the processing object can be calculated using the following equation.

$$ki=Sd/Si$$

In S4503, a process is performed in a similar manner to S4500 in FIG. 48. As a result, the magnified image generating unit 112 magnifies the thumbnail images so that a center of the region of interest of the thumbnail image of the similar case i is positioned at a center of the display region. The display control unit 104 displays the magnified thumbnail images generated by the magnified image generating unit 112 in the case display region 710.

Moreover, in this second embodiment, the magnified image generating unit 112 calculates a magnification ratio when the third instruction button 719 is selected so that a ratio of a size of the region of interest to a size of the display region is around 1.0. However, in the present disclosure, the ratio is not limited to 1.0. For example, another value such as 1.1 and 0.9 may be adopted as the ratio.

According to the process described above, in the case display region 710, sizes of the region of interest ROI in each of the display regions can be made uniform. As a result, an occurrence of a situation where the region of interest is magnified at a low magnification ratio in a part of the similar medical images and the region of interest is overlooked can be prevented and diagnostic accuracy can be improved. In this case, a magnification process is only performed on similar cases displayed in the case display region 710 instead of on all of the similar cases obtained by the similar case retrieval. Therefore, a load on the system is significantly reduced.

Examples of executing a change process of a magnification ratio of thumbnail images on the information terminal 100 have been described above. Alternatively, a change process of a magnification ratio using the magnification ratio change button 716 according to the second embodiment may be executed by the case retrieval system 300. In this case, the case retrieval system 300 may generate thumbnail images at a changed magnification ratio in advance. Subsequently, when the magnification ratio change button is operated, the thumbnail images may be transmitted from the case retrieval system 300 to the information terminal 100.

Figure 61:
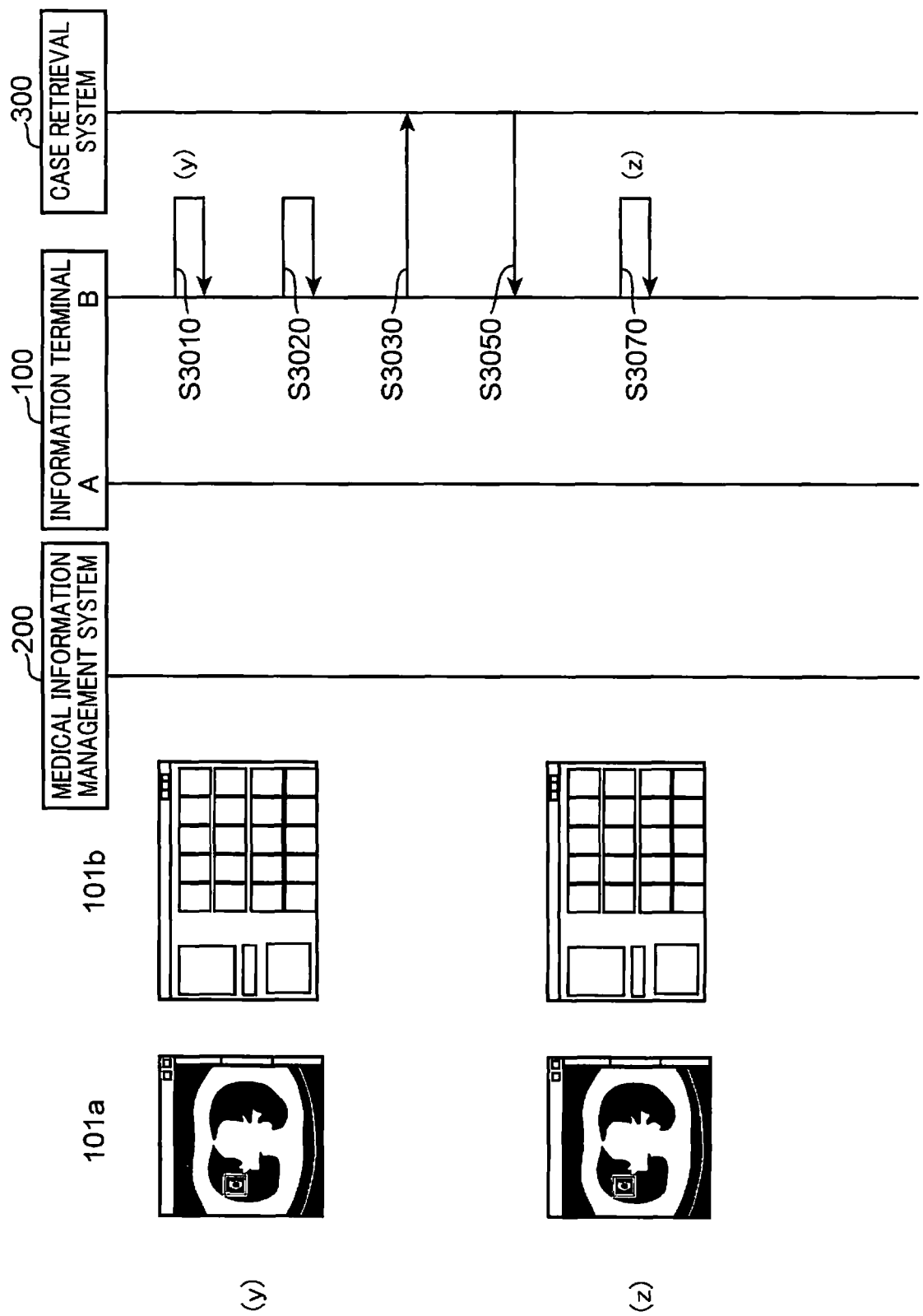
FIG. 61 is a sequence diagram showing a process from a selection of a magnification ratio change button in an information terminal to display of magnified thumbnail images on a display of the information terminal, after a case retrieval system transmits a similar case retrieval result to the information terminal.
Figure 62:
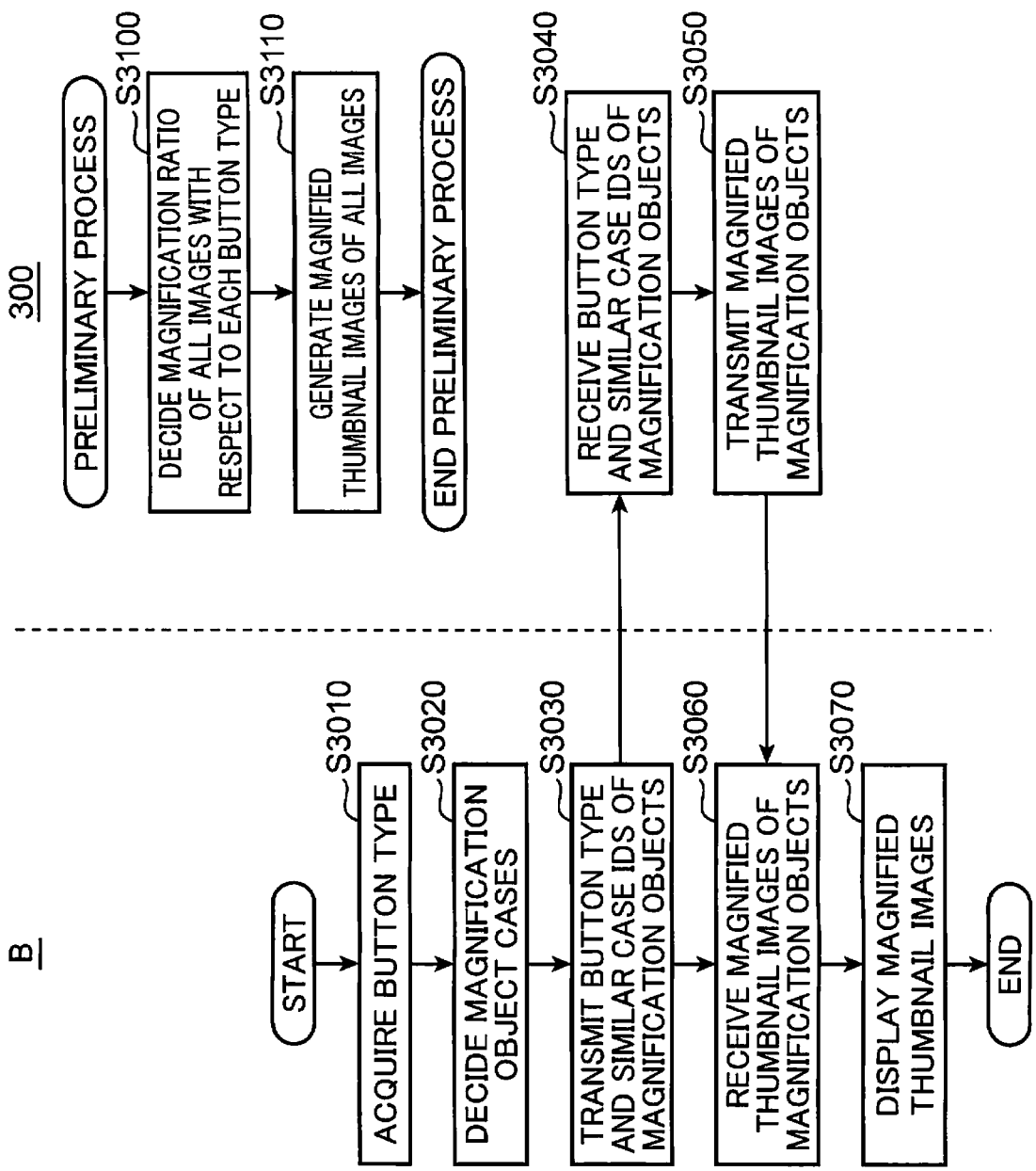
FIG. 62 is a flow chart showing a preliminary process that is executed by a case retrieval system and the process shown in FIG. 61.

FIG. 61 is a sequence diagram showing a process from a selection of the magnification ratio change button 716 in the information terminal 100 to display of magnified thumbnail images on the display 101b of the information terminal 100, after the case retrieval system 300 transmits a similar case retrieval result to the information terminal 100. FIG. 62 is a flow chart showing a preliminary process that is executed by the case retrieval system 300 and the process shown in FIG. 61. In FIG. 62, processes similar to those shown in FIG. 61 are denoted by the same reference characters. A detail of the process will now be described with reference to FIGS. 61 and 62.

First, a preliminary process that is executed by the case retrieval system 300 will be described. In S3100 shown in FIG. 62, the case retrieval system 300 decides a magnification ratio of each of the thumbnail images with respect to each of the first instruction button 717, the second instruction button 718, and the third instruction button 719 of the magnification ratio change button 716. Moreover, as procedures for deciding the magnification ratios, the procedures described with respect to S2500, S2600, and S2700 in FIG. 60 described above may be used.

In S3110, the case retrieval system 300 respectively generates magnified thumbnail image data with respect to the first instruction button 717, the second instruction button 718, and the third instruction button 719 based on the magnification ratio decided in S3100 and the thumbnail image data 4500 in the similar case data 4000 (FIG. 30). As shown in FIG. 63, the case retrieval system 300 stores the generated magnified thumbnail image data as magnified thumbnail data 5000 in the similar case data accumulating unit 301 separately from the similar case data 4000 (FIG. 30).

FIG. 63 is a diagram showing a data configuration of the magnified thumbnail data 5000. The magnified thumbnail data 5000 is data for saving the magnified thumbnail image data in the similar case data accumulating unit 301. As shown in FIG. 63, the magnified thumbnail data 5000 includes, in association with a similar case ID 5100, magnified thumbnail image data 5200 that corresponds to the first instruction button 717, magnified thumbnail image data 5300 that corresponds to the second instruction button 718, and magnified thumbnail image data 5400 that corresponds to the third instruction button 719.

Next, a process in a case where the magnification ratio change button is selected by the user on the information terminal 100 will be described with reference to FIGS. 61 and 62.

In S3010, the input control unit 103 senses a type of an instruction button when the user selects the magnification ratio change button 716. In other words, the input control unit 103 senses which of the first instruction button 717, the second instruction button 718, and the third instruction button 719 is selected by the user.

In S3020, the display control unit 104 acquires similar case IDs of ND number (ND=20 in the present embodiment) of similar cases that are displayed in the case display region 710 upon the selection of the magnification ratio change button 716 by the user from the similar case data 4000 (FIG. 30). In addition, the display control unit 104 decides the acquired similar case IDs as similar cases that are magnification objects.

In S3030, the communication control unit 110 transmits the type of the magnification ratio change button 716 that is sensed by the input control unit 103 in S3010 and the (ND number of) similar case IDs that are magnification objects acquired by the display control unit 104 in S3020 to the case retrieval system 300.

In S3040, the communication control unit 304 of the case retrieval system 300 receives the type of the magnification ratio change button 716 and the (ND number of) similar case IDs that are magnification objects transmitted by the information terminal 100 in S3030.

In S3050, based on the received similar case IDs and the type of the magnification ratio change button 716, the case retrieval system 300 specifies image data to be used for display among the magnified thumbnail image data 5200, 5300, and 5400 in the magnified thumbnail data 5000. The communication control unit 304 of the case retrieval system 300 transmits the specified magnified thumbnail image data to the information terminal 100.

In S3060, the communication control unit 110 of the information terminal 100 receives the magnified thumbnail image data transmitted by the case retrieval system 300.

In S3070, based on the magnified thumbnail image data received by the communication control unit 110 in S3060, the display control unit 104 of the information terminal 100 displays magnified thumbnail images of the similar cases in the case display region 710 on the display 101b of the information terminal 100.

(Supplementary Description to Embodiment 1)

Next, processes by the information terminal 100, the medical information management system 200, and the case retrieval system 300 when focusing on the sequence diagrams shown in FIGS. 32 and 36A on an application level will be described.

Figure 64:
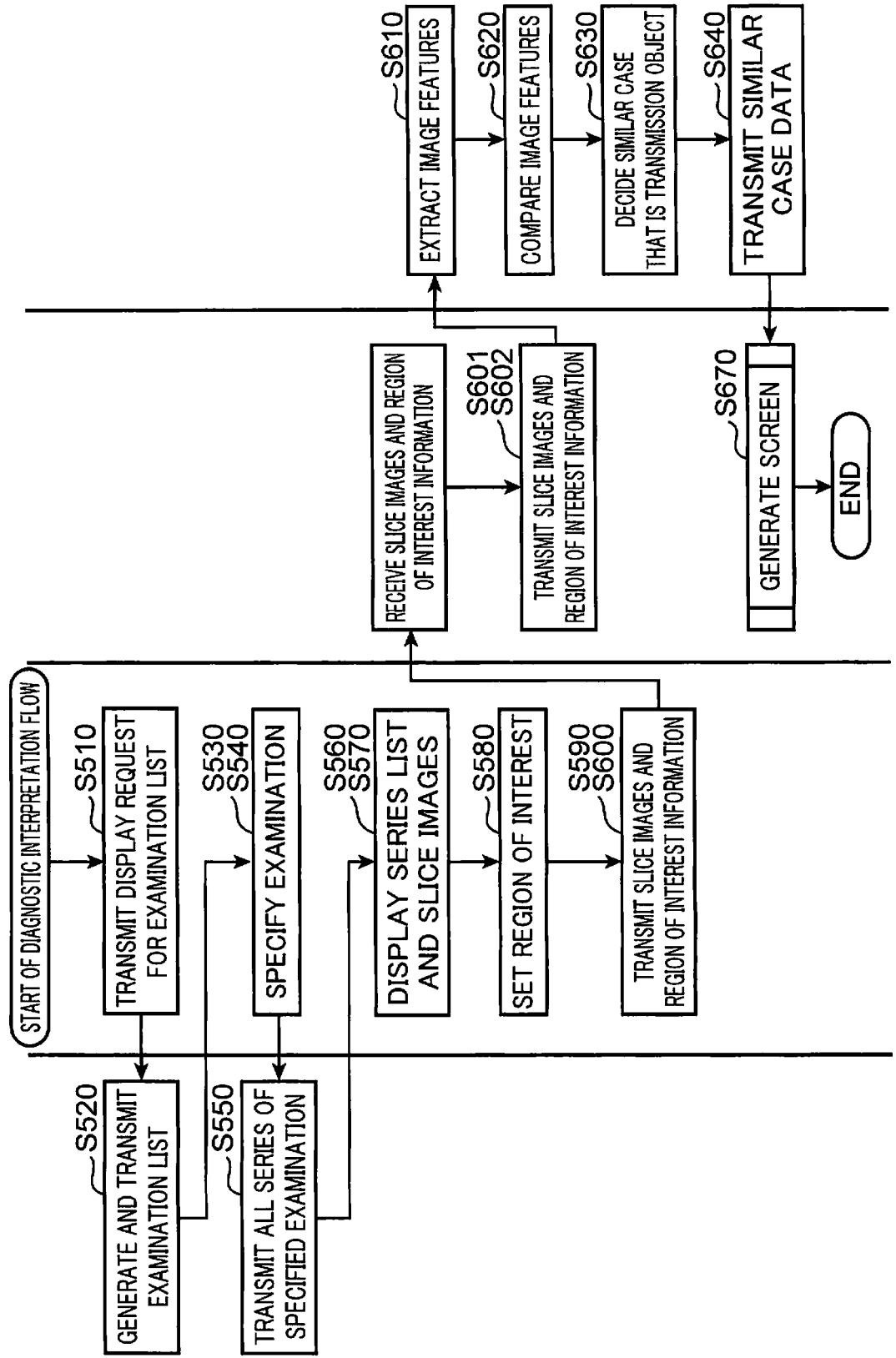
FIG. 64 is a sequence diagram when focusing on the sequence diagrams shown in FIGS. 32 and 36A on an application level.

FIG. 64 is a sequence diagram when focusing on the sequence diagrams shown in FIGS. 32 and 36A on an application level. In FIG. 64, same processes as in FIG. 32 are assigned same reference characters.

Figure 65:
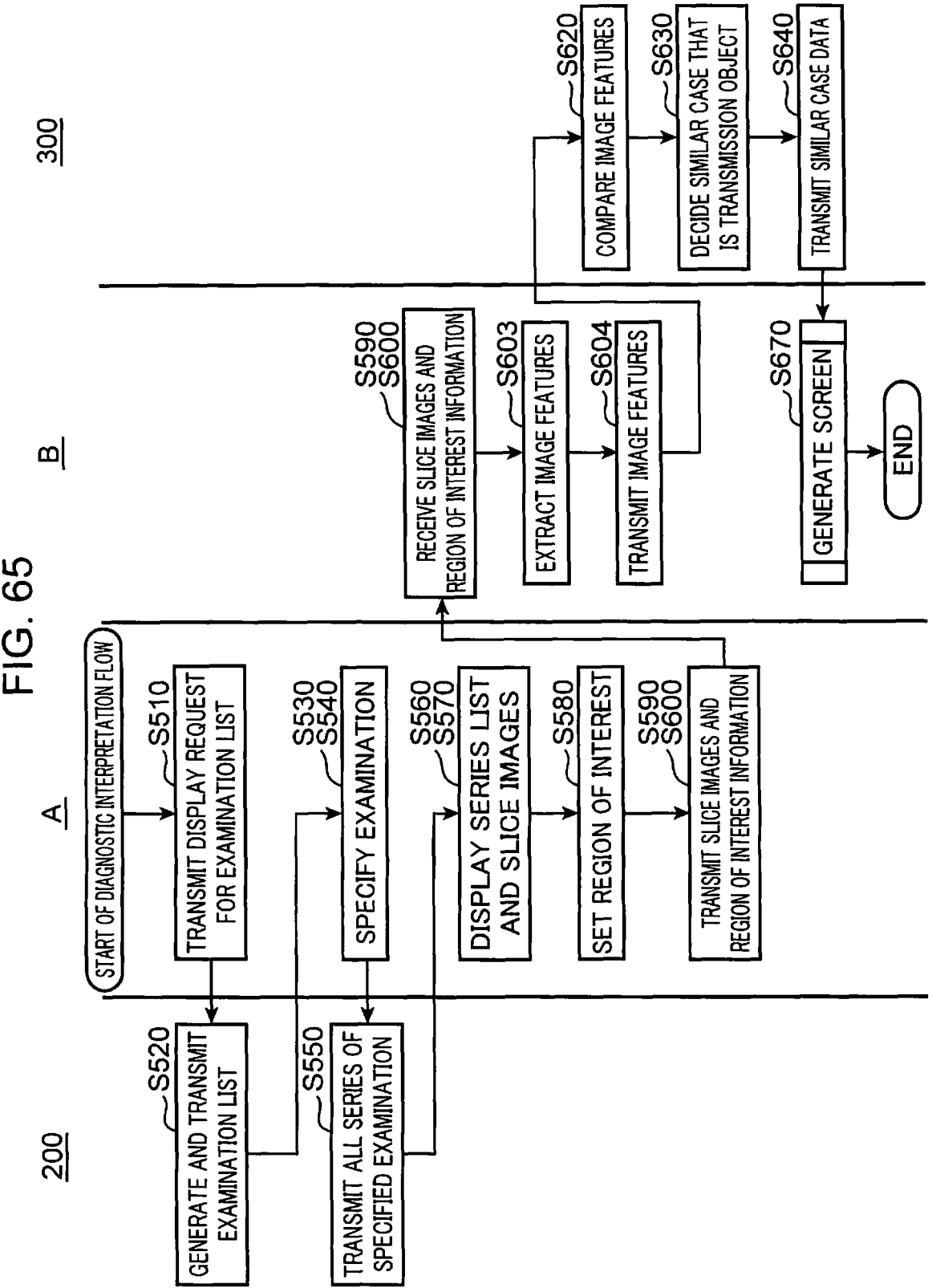
FIG. 65 is a sequence diagram which focuses, on an application level, on a process when a thumbnail image of a similar case is dragged-and-dropped in an information terminal.

In FIGS. 64 and 65, "A" denotes a process of the medical information management application executed by the information terminal 100 and "B" denotes a process of the similar case retrieval application executed by the information terminal 100. Hereinafter, the medical information management application will be described as "application A" and the similar case retrieval application will be described as "application B".

First, the application A accepts a display request for a list of examinations to be diagnostic interpretation objects from a user, and transmits the display request to the medical information management system 200 (S510). Upon receiving the display request of the examination list, the medical information management system 200 lists examinations for which image-based examination has been performed but diagnostic interpretation has not been completed, generates a list of examinations to be diagnostic interpretation objects, and transmits the examination list to the application A.

Upon receiving the examination list, as shown in FIG. 33, the application A displays the examination list on the display 101, and when one examination is selected by the user from the examination list (S530), the application A transmits a display request for the selected examination to the medical information management system 200 (S540).

The medical information management system 200 having received the examination request transmits all slice images of all series included in the examination ID specified by the display request to the application A (S550).

Next, as shown in FIG. 34, the application A displays a series list that displays a list of information related to all series included in the specified examination ID (S560).

Subsequently, when a series that is a diagnostic interpretation object is selected by the user from the series list, the application A displays a slice image at a first slice position of the selected series on the medical image viewer 610 (S570). At this point, the user inputs an operation for slice feeding and causes a desired slice image to be displayed on the medical image viewer 610.

Next, the application A accepts an operation for setting a region of interest in the slice image displayed on the medical image viewer 610 from the user (S580).

Subsequently, the application A generates region of interest information representing the region of interest set by the user and transmits the region of interest information together with a slice image (slice image of the diagnosis object case) in which the region of interest is set to the application B (S590, S600).

Next, upon receiving the slice image and the region of interest information of the diagnosis object case, the application B transmits the slice image and the region of interest information to the case retrieval system 300 (S601, S602).

Upon receiving the slice image and the region of interest information, the case retrieval system 300 executes the processes of S610 to S640 in a similar manner to FIG. 32.

Subsequently, the application B generates an initial basic screen using the similar case data transmitted in S640 and the display box management information 4410 (S670). In addition, the application B executes the process of S670 that is shown in detail in FIG. 33.

FIG. 65 is a sequence diagram which focuses, on an application level, on a process when a thumbnail image of a similar case is dragged-and-dropped in the information terminal 100.

S603 and S604 are not included in FIG. 64 while these steps are included in FIG. 65. In FIG. 65, an image feature is extracted by the information terminal 100. Therefore, the application B extracts an image feature from a region of interest set in the slice image of the diagnosis object case (S603) and transmits the extracted image feature to the case retrieval system 300 (S604).

INDUSTRIAL APPLICABILITY

The present disclosure can be used in a similar case retrieval apparatus for presenting similar cases to be used as a reference when diagnosing a medical image that is a diagnostic interpretation object, a diagnostic interpretation teaching apparatus for diagnostic interpretation interns, and the like.

What is claimed is:

1. A control method for an information terminal, the information terminal including a display and being connected to a case retrieval system, the control method comprising:

displaying, on the display, an object medical image which is a medical image of a diagnostic interpretation object;

detecting first specification information indicating a region of interest in the object medical image;

receiving a first number of similar medical images, each of the similar medical images having a prescribed degree of similarity with a feature quantity of the region of interest indicated by the first specification information, each of the similar medical images being retrieved from the case retrieval system in accordance with the region of interest, disease name information being set in additional information of the similar medical images, each of the similar medical images including a corresponding region of interest that corresponds to the region of interest in the object medical image and including second specification information indicating the corresponding region of interest in each of the similar medical images;

displaying, on the display, a display screen which includes a first display region and a second display region, the first display region displaying the object medical image, the second display region displaying a second number of the similar medical images, the second display region including a third number of individual regions for displaying the second number of the similar medical images, the display screen including one or more instruction buttons, the instruction buttons being common to the second number of the similar medical images for changing a display size of the second number of the similar medical images with respect to a reference thumbnail; and when detecting an instruction from the one or more instruction buttons, changing a display size of each corresponding region of interest that is included in the second number of the similar medical images while maintaining a size of each of the individual regions in the second display region, and magnifying each of the similar medical images at a magnification ratio of the reference thumbnail, the magnification ratio being determined in accordance with a size of the corresponding region of interest of the reference thumbnail, a size of the corresponding region of interest indicated by the second specification information, and a magnification ratio of the reference thumbnail, wherein the first number is an integer at least equal to 2, the second number is an integer at least equal to 1 and at most equal to the first number, and the third number is an integer at least equal to the second number and at most equal to the first number.

2. A non-transitory computer-readable recording medium which stores a program that is executable by an information terminal, the information terminal including a display and being connected to a case retrieval system, the program configured to cause the information terminal to:

display, on the display, an object medical image which is a medical image of a diagnostic interpretation object;

detect a first specification information indicating a region of interest in the object medical image;

receive a first number of similar medical images, each of the similar medical images having a prescribed degree of similarity with a feature quantity of the region of interest indicated by the first specification information, each of the similar medical images being retrieved from the case retrieval system in accordance with the region of interest, disease name information being set in additional information of the similar medical images, each of the similar medical images including a corresponding region of interest that corresponds to the region of interest in the object medical image and including second specification information indicating the corresponding region of interest in each of the similar medical images;

display on the display a display screen which includes a first display region and a second display region, the first display region displaying the object medical image, the second display region displaying a second number of the similar medical images, the second display region including a third number of individual regions for displaying the second number of the similar medical images, the display screen including one or more instruction buttons, the instruction buttons being common to the second number of the similar medical images for changing a display size of the second number of the similar medical images with respect to a reference thumbnail; and when detecting an instruction from the one or more instruction buttons, change a display size of each corresponding region of interest that is included in the second number of the similar medical images while maintaining a size of each of the individual regions in the second display region, and magnify each of the similar medical images at a magnification ratio of the reference thumbnail, the magnification ratio being determined in accordance with a size of the corresponding region of interest of the reference thumbnail, a size of the corresponding region of interest indicated by the second specification information, and a magnification ratio of the reference thumbnail, wherein the first number is an integer at least equal to 2,
the second number is an integer at least equal to 1 and at most equal to the first number, and
the third number is an integer at least equal to the second number and at most equal to the first number.

* * * * *